United States Patent [19]

Kindon et al.

[11] Patent Number: 6,107,297

[45] Date of Patent: Aug. 22, 2000

[54] 2,4-DITHI(OXO)-PYRIMIDIN-5-YL COMPOUNDS BEARING A TRICYCLIC SUBSTITUENT USEFUL AS P2 PURINOCEPTOR ANTAGONISTS

[75] Inventors: Nicholas Kindon, Ashby de la Zouch; Premji Meghani; Stephen Thom, both of Loughborough, all of United Kingdom

[73] Assignee: Astra Pharmaceuticals Limited, Herts, United Kingdom

[21] Appl. No.: 09/155,612

[22] PCT Filed: Jun. 25, 1998

[86] PCT No.: PCT/SE98/01240

§ 371 Date: Sep. 30, 1998

§ 102(e) Date: Sep. 30, 1998

[87] PCT Pub. No.: WO99/02501

PCT Pub. Date: Jan. 21, 1999

[30] Foreign Application Priority Data

Jul. 9, 1997 [SE] Sweden ................................. 9702651

[51] Int. Cl.[7] ...................... C07D 403/04; C07D 401/04; C07D 417/14; A61K 31/506; A61K 31/513

[52] U.S. Cl. ..................... 514/252.02; 514/266; 514/269; 544/238; 544/277; 544/294; 544/296; 544/310

[58] Field of Search ............................... 514/252.02, 266, 514/269; 544/238, 277, 294, 296, 310

[56] References Cited

PUBLICATIONS

Whitehead et al., Reaction of Pyrimidines with Diarylmethyl Cations, Journal of Organic Chemistry, vol. 39, No. 5, pp. 587–591, Mar. 1974.

*Primary Examiner*—Mukund J. Shah
*Assistant Examiner*—Deepak R. Rao
*Attorney, Agent, or Firm*—Nixon & Vanderhye

[57] ABSTRACT

The invention relates to new pharmaceutically active compounds which are P2-purinoceptor 7-transmembrane (TM) G-protein coupled receptor antagonists, compositions containing them and processes for their preparation.

12 Claims, No Drawings

2,4-DITHI(OXO)-PYRIMIDIN-5-YL COMPOUNDS BEARING A TRICYCLIC SUBSTITUENT USEFUL AS P2 PURINOCEPTOR ANTAGONISTS

This application is a 371 of PCT/SE98/01240 filed Jun. 25, 1998.

The invention provides new pharmaceutically active compounds, compositions containing them and processes for their preparation. The compounds are useful in therapy because they are P2-purinoceptor 7-transmembrane (TM) G-protein coupled receptor antagonists.

ATP receptors have been shown to be present on a wide number of different cell types (Dubyak et al Am J Physiol (1993) 265, C577–C606). Neutrophils, monocytes and macrophages have been isolated from several species including humans and ATP and/or UTP have been shown to increase intracellular calcium levels. Activation of these receptors on leukocytes can either directly stimulate certain types of inflammatory response or can prime the effector cells to other inflammatory mediators in vivo. ATP can upregulate the expression of adhesion molecules (Freyer et al J Immun. (1988) 141, 580–586) which causes enhanced adhesion of circulating leukocytes to endothelial cells and is their enhanced migration into the tissue space. ATP has also been shown to promote chemotaxis of both neutrophils and eosinophils (Verghese et al J. B. C. (1996) 271, 15597–15601 and Burders et al Blood (1993) 81, 49–55) which may promote an inflammatory response. ATP priming of neutrophils can also potentiate superoxide production (Seifert et al Eur J Biochem (1989) 181, 277–285). ATP receptors are also present on a number of other cell types such as chondrocytes, keratinocytes, microglia and goblet cells (Leong et al BBA (1994) 1201, 298–304; Pillai et al J Clin Invest (1992) 90, 42–51; Walz et al J Neuroscience (1993) 13, 4403–4411 and Abdullah et al Biochem J (1996) 316, 943–951).

Stimulation of the receptors on these cells can stimulate or enhance inflammatory responses and antagonist of the receptor may therefore be of use in a number of inflammatory diseases such as asthma, inflammatory bowel disease, ARDS, psoriasis, rheumatoid arthritis, myocardial ischaemia, COPD, cystic fibrosis, arthereosclerosis, restenosis, peridontal disease, septic shock, osteoarthritis and stroke. ATP receptors have also been reported on tumour cells (Dubyak et al J. Biol. Chem., (1985) 260, 10653–10661 and Wagner et al Gastroenterolgy, (1997), 112(4) suppl. page A1198) and may be involved in the development of cancer. Antagonists may therefore be useful in treatment of cancer.

According to the invention there is provided a compound of formula (I) or salts thereof:

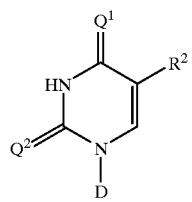

(I)

in which:

D is hydrogen, $C_{1-6}$alkyl or a group of formula (a):

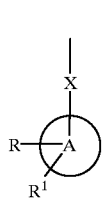

(a)

where A is a 6-membered heterocyclic ring containing 1 to 3 nitrogen atoms or a fused 5,6-bicyclic ring containing 1 to 4 nitrogen atoms;

X is a bond or $CH_2$ group;

R is hydrogen, $NO_2$, $NH_2$, $N(C_{1-6}alkyl)_2$, $CO_2H$, $CO_2C_{1-6}alkyl$, phenyl substituted by $CH_2CO_2H$, or $CONR^3R^4$ where $R^3$ and $R^4$ are independently hydrogen, $C_{1-6}$alkyl optionally substituted by hydroxy and/or optionally interrupted by oxygen, nitrogen or sulfur;

$R^1$ is —$R^5$-tetrazol-5-yl where $R^1$ is a bond, $OCH_2$, $SCH_2$, $CONH$, $CONHCH_2$, $CONHCH_2CONH$, $NHCH_2CONH$, $NHCH(R^3)$ or —$R^5$—$CO_2H$ where $R^5$ is a bond, $OCH_2$, $SCH_2$, $CONHCH_2$ or $NHCH(R^3)$ where $R^3$ is as defined above or $R^5$ is $NR^6(CH_2)_q$ where $R^6$ is hydrogen or $C_{1-6}$alkyl and q is 1 or 2, or $R^1$ is a group of formula (i):

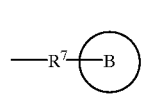

(i)

where B is a 4-, 5-, or 6-membered saturated ring containing a nitrogen atom optionally substituted by hydroxy and substituted by $CO_2H$ or $CONH$-Het where Het is tetrazol-5-yl, or a thiazole or thiadiazole ring substituted by $CH_2CO_2H$, or B is a 5-membered aromatic heterocyclic ring containing 1 to 3 heteroatoms selected from nitrogen, oxygen or sulfur optionally substituted by $CF_3$, $CO_2H$, $CH_2CO_2H$, $C(CO_2H)=N$—OMe, tetrazol-5-yl or $CH_2$tetrazol-5-yl; and $R^7$ is a bond, sulfur atom, a group —$NR^8$—$CH(CO_2H)$—$CH_2$—, or a group —$CONR^8(CH_2)_p CONR^9$— or —$NR^8$—$(CH_2)_p$—$CONR^9$— where $R^8$ and $R^9$ are independently hydrogen or $C_{1-6}$alkyl and p is 1 or 2;

$R^2$ is a group of formula (ii) or (iii):

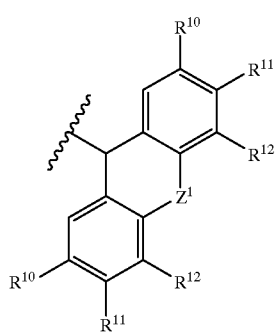

(ii)

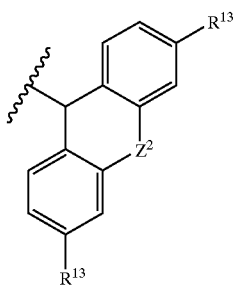
(iii)

where $R^{10}$ groups are independently hydrogen, halogen, methoxy, methylthio or $C_{1-2}$alkyl (optionally substituted by one or more fluorine atoms);

$R^{11}$ groups are independently hydrogen, halogen, hydroxy, $C_{1-3}$ alkylthio, $C_{1-4}$alkyl (optionally substituted by one or more fluorine atoms), $C_{3-4}$ cycloalkyl, $MeOCH_2$, $MeSCH_2$ or $C_{1-2}$alkoxy;

$R^{12}$ groups are independently hydrogen, halogen or methyl (optionally substituted by one or more fluorine atoms);

$Z^1$ is CH=CH, CF=CH or CF=CF;

$Z^2$ is a single bond, oxygen, sulphur, $CH_2CH$=CH, $CH_2CH$=$CHCH_2$ or a $C_{1-4}$alkylene group optionally interrupted by an oxygen or sulphur atom;

$R^{13}$ are independently hydrogen, halogen, $C_{1-2}$alkyl, $CF_3$ or a methylthio group or hydroxy;

$Q^1$ and $Q^2$ each independently represent an O or S;

provided that when $Q^1$ is oxygen, $R^2$ is a group of formula (ii).

Alkyl groups, whether alone or as part of another group, can be straight chain or branched. Unless stated otherwise, the term alkyl as used herein refers to $C_{1-6}$alkyl groups, such as methyl, ethyl, propyl and butyl groups.

Certain compounds of formula (I) are capable of existing in stereoisomeric forms including enantiomers and the invention extends to each of these stereoisomeric forms and to mixtures thereof including racemates. The different stereoisomeric forms may be separated one from the other by the usual methods, or any given isomer may be obtained by stereospecific or asymmetric synthesis. The invention also extends to any tautomeric forms and mixtures thereof.

Suitably D is hydrogen, $C_{1-6}$alkyl or a group of formula (a) as defined above. When D is $C_{1-6}$alkyl, preferred alkyl groups include methyl.

Preferably D is a group of formula (a) where A is a 6-membered heterocyclic ring containing 1 or 2 nitrogen atoms or a fused 5,6-bicyclic ring containing 4 nitrogen atoms. Examples of suitable 6-membered heterocyclic rings include pyridine and pyrimidine rings. More preferably A is pyrimidine. Preferably R and $R^1$ are meta or para with respect to the uracil group.

Suitably X is a bond or $CH_2$ group. Preferably X is $CH_2$ when A is pyridine and X is a bond when A is pyrimidine.

Suitably R is hydrogen, $NO_2$, $NH_2$, $N(C_{1-6}alkyl)_2$, $CO_2H$, $CO_2C_{1-6}$alkyl, phenyl substitute by $CH_2CO_2H$, or $CONR^3R^4$ where $R^1$ and $R^4$ are independently hydrogen, $C_{1-6}$alkyl optionally substituted by hydroxy and optionally interrupted by oxygen, nitrogen or sulfur. Preferably R is hydrogen.

Suitably $R^1$ is —$R^1$-tetrazol-5-yl where $R^5$ is a bond, $OCH_2$, $SCH_2$, CONH, $CONHCH_2$, $CONHCH_2CONH$, $NHCH_2CONH$, $NHCH(R^3)$ or —$R^5$—$CO_2H$ where $R^5$ is a bond, $OCH_2$, $SCH_2$, $CONHCH_2$ or $NHCH(R^3)$ where $R^3$ is as defined above or $R^5$ is $NR^6(CH_2)_q$ where $R^6$ is hydrogen or $C_{1-6}$alkyl and q is 1 or 2, or $R^1$ is a group of formula (i) as defined above. When $R^1$ is —$R^5$—$CO_2H$, $R^5$ is preferably $SCH_2$, $NHCH_2$ or $NMeCH_2$. When $R^1$ is a group of formula (i) then $R^7$ is preferably a bond when B is a 4-, 5- or 6-membered saturated ring containing a nitrogen atom substituted by $CO_2H$ and optionally substituted by hydroxy.

When B is a 5-membered aromatic heterocycle then $R^7$ is preferably a group —$CONR^8(CH_2)_pCONR^9$— or —$NR^8$—$(CH_2)_p$—$CONR^9$— particularly such a group where $R^8$ is hydrogen or methyl and $R^9$ is hydrogen and p is 1. Preferred rings B include substituted thiazole and thiadiazole substituted by $CO_2H$ or $CH_2CO_2H$, more preferably substituted by $CH_2CO_2H$.

Suitably $R^2$ is a group of formula (ii) or (iii). Preferably $R^2$ is a group of formula (ii) where $Z^1$ is CH=CH. Suitably $R^{11}$ groups are independently hydrogen, halogen, hydroxy, $C_{1-3}$ alkylthio, $C_{1-4}$alkyl (optionally substituted by one or more fluorine atoms), $C_{3-4}$ cycloalkyl, $MeOCH_2$, $MeSCH_2$ or $C_{1-2}$alkoxy. Preferably both $R^{11}$ groups are hydrogen or methyl or one is methyl and the other is ethyl or propyl. Preferably $R^{10}$ and $R^{12}$ are both hydrogen.

Suitably $Q^1$ and $Q^2$ each independently represent an O or S. Preferably $Q^1$ is S or O and $Q^2$ is O.

Particularly preferred compounds of the invention include:

6-[[5-{5H-Dibenzo[a,d]cyclohepten-5-yl}-3,4-dihydro-2-oxo-4-thioxo-1(2H)-pyrimidinyl]methyl]-2-pyridinecarboxylic acid 2-[[6-[5-{5H-Dibenzo[a,d]cyclohepten-5-yl}-3,4-dihydro-2-oxo-4-thioxo-1(2H)-pyrimidinyl]pyridazin-3-yl]thio]acetic acid 5-[5H-Dibenzo[a,d]cyclohepten-5-yl]-1-[6-[[5-[trifluoromethyl]-1,2,4-triazol-3-yl]thio]pyridazin-3-yl]-2,4(1H,3H)-pyrimidinedione 5-[5H-Dibenzo[a,d]cyclohepten-5-yl]-3,4-dihydro-4-thioxo-1-[6-[[5-[trifluoromethyl]-1,2,4-triazol-3-yl]thio]pyridazin-3-yl]-2(1H)-pyrimidinone 4-[2-[5-{5H-Dibenzo[a,d]cyclohepten-5-yl}-3,4-dihydro-2-oxo-4-thioxo-1(2H)-pyrimidinyl]-4-[carboxymethylthio]pyrimidin-5-yl]phenylacetic acid 2-[[4-[5-{5H-Dibenzo[a,d]cyclohepten-5-yl}-3,4-dihydro-2-oxo-4-thioxo-1(2H)-pyrimidinyl]pyrimidin-2-yl]thio]acetic acid N-[4-[5-{5H-Dibenzo[a,d]cyclohepten-5-yl}-3,4-dihydro-2-oxo-4-thioxo-1(2H)-pyrimidinyl]pyrimidin-2-yl]glycine N-[4-[5-{2,8-Dimethyl-5H-dibenzo[a,d]cyclohepten-5-yl}-3,4-dihydro-2,4-dioxo-1(2H)-pyrimidinyl]pyrimidin-2-yl]glycine N-[4-[5-{2,8-Dimethyl-5H-dibenzo[a,d]cyclohepten-5-yl}-3,4-dihydro-2-oxo-4thioxo-1(2H)-pyrimidinyl]pyrimidin-2-yl]glycine 2-[2-[[4-[5-{2,8-Dimethyl-5H-dibenzo[a,d]cyclohepten-5-yl}-3,4-dihydro-2,4-dioxo-1(2H)-pyrimidinyl]pyrimidin-2-yl]amino]acetylamino]-4-thiazoleacetic acid N-[4-[5-{5H-Dibenzo[a,d]cyclohepten-5-yl}-3,4-dihydro-2,4-dioxo-1(2H)-pyrimidinyl]pyrimidin-2-yl]-L-proline N-[4-[-5-{2,8-Dimethyl-5H-dibenzo[a,d]cyclohepten-5-yl}-3,4-dihydro-2,4-dioxo-1(2H)-pyrimidinyl]pyrimidin-2-yl]-L-proline (2S-trans)-N-[4-[5-{2,8-Dimethyl-5H-dibenzo[a,d]cyclohepten-5-yl}-3,4-dihydro-2,4-dioxo-1(2H)- pyrimidinyl]pyrimidin-2-yl]-4-hydroxy-2-pyrrolidinecarboxylic acid

N$^\alpha$-[4-[5-{2,8-Dimethyl-5H-dibenzo[a,d]cyclohepten-5-yl}-3,4-dihydro-2,4-dioxo-1(2H)-pyrimidinyl]pyrimidin-2-yl]-L-histidine (±)-2-[2-[[4-[5-{2-Ethyl-8-methyl-5H-dibenzo[a,d]cyclohepten-5-yl}-3,4dihydro-2,4-dioxo-1(2H)-pyrimidinyl]pyrimidin-2-yl]amino]acetylamino]-4-thiazoleacetic acid 2-[2-[[2-[Dimethylamino]-4-[5-{2,8-dimethyl-5H-dibenzo[a,d]cyclohepten-5-yl}-3,4-dihydro-2,4-dioxo-1(2H)-pyrimidinyl]pyrimidin-6-yl]amino]acetylamino]-4-thiazoleacetic acid N-[2-[5-{2,8-Dimethyl-5H-dibenzo[a,d]cyclohepten-5-yl}-3,4-dihydro-2,4-dioxo-1(2H)-pyrimidinyl]-5-[methoxycarbonyl]pyrimidin-4-yl]glycine 4-[[Carboxymethyl]amino]-2-[5-{2,8-dimethyl-5H-dibenzo[a,d]cyclohepten-5-yl}-3,4-dihydro-2,4-dioxo-1(2H)-pyrimidinyl]-5-pyrimidinecarboxylic acid (±)-N-[4-[5-{2-Ethyl-8-methyl-5H-dibenzo[a,d]cyclohepten-5-yl}-3,4-dihydro-2-oxo-4-thioxo-1(2H)-pyrimidinyl]pyrimidin-2-yl]-N-methylglycine (±)-2-[2-[[4-[5-{2-Ethyl-8-methyl-5H-dibenzo[a,d]cyclohepten-5-yl}-3,4-dihydro-2-oxo-4-thioxo-1(2H)-pyrimidinyl]pyrimidin-2-yl][methyl]amino]acetylamino]-4-thiazoleacetic acid 2-[2-[[4-[5-{2,8-Dimethyl-5H-dibenzo[a,d]cyclohepten-5-yl}-3,4-dihydro-2,4-dioxo-1(2H)-pyrimidinyl]pyrimidin-2-yl][methyl]amino]acetylamino]-4-thiazoleacetic acid (±)-2-[2-[[4-[5-{2-Ethyl-8-methyl-5H-dibenzo[a,d]cyclohepten-5-yl)-3,4-dihydro-2,4-dioxo-1(2H)-pyrimidinyl]pyrimidin-2-yl][methyl]amino]acetylamino]-4-thiazoleacetic acid (±)-2-[2-[[4-[3,4-Dihydro-5-{2-methoxy-8-methyl-5H-dibenzo[a,d]cyclohepten-5-yl}-2,4-dioxo-1(2H)-pyrimidinyl]pyrimidin-2-yl][methyl]amino]acetylamino]-4-thiazoleacetic acid (±)N-[4-[5-{2-Ethyl-8-methyl-5H-dibenzo[a,d]cyclohepten-5-yl}-3,4-dihydro-2,4-dioxo-1(2H)-pyrimidinyl]pyrimidin-2-yl]-3-azetidinecarboxylic acid 2-[2-[[6-[5-{2,8-Dimethyl-5H-dibenzo[a,d]cyclohepten-5-yl}-3,4-dihydro-2-oxo-4-thioxo-1(2H)-pyrimidinyl]pyrimidin-4-yl][methyl]amino]acetylamino]-4-thiazoleacetic acid (±)-N-[4-[5-{2-Ethyl-8-methyl-5H-dibenzo[a,d]cyclohepten-5-yl}-3,4-dihydro-2-oxo-4-1(2H)-pyrimidinyl]pyrimidin-2-yl]-L-proline (±)-N-[4-[5-{2-Ethyl-8-methyl-5H-dibenzo[a,d]cyclohepten-5-yl}-3,4-dihydro-2-oxo-4-thioxo-1(2H)-pyrimidinyl]pyrimidin-2-yl]-L-proline (±)-2-[5-{2-Ethyl-8-methyl-5H-dibenzo[a,d]cyclohepten-5-yl}-3,4-dihydro-2,4-dioxo-1(2H)-pyrimidinyl]-9H-purine-9-acetic acid.

N-[2-[5-{2-Ethyl-8-methyl-5H-dibenzo[a,d]cyclohepten-5-yl}-3,4-dihydro-2,4-dioxo-1(2H)-pyrimidinyl]-5-nitropyrimidin-4-yl]glycine.

(±)-2-[2-[[4-[3,4-dihydro-5-{2-methyl-8-[1-methylethyl]-5H-dibenzo[a,d]cyclohepten-5-yl}-2,4-dioxo-1(2H)-pyrimidinyl]pyrimidin-2-yl]amino]acetylamino]-4-thiazoleacetic acid (±)-2-[2-[[4-[3,4-Dihydro-5-{2-methyl-8-propyl-5H-dibenzo[a,d]cyclohepten-5-yl}-2,4-dioxo-1(2H)-pyrimidinyl]pyrimidin-2-yl]amino]acetylamino]-4-thiazoleacetic acid (±)-N-[4-[3,4-Dihydro-5-{2-methyl-8-propyl-5H-dibenzo[a,d]cyclohepten-5-yl}-2-oxo-4-thioxo-1(2H)-pyrimidinyl]pyrimidin-2-yl]-N-methylglycine (±)-2-[2-[[4-[5-{2-Ethyl-8-methyl-5H-dibenzo[a,d]cyclohepten-5-yl}-3,4-dihydro-2,4-dioxo-1(2H)-pyrimidinyl]pyrimidin-2-yl]amnino]acetylamino]-5-thiazoleacetic acid (±)-2-[2-[[4-[5-{2-Ethyl-8-methyl-5H-dibenzo[a,d]cyclohepten-5-yl}-3,4-dihydro-2,4-dioxo-1(2H)-pyrimidinyl]pyrimidin-2-yl][methyl]amino]acetylamino]-4-thiazolecarboxylic acid.

(±)-2-[[1-[4-[5-{2-Ethyl-8-methyl-5H-dibenzo[a,d]cyclohepten-5-yl}-3,4-dihydro-2,4-dioxo-1(2H)-pyrimidinyl]pyrimidin-2-yl]azetidin-3-yl]carbonylamino]-4-thiazoleacetic acid (±)-2-[2-[[4-[3,4-Dihydro-5-{2-hydroxy-8-methyl-5H-dibenzo[a,d]cycloheptne-5-yl}-2,4-dioxo-1(2H)-pyrimidinyl]pyrimidin-2-yl]amino]acetylamino]-4-thiazoleacetic acid.

(±)-2-[2-[[4-[5-{2-Ethyl-8-methyl-5H-dibenzo[a,d]cyclohepten-5-yl}-3,4-dihydro-2,4-dioxo-1(2H)-pyrimidinyl]pyrimidin-2-yl][methyl]amino]acetylamino]-α-[methoxyimino]-4-thiazoleacetic acid (±)-N-[(1H)-Tetrazol-5-yl]-1-[4-[5-{2-ethyl-8-methyl-5H-dibenzo[a,d]cyclohepten-5-yl}-3,4-dihydro-2,4-dioxo-1(2H)-pyrimidinyl]pyrimidin-2-yl]-3-azetidinecarboxamide (±)-2-[4-[5-{2-Ethyl-8-methyl-5H-dibenzo[a,d]cyclohepten-5-yl}-3,4-dihydro-2,4-dioxo-1(2H)-pyrimidinyl]pyrimidin-2-yl]amino-N-[4-[1H-tetrazol-5-ylmethyl]thiazol-2-yl]acetamide (±)[[5-[[4-[5-{2-Ethyl-8-methyl-5H-dibenzo[a,d]cyclohepten-5-yl}-3,4-dihydro-2,4-dioxo-1(2H)-pyrimidinyl]pyrimidin-2-yl]amino]acetylamino]-3-(1,2,4-thiadiazole)]acetic acid (±)2-[5-{2-Ethyl-8-methyl-5H-dibenzo[a,d]cyclohepten-5-yl}-3,4-dihydro-2,4-dioxo-1(2H)-pyrimidinyl]-4-pyrimidinecarboxylic acid (±)N-[[[2-[5-{2-Ethyl-8-methyl-5H-dibenzo[a,d]cyclohepten-5-yl}-3,4-dihydro-2,4-dioxo-1(2H)-pyrinmidinyl]pyrimidin-4-yl]carbonyl]glycine (±)2-[5-{2-Ethyl-8-methyl-5H-dibenzo[a,d]cyclohepten-5-yl}-3,4-dihydro-2,4-dioxo-1(2H)-pyrimidinyl]-N-[(1H)-tetrazol-5-yl]-4-pyrimidinecarboxamide (±)2-[[6-[5-{2-Ethyl-8-methyl-5H-dibenzo[a,d]cyclohepten-5-yl}-3,4-dihydro-2,4-dioxo-1(2H)-pyrimidinyl]pyridazin-3-yl]thio]acetic acid (±)2-[4-[5-{2-Ethyl-8-methyl-5H-dibenzo[a,d]cyclohepten-5-yl}-3,4-dihydro-2,4-dioxo-1(2H)-pyrimidinyl]pyrimidin-2-yl]amino]-N-[(1H)-tetrazol-5-yl]acetamide (±)N-[4-[5-{2-Ethyl-8-hydroxy-5H-dibenzo[a,d]cyclohepten-5-yl}-3,4-dihydro-2,4-dioxo-1(2H)-pyrimidinyl]pyrimidin-2-yl]-3-azetidinecarboxylic acid (±)2-[[[4-[5-{2-Ethyl-8-hydroxy-5H-dibenzo[a,d]cyclohepten-5-yl}-3,4-dihydro-2,4-dioxo-1(2H)-pyrimidinyl]pyrimidin-2-yl]amino]acetylamino]-4-thiazoleacetic acid (±)2-[5-{2-Ethyl-8-methyl-5H-dibenzo[a,d]cyclohepten-5-yl}-3,4-dihydro-2,4-dioxo-1(2H)-pyrimidinyl]-N-[{(1H)-tetrazol-5-ylamino}carboxymethyl]-4-pyrimidinecarboxamide (±)-4-[Carboxymethylamino]-2-[5-[2-ethyl-8-methyl-5H-dibenzo[a,d]cyclohepten-5-yl]-3,4-dihydro-2,4-dioxo-2H-pyrimidin-1-yl]-5-pyrimidinecarboxylic acid 5-[2,8-Dimethyl-5H-dibenzo[a,d]cyclohepten-5-yl]-3,4-dihydro-2-oxo-4-thioxo-1(2H)-pyrimidine 5-[2,8-Dimethyl-5H-dibenzo[a,d]cyclohepten-5-yl]-1-methyl-3,4-dihydro-2-oxo-4-thioxo-1(2H)-pyrimidine and salts thereof.

In a further aspect the invention provides a process for the preparation of a compound of formula (I) which comprises:

(a) reacting a compound of formula (II):

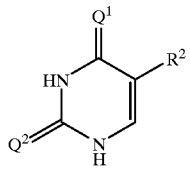

(II)

where $Q^1$ and $Q^2$ are as defined in formula (I) and $R^2$ is as defined in formula (I) or is a protected derivative thereof with a compound of formula (III):

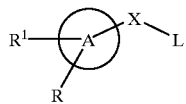

(III)

where R, $R^1$ and A are as defined in formula (I) or are protected derivatives thereof, X is as defined in formula (I) and L is a leaving group, or (b) reacting a compound of formula (IV):

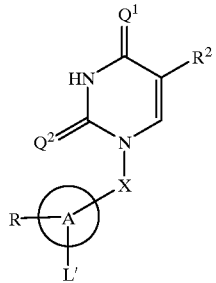

(IV)

where $Q^1$, $Q^2$, $R^2$ and X are as defined in formula (I), R and A are as defined in formula (I) or are protected derivatives thereof and L' is a leaving group with a compound of formula (V), (VI) or (VII):

$HNR^8—(CH_2)_p—CONR^9—B$ (V)

$HNR^8—CH(CO_2H)—CH_2—B$ (VI)

(VII)

where $R^8$, $R^9$ and p are as defined in formula (I) and B is as defined in formula (I) or is a protected derivative thereof, or (c) when $R^1$ is a group $—R^5—CO_2H$ and $R^5$ is $SCH_2$ or $NR^6(CH_2)_q$, reacting a compound of formula (iv) as defined above with a compound $H—R^5—CO_2R^{14}$ where $R^5$ is $SCH_2$ or $NR^6(CH_2)_q$ and $R^{14}$ is an ester forming group;

and optionally thereafter (a), (b) or (c) in any order:
  removing any protecting groups
  converting the compound of formula (I) into a further compound of formula (I)
  forming a salt Reaction of compounds of formulae (II) and (III) can be carried out in the presence of a suitable base, for example a metal carbonate such as potassium carbonate or cesium carbonate in a suitable polar solvent such as NMP, dimethylformamide or dimethylsulphoxide at ambient or elevated temperature, for example at about 80° C. Preferably L is halogen when X is a bond, in particular chloro or fluoro. When X is $CH_2$ L is preferably chloro. Alternatively for compounds where X is $CH_2$ the compound of formula (II) can be silylated with a suitable silylating reagent such as a trialkylsilylchloride and/or 1,1,1,3,3,3-hexamethyldisilazane in a suitable solvent such as pyridine, toluene or 1,4-dioxane at a temperature of about 80° C. to about 140° C. followed by addition of the compound of formula (III) in a suitable solvent such as acetonitrile at elevated temperature, for example at reflux. We prefer to silylate using bis(trimethylsilyl)trifluoroacetamide in refluxing 1,2-dichloroethane followed by treatment the appropriate compound of formula (III) (where L is halogen, preferably bromide or chloride) in acetonitrile and 1,2-dichloroethane at reflux.

Compounds of formula (IV) can be reacted with compounds $H—R^5—CO_2H$ in the presence of a suitable base. When $R^1$ is $SCH_2$ the base is preferably NaH and when $R^5$ is $NR^6(CH_2)^q$ the base is preferably an organic amine such as di-isopropylethylamine. The group $R^{14}$ is a suitable ester forming group such as benzyl or $C_{1-6}$ alkyl. Compounds of formula (IV) can also be reacted with compounds of formulae (V), (VI) or (VII) using the procedure described above for when $R^5$ is $NR^6(CH_2)_q$.

It will be appreciated by those skilled in the art that in the process described above the functional groups of intermediate compounds may need to be protected by protecting groups.

Functional groups which it is desirable to protect include hydroxy, amino and carboxylic acid. Suitable protecting groups for hydroxy include organosilyl groups (e.g. tert-butyldimethylsilyl, tert-butyldiphenylsilyl or trimethylsilyl), benzyl and tetrahydropyranyl. Suitable protecting groups for amino include tert-butoxycarbonyl or benzyloxy carbonyl. Suitable protecting groups for carboxylic acid include $C_{1-6}$ alkyl or benzyl esters. The protection and deprotection of functional groups may take place before or after a reaction step.

The use of protecting groups is fully described in 'Protective Groups in Organic Chemistry', edited by J. W. F. McOmie, Plenum Press (1973), and 'Protective Groups in Organic Synthesis', 2nd edition, T. W. Greene & P. G. M. Wutz, Wiley-Interscience (1991).

In particular compounds of formula (III) where $R^1$ contains a carboxylic acid group can be protected as esters, particularly as $C_{1-6}$alkyl esters. Basic hydrolysis of such esters can be performed using metal hydroxides or quaternary ammonium hydroxides such as sodium hydroxide in a solvent such as an aqueous alcohol, 1,4-dioxane, tetrahydrofuran or dimethylformamide at a temperature between 10° C. and 100° C. When $Q^1/Q^2$ are oxygen, acidic hydrolysis may also be performed using mineral acid such as HCl or a strong organic acid such as trifluoroacetic acid in a suitable solvent such as 1,4-dioxane. We prefer basic hydrolysis using lithium hydroxide in aqueous tetrahydrofuran or aqueous methanol at ambient temperature.

Compounds of formula (I) can be converted into further compounds of formula (I) using standard procedures, for example using known alkylation, hydrolysis, esterification and amide formation chemistry. Compounds of formula (I) where $Q^1$ is oxygen can be converted to a corresponding compound of formula (I) where $Q^1$ is sulfur using standard thiation conditions for conversion of uridine and thymidine nucleosides in their corresponding thio-nucleoside derivatives (see "Chemistry of Nucleosides and Nucleotides" edited by Leroy B. Townsend, Plenum Press volume 1). Thiation may be achieved using reagents such as diphosphorus pentasulphide or Lawesson's reagent in a solvent such as pyridine, 1,4-dioxane, toluene, xylene, or tetrahydrofuran at a temperature of about 50° C. to about 130° C. We prefer to use Lawesson's reagent in 1,4-dioxane at about 100° C. when selectivity can be achieved.

Thiation can also be achieved by displacement of a suitable leaving group in the 2- or 4-position of the uracil by hydrogen sulphide in a suitable solvent such as pyridine and triethylamine at ambient temperature. Suitable leaving groups include alkylthio or halogen, preferably alkylthio, more preferably methylthio.

Compounds of formula (II) where $Q^1$ and $Q^2$ are oxygen can be prepared by reaction of a compound of formula (VIII):

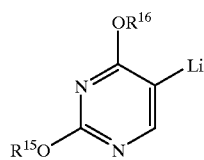
(VIII)

where $R^{15}$ and $R^{16}$ are independently $C_{1-6}$alkyl or benzyl with a compound of formula (IX) or (X):

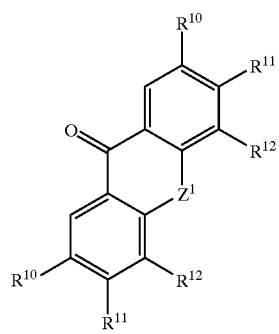
(IX)

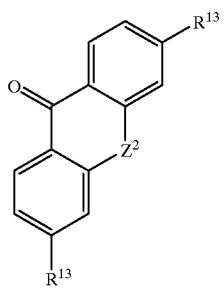
(X)

where $Z^1$, $Z^2$, $R^{10}$, $R^{11}$, $R^{12}$ and $R^{13}$ groups are as defined in formula (I) followed by reduction of the resulting alcohol. Compounds of formula (VIII) are prepared by treating the corresponding halide with an alkyl lithium reagent (alkyl=n-Butyl, sec-Butyl, tert-Butyl) in solvents such as tetrahydrofuran or diethyl ether at low temperature e.g. −40° C. to −78° C.

The resulting alcohol can then be reduced to compounds of type (II) by treatment with a trialkylsilane such as triethylsilane in a suitable solvent such as dichloromethane, chloroform, or 1,2-dichloroethane and an acid or Lewis acid such as trifluoroacetic acid or borontrifluoride diethyl ether complex. We preferred to perform the metal halogen exchange on 5-bromo-2,4-bis(1,1-dimethylethoxy) pyrimidine using n-butyl lithium at about −78° C. in tetrahydrofuran.

When the lithio species is quenched with a substituted 10,11-dihydro-5H-dibenzo[a,d]cyclohepten-5-one the resulting substituted 5-(2,4-bis(alkoxy)pyrimidin- 5-yl)-10, 11-dihydro-5H-dibenzo[a,d]cyclohepten-5-ol can then be converted to the uracil of formula (II) (where $Z^1$ is CH=CH) by refluxing in a carboxylic acid solvent (D. Hellwinkel and T. Becker, Chem. Ber., 1989, 122, 1595). Preferred acids include acetic acid. In some cases further treatment with trifluoroacetic acid at reflux may be required for the dehydration to give the substituted uracil (II).

Compounds of formula (II) can also be prepared from uracil and the appropriately substituted alcohols of formula (XI) and (XII):

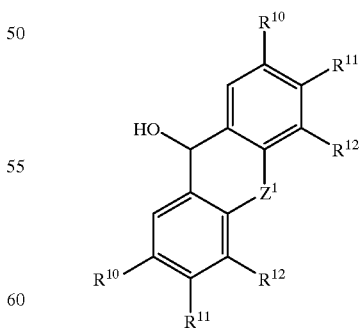
(XI)

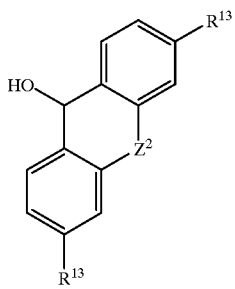

(XII)

in which $Z^1$, $Z^2$, $R^{10}$, $R^{11}$, $R^{12}$ and $R^{13}$ groups are as defined in formula (I) by refluxing in a carboxylic acid solvent such as acetic acid (J.O.C., 1974, 39, 587).

Salts of the compounds of formula (I) may be formed by reacting the free acid, or a salt thereof, with one or more equivalents of the appropriate base (for example ammonium hydroxide optionally substituted by $C_{1-6}$-alkyl or an alkali metal or alkaline earth metal hydroxide). The reaction may be carried out in a solvent or medium in which the salt is insoluble or in a solvent in which the salt is soluble, e.g. water, alcohol or acetone, which may be removed in vacuo, or by freeze drying. The reaction may also be a metathetical process or it may preferably be carried out on an ion exchange resin. The non-toxic pharmaceutically acceptable salts are preferred, although other salts may be useful, e.g. in isolating or purifying the product.

Novel intermediates form a further aspect of the invention.

The compounds of the invention have been submitted to the assay outlined below and have been found to be P2 7-TM G-protein receptor antagonists, particularly to the P2Y2 receptor. Accordingly they are useful in therapy and are, in particular, indicated for use as anti-inflammatory agents useful in a number of inflammatory diseases such as asthma, inflammatory bowel disease, ARDS, psoriasis, rheumatoid arthritis, myocardial ischaemia, COPD, cystic fibrosis, arthereosclerosis, restenosis, peridontal disease, septic shock, osteoarthritis and stroke. The compounds of the invention can be co-administered with other anti-inflammatory agents. ATP receptors have also been reported on tumour cells and may be involved in the development of cancer. Antagonists may therefore be useful in treatment of cancer.

The invention provides in a further aspect a method of treating an inflammatory condition which comprises administering to a patient in need of therapy, a therapeutically effective amount of a compound of the invention.

According to the invention there is further provided use of the compounds of the invention in the manufacture of a medicament for use in the treatment of an inflammatory condition.

The compounds may be administered orally, topically e.g. to the lung and/or the airways, in the form of solutions, suspensions, HFA areosols and dry powder formulations, e.g. Turbuhaler® formulations or by parenteral administration in the form of sterile parenteral solutions or suspensions.

The invention further provides a pharmaceutical composition comprising a compound according to the present invention in association with a pharmaceutically acceptable excipient and/or adjuvant. Particularly preferred are compositions not containing material capable of causing an adverse, e.g. an allergic, reaction. For example a chelating or sequestering agent, an antioxidant, a tonicity adjusting agent, a pH modifying agent and/or a buffering agent are suitable additives.

The compounds of the invention may also be administered by means of a dry powder inhaler. The inhaler may be a single or a multi dose inhaler, and may be a breath actuated dry powder inhaler.

A pharmaceutical composition according to the present invention could optionally be prepared in freeze dried form using any lyophilisation techniques commonly used within the pharmaceutical area. Upon use but before administration, such pharmaceutical compositions are generally reconstituted in a pharmaceutically acceptable excipient. Preferably a solution of the pharmaceutical composition according to the invention obtained after reconstitution is an isotonic solution. Such a pharmaceutical composition according to the present invention when reconstituted is preferably administered by injection, for example intravenously, subcutaneously or intramuscularly.

In the examples the NMR spectra were measured on a Varian Unity Inova 300 or 400 MHz spectrometer and the MS spectra measured as follows: EI spectra were obtained on a VG 70-250S or Finnigan Mat Incos-XL spectrometer, ESI and APCI spectra were obtained on Finnigan Mat SSQ7000 or a Micromass Platform spectrometer. Where necessary, the reactions were performed under an inert atmosphere of either nitrogen or argon. Where necessary, preparative HPLC separations were generally performed using a Novapak®, Bondapak®, or Hypersil® column packed with BDSC-18 reverse phase silica gel. Chromatography was generally performed using Matrex Silica 60® (35–70 micron) or Prolabo Silica gel 60® (35–75 micron) suitable for flash silica gel chromatography.

EXAMPLE 1

6-[[5-{5H-Dibenzo[a,d]cyclohepten-5-yl}-3,4-dihydro-2-oxo-4-thioxo-1(2H)-pyrimidinyl]methyl]-2-pyridinecarboxylic acid i) 6-Hydroxymethyl-2-pyridinecarboxylic acid, methyl ester A mixture of 2,6-pyridinedicarboxylic acid (10 g) in thionyl chloride (40 ml) with catalytic dimethylformamide was heated at reflux for 4 hours. The mixture was evaporated to dryness and azeotroped with toluene. Toluene (20 ml) was added to the residue followed by methanol (20 ml). The solvent was evaporated and the residue was partitioned between ethyl acetate and aqueous sodium bicarbonate. The organic phase was dried ($MgSO_4$) and evaporated. The residue was dissolved in methanol and sodium borohydride (0.96 g) was added. The mixture was heated at reflux for 2 hours and evaporated. The residue was partitioned between chloroform and water. The organic phase was dried ($MgSO_4$) and evaporated. Purification was by chromatography eluting with 5% methanol in chloroform. Yield 2.76 g.

1H NMR: δ ($CDCl_3$) 8.04(d,1H), 7.86(t,1H), 7.56(d,1H), 4.88(d,2H), 4.00(s,3H), 3.74(t,1H).

ii) 6-Chloromethyl-2-pyridinecarboxylic acid, methyl ester

To a solution of the product from step (i) (2.75 g) in ethyl acetate (10 ml) was added 1M ethereal HCl (10 ml). The mixture was stirred for 10 minutes and the precipitate filtered off. This was dissolved in thionyl chloride (20 ml) at 0° C. After 2 hours the mixture was warmed to room temperature. Diethyl ether (100 ml) was added and the precipitate filtered off and used directly in the next step. Yield 1.3 g.

iii) 5-Bromo-2,4-bis[1,1-dimethylethoxy]pyrimidine

To a solution of potassium tert-butoxide (67.5 g) in tetrahydrofuran (500 ml) was added dropwise a solution of 5-bromo-2,4-dichloropyrimidine (55 g) (J.Am.Chem.Soc. 1934,56,134) in tetrahydrofuran (100 ml). After 1.5 hours, water (100 ml) was added carefully and the mixture extracted with ethyl acetate. The combined extract was washed with water, dried (MgSO$_4$) and evaporated under reduced pressure. Purification was by chromatography eluting with 5% triethylamine in isohexane. Yield 52.4 g.

MS: GC-MS: 302/304 (M$^+$).

iv) 5-{5H-Dibenzo[a,d]cyclohepten-5-yl}-2,4(1H,3H)-pyrimidinedione

To a solution of 5-bromo-2,4-bis(1,1-dimethylethoxy)pyrimidine (50 g) in dry tetrahydrofuran (11) at −78° C. was added n-butyllithium (69 ml of a 2.5M solution in hexanes) dropwise. After 0.5 hours, a solution of 5H-dibenzo[a,d]cyclohepten-5-one (44 g) in tetrahydrofuran (100 ml) was added. The reaction mixture was stirred at −78° C. for three hours and then allowed to warm to room temperature overnight. Saturated aqueous ammonium chloride solution (400 ml) was added and the mixture extracted with ethyl acetate. The organic solution was dried (MgSO$_4$) and evaporated under reduced pressure to give the crude 5-(2,4-bis(1,1-dimethylethoxy)pyrimidin-5-yl)-5H-dibenzo[a,d]cyclohepten-5-ol which was used directly.

To a stirred solution of the 5-(2,4-bis(1,1-dimethylethoxy)pyrimidin-5-yl)-5H-dibenzo[a,d]cyclohepten-5-ol and triethylsilane (64 ml) in dry dichloromethane (400 ml) at 0° C. was added trifluoroacetic acid (150 ml) dropwise over ten minutes. The cooling bath was removed and the solution was stirred at room temperature overnight. Toluene (300 ml) was added and solution was evaporated under vacuum. The residue was azeotroped with toluene (3 times). The oil was treated with diethyl ether and the precipitated product collected as a white powder (44 g).

MS: EI: 302 (M+,100%).

v) 6-[[5-{5H-Dibenzo[a,d]cyclohepten-5-yl}-3,4-dihydro-2,4-dioxo-1(2H)-pyrimidinyl]methyl]-2-pyridinecarboxylic acid, methyl ester Cesium carbonate (1.63 g) was added to a stirred solution of the product of step (iv) (1.5 g) in dimethylsulphoxide (20 ml). After 15 minutes triethylamine (0.71 ml) was added followed by the product from step (ii) (1.11 g). The mixture was stirred at room temperature for 4 hours and partitioned between ethyl acetate and water. The organic phase was dried (MgSO$_4$) and evaporated. Purification was by chromatography eluting with 5% methanol in chloroform. Yield 1.86 g.

MS: APCI(+ve): 452 (M+1).

vi) 6-[[5-{5H-Dibenzo[a,d]cyclohepten-5-yl}-3,4-dihydro-2-oxo-4-thioxo-1(2H)-pyrimidinyl]methyl]-2-pyridinecarboxylic acid, methyl ester A mixture of the product from step (v) (1.84 g) and Lawesson's reagent (1.65 g) in 1,4-dioxane (30 ml) was heated at reflux for 24 hours. The mixture was partitioned between ethyl acetate and aqueous sodium bicarbonate. The organic phase was dried (MgSO$_4$) and evaporated. Purification was by chromatography eluting with 50% ethyl acetate in isohexane. Yield 1.38 g.

MS: APCI(+ve): 468 (M+1).

vii) 6-[[5-5H-Dibenzo[a,d]cyclohepten-5-yl}-3,4-dihydro-2-oxo-4-thioxo-1(2H)-pryimidinyl]methyl]-2-pyridinecarboxylic acid A mixture of the product from step (vi) (1.37 g) and lithium hydroxide monohydrate (0.588 g) in methanol (20 ml) and water (15 ml) was stirred at room temperature for 3 hours. A precipitate formed which was filtered off and partitioned between ethyl acetate and 1N HCl. The organic phase was dried (MgSO$_4$) and concentrated under reduced pressure to 10 ml. The product was precipitated by the addition of diethyl ether. Yield 0.56 g.

MS: APCI(+ve): 454 (M+1, 100%); 1H NMR: δ (DMSO) 13.34(br s,1H), 12.67(s,1H), 8.02(d,2H), 7.61(d,2H), 7.49–7.23(m,7H), 7.08(s,1H), 6.77(s,2H), 5.83(s,1H), 5.00 (s,2H). MP:235–236° C.

EXAMPLE 2

2-[[6-[5-{5H-Dibenzo[a,d]cyclohepten-5-yl}-3,4-dihydro-2-oxo-4-thioxo-1(2H)-pyrimidinyl]pyridazin-3-yl]thio]acetic acid i) 5-{5H-Dibenzo[a,d]cyclohepten-5-yl}-1-[6-chloropyridazin-3-yl]-2,4(1H,3H)-pyrimidinedione Cesium carbonate (2.15 g) was added to a stirred solution of the product of example 1 step (iv) (2 g) in dimethylsulphoxide (20 ml). After 5 minutes 3,6-dichloropyridazine (1 g) was added and the mixture heated at 80° C. for 3 hours. The mixture was partitioned between ethyl acetate and water. The organic phase was dried (MgSO4) and evaporated. The residue was purified by chromatography eluting with 50% ethyl acetate in isohexane. Yield 1.8 g.

1H NMR: δ (DMSO) 11.70(s,1H), 8.08(d,1H), 8.01(d, 1H), 7.60(d,2H), 7.42–7.28(m,7H), 6.99(s,2H), 5.46(s,1H).

ii) 2-[[6-[5-{5H-Dibenzo[a,d]cyclohepten-5-yl}-3,4-dihydro-2,4-dioxo-1(2H)-pyrimidinyl]pyridazin-3-yl]thio]acetic acid, methyl ester Methyl thioglycolate (0.97 ml) was added dropwise to a stirred suspension of sodium hydride (0.434 g, 60% dispersion in oil) in dimethylformamide (30 ml). The mixture was stirred at room temperature for 1 hour. 13 ml of this solution was added to a solution of the product from step (i) (0.9 g) in dimethylformamide (20 ml). The mixture was stirred for 2 hours then quenched with aqueous arnmonium chloride and partitioned between ethyl acetate and water. The organic phase was dried (MgSO$_4$) and evaporated. The residue was purified by chromatography eluting with 50% ethyl acetate in isohexane. Yield 1.0 g.

1H NMR: δ (DMSO) 11.63(s,1H), 7.81(s,2H), 7.61–7.27 (m,8H), 7.14(s,1H), 6.97(s,2H), 5.45(s,1H), 4.22(s,2H), 3.67(s,3H).

iii) 2-[[6-[5-{5H-Dibenzo[a,d]cyclohepten-5-yl}-3,4-dihydro-2-oxo-4-thioxo-1(2H)-pyrimidinyl]pyridazin-3-yl]thio]acetic acid, methyl ester The subtitle compound was prepared from the product of step (ii) (0.99 g) by the method of example 1 step (vi). Purification was by chromatography eluting with 30–40% ethyl acetate in isohexane. Yield 0.5 g.

MS: APCI(+ve): 501 (M+1, 100%).

iv) 2-[[6-[5-{5H-Dibenzo[a,d]cyclohepten-5-yl}-3,4-dihydro-2-oxo-4-thioxo-1(2H)-pyrimidinyl]pyridazin-3-yl]thio]acetic acid The title compound was prepared from the product of step (iii) (0.49 g) by the method of example 1 step (vii). Yield 0.345 g.

MS: APCI(+ve): 487 (M+1, 100%); 1H NMR: δ (DMSO) 12.96(s,1H), 7.83(s,2H), 7.68(d,2H), 7.54(s,1H), 7.43–7.27 (m,6H), 7.01(s,2H), 5.98(s,1H), 4.16(s,2H). MP:248–250° C.

EXAMPLE 3

5-[5H-Dibenzo[a,d]cyclohepten-5-yl]-1-[6-[[5-[trifluoromethyl-1,2,4-triazol-3-yl]thio]pyridazin-3-yl]-2,4(1H,3H)-pyrimidinedione A solution of 5-[trifluoromethyl]-4H-1,2,4-triazole-3 (2H)-thione (1.6 g) in dimethylformamide (10 ml) was added to a stirred suspension of sodium hydride (0.336 g, 60% dispersion in oil) in dimethylformamide (20 ml). The mixture was stirred for 1.5 hours. 25 ml of this solution were added to a solution of the product from example 2 step (i) (0.87 g) in dimethylformamide (20 ml). After 4 hours at room temperature the mixture was heated at 100° C. for 16 hours. The mixture was partitioned between ethyl acetate and water. The organic phase was dried (MgSO$_4$) and evaporated. The residue was purified by chromatography eluting with 5–10% methanol in chloroform. Yield 0.4 g.

MS: APCI(+ve): 548 (M+1, 100%); 1H NMR: δ (DMSO) 11.67(s,1H), 7.98(d,1H), 7.88(d,1H), 7.60–7.27(m,8H), 7.22 (s,1H), 6.97(s,2H), 5.45(s,1H). MP: 160° C.

EXAMPLE 4

5-[5H-Dibenzo[a,d]cyclohepten-5-yl]-3,4-dihydro-4-thioxo-1-[6-[[5-[trifluoromethyl]-1,2,4-triazol-3-yl]thio]pyridazin-3-yl]-2(1H)-pyrimidinone The title compound was prepared from example 3 (1.0 g) by the method of example 1 step (vi). Yield 0.02 g.

MS: APCI(+ve): 564 (M+1, 100%); 1H NMR: δ (DMSO) 12.99(s,1H), 8.02(d,1H), 7.89(d,1H), 7.66–7.62(m,3H), 7.45–7.26(m,6H), 7.00(s,2H), 5.97(s,1H). MP:165° C.

EXAMPLE 5

4-[2-[5-{5H-Dibenzo[a,d]cyclohepten-5-yl}-3,4-dihydro-2-oxo-4-thioxo-1(2H)-pyrimidinyl]-4-[carboxymethylthio]pyrimidin-5-yl]phenylacetic acid i) 4-[Tributylstannyl]phenylacetic acid, methyl ester A mixture of 4-bromophenylacetic acid methyl ester (1.97 g) (J.Org.Chem. 1994, 59, 6095), hexabutylditin (5.0 g) and tetrakis(triphenylphosphine)palladium (0) (0.46 g) in toluene (60 ml) was heated at reflux for 18 hours. The mixture was partitioned between ethyl acetate and aqueous ammonia. The organic phase was dried (MgSO$_4$) and evaporated. Purification was by chromatography eluting with 2–4% ethyl acetate in isohexane. Yield 1.21.g.

1H NMR: δ (CDCl$_3$) 7.42(d,2H), 7.24(d,2H), 3.70(s,3H), 3.61(s,2H), 1.61–0.86(m,27H).

ii) 4-[2,4-Bis-[1,1-dimethylethoxy]pyrimidin-5-yl]phenylacetic acid, methyl ester A mixture of the product of example 1 step (iii) (0.91 g) tetrakis(triphenylphosphine)palladium (0) (0.2 g) and the product from step (i) (0.75 g) in toluene (25 ml) was heated at reflux for 18 hours. The mixture was partitioned between diethyl ether and aqueous ammonia. The organic phase was dried (MgSO$_4$) and evaporated. Purification was by chromatography eluting with 10% ethyl acetate in isohexane. Yield 0.35 g.

1H NMR: δ (CDCl$_3$) 8.21(s,1H), 7.46(dt,2H), 7.30(d,2H), 3.72(s,3H), 3.66(s,2H).

iii) 4-[2,4-Dichloropyrimidin-5-yl]phenylacetic acid, methyl ester

Trifluoroacetic acid (1 ml) was added to a solution of the product from step (ii) (1.13 g) in dichloromethane (20 ml) at room temperature. After 3 hours the mixture was evaporated and the residue heated at reflux with phosphorous oxychloride (30 ml) and N,N-dimethylaniline (0.38 ml) for 14 hours. The solvent was evaporated and the residue partitioned between ethyl acetate and aqueous sodium bicarbonate. The organic phase was dried (MgSO$_4$) and evaporated. Purification was by chromatography eluting with 20% ethyl acetate in isohexane. Yield 0.61 g.

MS: GC-MS: 296/8/300 (M+1).

iv) 4-[2-Chloro-4-[methoxycarbonylmethylthio]pyrimidin-5-yl]phenylacetic acid, methyl ester Methyl thioglycolate (0.18 ml) was added to a solution of the product from step (iii) (0.6 g) and triethylamine (0.56 ml) in tetrahydrofuran (10 ml) at room temperature. The mixture was stirred for 4 hours and partitioned between ethyl acetate and water. The organic phase was dried (MgSO$_4$) and evaporated. Purification was by chromatography eluting with 20–30% ethyl acetate in isohexane. Yield 0.7 g.

MS: APCI(+ve): 367/9 (M+1).

v) 4-[2-[5-{5H-Dibenzo[a,d]cyclohepten-5-yl}-3,4-dihydro-2,4-dioxo-1(2H)-pyrimidinyl]-4-[methoxycarbonylmethylthio]pyrimidin-5-yl]phenylacetic acid, methyl ester The subtitle compound was prepared from the product of step (iv) (0.58 g) and the product of example 1 step (iv) (0.48 g) by the method of example 2 step (i). Purification was by chromatography eluting with 2% methanol in chloroform. Yield 0.4 g.

MS: APCI(+ve): 633 (M+1, 100%).

vi) 4-[2-[5-{5H-Dibenzo[a,d]cyclohepten-5-yl}-3,4-dihydro-2-oxo-4-thioxo-1(2H)-pyrimidinyl]-4-[metboxycarbonylmethylthio]pyrimidin-5-yl]phenylacetic acid, methyl ester The subtitle compound was prepared from the product of step (v) (0.32 g) by the method of example 1 step (vi). Purification was by chromatography eluting with 30% ethyl acetate in isohexane. Yield 0.21 g.

MS: APCI(+ve): 649 (M+1).

vii) 4-[2-[5-{5H-Dibenzo[a,d]cyclohepten-5-yl}-3,4-dihydro-2-oxo-4-thioxo-1(2H)-pyrimidinyl]-4-[carboxymethylthio]pyrimidin-5-yl]phenylacetic acid The title compound was prepared from the product of step (vi) (0.2 g) by the method of example 1 step (vii). Yield 0.11 g.

MS: APCI(+ve): 621 (M+1); 1H NMR: δ (DMSO) 12.90 (s,1H), 12.70(br s,1H), 8.50(s,1H), 7.67–7.27(m,13H), 7.08 (s,2H), 5.96(s,1H), 4.03(s,2H), 3.68(s,2H). MP:280° C.

EXAMPLE 6

2-[[4-[5-{5H-Dibenzo[a,d]cyclohepten-5-yl}-3,4-dihydro-2-oxo-4-thioxo-1(2H)-pyrimidinyl]pyrimidin-2-yl]thio]acetic acid i) 1-[2-Chloropyrimidin-4-yl]-5-[5H-dibenzo[a,d]cyclohepten-5-yl]-2,4(1H,3H)-pyrimidinedione A mixture of 2,4-dichloropyrimidine (1.49 g), cesium carbonate (3.26 g) and the product of example 1 step (iv) (3 g) in dimethylsulphoxide (40 ml) was stirred at room temperature for 3 hours and partitioned between ethyl acetate and water. The organic phase was dried (MgSO$_4$) and evaporated. The product was collected after trituration with 50% ethyl acetate in isohexane. Yield 2.55 g.

MS: APCI(+ve): 415/7 (M+1).

ii) 2-[[4-[5-{5H-Dibenzo[a,d]cyclohepten-5-yl}-3,4-dihydro-2,4-dioxo-1(2H)-pyrimidinyl]pyrimidin-2-yl]thiolacetic acid, methyl ester A mixture of the product from step (i) (0.52 g), methyl thioglycolate (0.18 ml) and triethylamine (0.42 ml) in tetrahydrofiuran (10 ml) was heated at reflux for 24 hours. The mixture was partitioned between ethyl acetate and 2N HCl. The organic phase was dried (MgSO$_4$) and evaporated. Purification was by chromatography eluting with 40% ethyl acetate in isohexane. Yield 0.42 g.

MS: APCI(+ve): 485 (M+1, 100%).

iii) 2-[[4-{5-{5H-Dibenzo[a,b]cyclohepten-5-yl}-3,4-dihydro-2-oxo-4-thioxo-1(2H)-pyrimidinyl]pyrimidin-2-yl]thiolacetic acid, methyl ester The subtitle compound was prepared from the product of step (ii) (0.41 g) by the method of example 1 step (vi). Purification was by chromatography eluting with 30% ethyl acetate in isohexane. Yield 0.21 g.

1H NMR: δ (DMSO) 12.93(s,1H), 8.67(d,1H), 8.01(s, 1H), 7.80(d,1H), 7.67–7.29(m,8H), 7.04(s,2H), 5.95(s,1H), 4.03(s,2H), 3.63(s,3H).

iv) 2-[[4-[5-{5H-Dibenzo[a,d]cyclohepten-5-yl}-3,4-dihydro-2-oxo-4-thioxo-1(2H)-pyrimidinyl]pyrimidin-2-yl]thiolacetic acid The title compound was prepared from the product of step (iii) (0.2 g) by the method of example 1 step (vii). Purification was by chromatography eluting with 5% methanol in chloroform. Yield 0.05 g.

MS: APCI(+ve): 487 (M+1, 100%); 1H NMR: δ (DMSO) 12.94(br s,2H), 8.67(d,1H), 8.00(s,1H), 7.77(d,1H), 7.65(d, 2H), 7.45–7.29(m,6H), 7.06(s,2H), 5.95(s,1H), 3.98(s,2H). MP:190° C.

EXAMPLE 7

N-[4-[5-{5H-Dibenzo[a,d]cyclohepten-5-yl}-3,4-dihydro-2-oxo-4-thioxo-1(2H)-pyrimidinyl]pyrimidin-2-yl]glycine i) N-[4-[5-{5H-Dibenzo[a,d]cyclohepten-5-yl}-3,4-dihydro-2,4-dioxo-1(2H)-pyrimidinyl]pyrimidin-2-yl]glycine, methyl ester A mixture of the product from example 6 step (i) (1 g), glycine methyl ester hydrochloride (0.339 g) and N,N-diisopropylethylamine (1.13 ml) in 1-methyl-2-pyrrolidinone (20 ml) was heated at 90° C. for 7 hours. The mixture was partitioned between ethyl acetate and water. The organic phase was washed with water, dried (MgSO₄) and evaporated. The residue was dissolved in methanol/chloroform and the product precipitated by the addition of 50% ethyl acetate in isohexane. Yield 0.96 g.

1H NMR: δ (DMSO) 11.49(s.1H), 8.31(d,1H), 7.72–6.96 (m,12H), 5.76(s,1H), 3.98(br s,2H), 3.71 (br s,3H).

ii) N-[4-[5-{5H-Dibenzo[a,d]cyclohepten-5-yl}-3,4-dihydro-2-oxo-4-thioxo-1(2H)-pyrimidinyl]pyrimidin-2-yl]glycine, methyl ester The subtitle compound was prepared from the product of step (i) (0.955 g) by the method of example 1 step (vi). Purification was by chromatography eluting with 50–60% ethyl acetate in isohexane. Yield 0.77 g.

1H NMR: δ (DMSO) 12.82(s,1H), 8.35(d,1H), 7.90–7.00 (m,12H), 5.95(s,1H), 4.04(br s,2H), 3.68(br s,3H).

iii) N-[4-[5-{5H-Dibenzo[a,d]cyclohepten-5-yl}-3,4-dihydro-2-oxo-4-thioxo-1(2H)-pyrimidinyl]pyrimidin-2-yl]glycine The title compound was prepared from the product of step (ii) (0.85 g) by the method of example 1 step (vii). Yield 0.63 g.

MS: APCI(+ve): 470 (M+1, 100%); 1H NMR: δ (DMSO) 12.82(s,1H), 8.34(d,1H), 7.88(br s,1H), 7.63(d,2H), 7.45–7.28(m,6H), 7.15(d,1H), 7.04(brs,2H), 5.96(s,1H), 3.98(d,2H). (Rotamers) MP:208° C.

EXAMPLE 8

N-[4-[5-{2,8-Dimethyl-5H-dibenzo[a,d]cyclohepten-5-yl}-3,4-dihydro-2,4-dioxo-1(2H)-pyrimidinyl]pyrimidin-2-yl]glycine i) 5-[2,8-Dimethyl-5H-dibenzo[a,d]cyclohepten-5-yl]-2,4 (1H,3H)-pyrimidinedione n-Butyllithium (5.6 ml of a 2.5M solution in hexanes) was added dropwise to a solution of the product of example 1 step (iii) (3.85 g) in tetrahydrofuran (30 ml) at −78° C. The solution was stirred for 30 minutes and a solution of 10,11-dihydro-2,8-dimethyl-5H-dibenzo[a,d]cyclohepten-5-one (European Patent, 1993, 0 589 322 A1) (3.0 g) in tetrahydrofuran (20 ml) was added. The mixture was stirred at −78° C. for 45 minutes and room temperature for 15 minutes and then partitioned between brine and ethyl acetate. The organic phase was dried (MgSO₄) and evaporated. The residue was dissolved in glacial acetic acid (100 ml) and heated at 120° C. for 30 minutes. The solvent was evaporated and the residue azeotroped with toluene and triturated with diethyl ether to give a solid. Yield 4.03 g.

MS: APCI(+ve): 331 (M+1, 100%).

ii) 1-[2-Chloropyrimidin-4-yl]-5-[2,8-dimethyl-5H-dibenzo[a,d]cyclohepten-5-yl]-2,4(1H,3H)-pyrimidinedione The subtitle compound was prepared from the product of step (i) (4.0 g) by the method of example 6 step (i). Purification was by chromatography eluting with 50% ethyl acetate in isohexane. Yield 3.2 g.

1H NMR: δ (DMSO) 11.66(s,1H), 8.74(d,1H), 8.07(d, 1H), 7.72(s,1H), 7.44(d,2H), 7.21–7.18(m,4H), 6.91(s,2H), 5.35(s,1H), 2.29(s,6H).

iii) N-[4-[5-[2,8-Dimethyl-5H-dibenzo[a,d]cyclohepten-5-yl}-3,4-dihydro-2,4-dioxo-1(2H)-pyrimidinyl]pyrimidin-2-yl]glycine, methyl ester The subtitle compound was prepared from the product of step (ii) (0.5 g) by the method of example 7 step (i). Yield 0.3 g. Used directly in the next step.

iv) N-[4-[5-{2,8-Dimethyl-5H-dibenzo[a,d]cyclohepten-5-yl}-3,4-dihydro-2,4-dioxo-1(2H)-pyrimidinyl]pyrimidin-2-yl]glycine The title compound was prepared from the product of step (iii) (0.1 g) by the method of example 1 step (vii). Yield 0.09 g.

MS: APCI(+ve): 482 (M+1); 1H NMR: δ (DMSO) 11.50 (s,1H), 8.32(d,1H), 7.70(br s,1H), 7.60(br s,1H), 7.40(d,2H), 7.20(d+s,4H), 7.0(br s,1H), 6.9(s,2H), 5.33(s,1H), 5.10(br s,2H), 2.30(s,6H). (Rotamers) MP:260–263° C.

EXAMPLE 9

N-[4-[5-{2,8-Dimethyl-5H-dibenzo[a,d]cyclohepten-5-yl}-3,4-dihydro-2-oxo-4-thioxo-1(2H)-pyrimidinyl]pyrimidin-2-yl]glycine i) N-[4-[5-{2,8-Dimethyl-5H-dibenzo[a,d]cyclohepten-5-yl}-3,4-dihydro-2-oxo-4-thioxo-1(2H)-pyrimidinyl]pyrimidin-2-yl]glycine, methyl ester The subtitle compound was prepared from the product of example 8 step (iii) (0.2 g) by the method of example 1 step (vi). Purification was by chromatography eluting with 30–50% ethyl acetate in isohexane. Yield 0.11 g.

MS: APCI(+ve): 512 (M+1, 100%).

ii) N-[4-[5-{2,8-Dimethyl-5H-dibenzo[a,d]cyclohepten-5-yl}-3,4-dihydro-2-oxo-4-thioxo-1(2H)-pyrimidinyl]pyrimidin-2-yl]glycine The title compound was prepared from the product of step (i) (0.1 g) by the method of example 1 step (vii). Yield 0.02 g.

MS: APCI(+ve): 498 (M+1, 100%); 1H NMR: δ (DMSO) 12.83(s,1H), 8.35(d,1H), 7.92–6.94(m,8H), 5.89(s,1H), 4.00 (s,2H), 2.29(s,6H). MP:205° C.

EXAMPLE 10

2-[2-[[4-[5-{2,8-Dimethyl-5H-dibenzo[a,d]
cyclohepten-5-yl}-3,4-dihydro-2,4-dioxo-1(2H)-
pyrimidinyl]pyrimidin-2-yl]amino]acetylamino]-4-
thiazoleacetic acid i) 2-[[2-aminoacetyl]amino]-4-thiazoleacetic acid, ethyl ester A mixture of N-(tert-butoxycarbonyl)glycine (3.1 g), 2-amino-4-thiazoleacetic acid ethyl ester (3 g) and bromo-tris(pyrrolidino)-phosphonium hexafluorophosphate (7.54 g) in dimethylformamide (20 ml) was treated with N,N-diisopropylethylamine (6 ml). After 25 minutes N,N-dimethyl-4-aminopyridine (1.96 g) was added. After 24 hours the mixture was partitioned between ethyl acetate and brine. The organic phase was washed with saturated aqueous sodium bicarbonate, brine, 1N HCl and brine, dried ($MgSO_4$) and evaporated. The residue was purified by chromatography eluting with 50% ethyl acetate in isohexane. The product (0.77 g) was dissolved in dichloromethane (25 ml) and trifluoroacetic acid (10 ml). After 2 hours the mixture was evaporated. The residue was partitioned between ethyl acetate and sodium bicarbonate solution. The aqueous phase was repeatedly extracted with ethyl acetate. The combined extracts were dried ($MgSO_4$) and evaporated. Yield 0.41 g.

MS: APCI(+ve): 244 M+1).

ii) 2-[2-[[4-[5-{2,8-Dimethyl-5H-dibenzo[a,d]cyclohepten-5-yl}-3,4-dihydro-2,4-dioxo-1(2H)-pyrimidinyl]pyrimidin-2-yl]amino]acetylamino]-4-thiazoleacetic acid, ethyl ester A mixture of the product from step (i) (0.194 g), N,N-diisopropylethylamine (0.35 ml) and the product from example 8 step (ii) (0.25 g) in 1-methyl-2-pyrrolidinone (5 ml) was heated at 90° C. for 10 hours. The mixture was partitioned between ethyl acetate and water. The organic phase was washed with water, dried ($MgSO_4$) and evaporated. Purification was by chromatography eluting with 70% ethyl acetate in isohexane. Yield 0.175 g.

MS: APCI(+ve): 650 (M+1).

iii) 2-[2-[[4-[5-{2,8-Dimethyl-5H-dibenzo[a,d]cyclohepten-5-yl}-3,4-dihydro-2,4-dioxo-1(2H)-pyrimidinyl]pyrimidin-2-yl]amino]acetylamino]-4-thiazoleacetic acid The title compound was prepared from the product of step (ii) (0.1 75 g) by the method of example 1 step (vii). Yield 0.03 g.

MS: APCI(+ve): 622 (M+1, 100%); 1H NMR: δ (DMSO) 12.52(br s,1H), 12.38(br s,1H), 11.49(s,1H), 8.31(d,1H), 7.57–6.87(m,11H), 5.32(s,1H), 4.22(d,1H), 3.64(s,2H), 2.21 (br s,6H). (Rotamers). MP:223° C.

EXAMPLE 11

N-[4-[5-{5H-Dibenzo[a,d]cyclohepten-5-yl}-3,4-
dihydro-2,4-dioxo-1(2H)-pyrimidinyl]pyrimidin-2-
yl]-L-proline i) N-[4-[5-{5H-Dibenzo[a,d]cyclohepten-5-yl}-3,4-dihydro-2,4-dioxo-1(2H)-pyrimidinyl]pyrimidin-2-yl]-L-proline, methyl ester The subtitle compound was prepared from the product of example 6 step (i) (0.3 g) and L-proline methyl ester hydrochloride (0.6 g) by the method of example 10 step (ii). Purification was by chromatography eluting with 5% methanol in dichloromethane. Yield 0.55 g.

MS: APCI(+ve): 508 (M+1).

ii) N-[4-[5-{5H-Dibenzo[a,d]cyclohepten-5-yl}-3,4-dihydro-2,4-dioxo-1(2H)-pyrimidinyl]pyrimidin-2-yl]-L-proline The title compound was prepared from the product of step (i) (0.55 g) by the method of example 1 step (vii) Yield 0.1 87 g.

MS: APCI(+ve): 494 (M+1); 1H NMR: δ (DMSO) 12.49 (br s,1H), 11.48(s,1H), 8.30(d,1H), 7.87(s, 1H), 7.6–7.62(m, 2H), 7.28–7.42(m, 7H), 6.99(s, 2H), 5.44(s, 1H), 4.4–4.44 (m, 1H), 3.27–3.37(m, 2H), 2.3–2.37(m, 1H), 2.0–2.07(m, 3H) MP: 190–200° C.

EXAMPLE 12

N-[4-[-5-{2,8-Dimethyl-5H-dibenzo[a,d]
cyclohepten-5-yl}-3,4-dihydro-2,4-dioxo-1(2H)-
pyrimidinyl]pyrimidin-2-yl]-L-proline i) N-{4-[5-{2,8-Dimethyl-5H-dibenzo[a,d]cyclohepten-5-yl)-3,4-dihydro-2,4-dioxo-1(2H)-pyrimidinyl]pyrimidin-2-yl]-L-proline, methyl ester The subtitle compound was prepared from the product of example 8 step (ii) (0.3 g) and L-proline methyl ester hydrochloride (0.56 g) by the method of example 10 step (ii). Purification was by chromatography eluting with 5% methanol in chloroform. Yield 0.3 g.

MS: APCI(+ve): 536 (M+1, 100%).

ii) N-[4-[5-{2,8-Dimethyl-5H-dibenzo[a,d]cyclohepten-5-yl}-3,4-dihydro-2,4-dioxo-1(2H)-pyrimidinyl]pyrimidin-2-yl]-L-proline The title compound was prepared from the product of step (i) (0.3 g) by the method of example 1 step (vii). Yield 0.105 g.

MS: APCI(+ve): 522 (M+1, 100%); 1H NMR: δ (DMSO) 8.30(d,1H), 7.87(s,1H), 7.45(d,2H), 7.32(d,1H), 7.22–7.18 (m,3H), 6.89(s,2H), 5.33(s,1H), 4.42(m,1H), 3.36 (m,3H), 2.35(m,1H), 2.29(s,6H), 2.04–2.07(m,3H). MP:200–205° C.

EXAMPLE 13

(2S-trans)-N-[4-[5-{2,8-Dimethyl-5H-dibenzo[a,d]
cyclohepten-5-yl}-3,4-dihydro-2,4-dioxo-1(2H)-
pyrimidinyl]pyrimidin-2-yl}-4-hydroxy-2-
pyrrolidinecarboxylic acid i) (2S-trans)-N-[4-[5-{2,8-Dimethyl-5H-dibenzo[a,d]cyclohepten-5-yl}-3,4-dihydro-2,4-dioxo-1(2H)-pyrimidinyl]pyrimidin-2-yl]-4-hydroxy-2-pyrrolidinecarboxylic acid, phenylmethyl ester The subtitle compound was prepared from trans-4-hydroxy-L-proline benzyl ester hydrochloride (0.928 g) and the product of example 8 step (ii) (0.3 g) by the method of example 10 step (ii). Purification was by chromatography eluting with 50–60% ethyl acetate in isohexane. Yield 0.29 g.

MS: APCI(+ve): 429 (M+1).

ii) (2S-trans)-N-[4-15-{2,8-Dimethyl-5H-dibenzo[a,d]cyclohepten-5-yl}-3,4-dihydro-2,4-dioxo-1(2H)-pyrimidinyl]pyrimidin-2-yl}-4-hydroxy-2-pyrrolidinecarboxylic acid The title compound was prepared from the product of step (i) (0.28 g) by the method of example 1 step (vii). Yield 0.05 g.

MS: APCI(+ve): 538 (M+1); 1H NMR: δ (DMSO) 11.46 (s,1H), 8.30(d,1H), 7.87(s,1H), 7.45(d,2H), 7.32(d,1H), 7.22–7.15(m,4H), 6.91(s,2H), 5.34(s,1H), 4.50(brs,1H), 4.43(t,1H), 3.49(dd,1H), 3.41–3.37(m,1H), 2.30(s,6H), 2.31–2.00(m,1H), 2.16–2.07(m,1H). MP:208–210° C.

EXAMPLE 14

N$^\alpha$-[4-[5-{2,8-Dimethyl-5H-dibenzo[a,d]
cyclohepten-5-yl}-3,4-dihydro-2,4-dioxo-1(2H)-
pyrimidinyl]pyrimidin-2-yl]-L-histidine i) N$^\alpha$-[4-[5-{2,8-Dimethyl-5H-dibenzo[a,d]cyclohepten-5-yl}-3,4-dihydro-2,4-dioxo-1(2H)-pyrimidinyl]pyrimidin-2-yl]-L-histidine, methyl ester The subtitle compound was prepared from L-histidine methyl ester dihydrochloride (1.15 g) and the product of example 8 step (ii) (0.7 g) by the method of example 10 step (ii). Purification was by chromatography eluting with 5–10% methanol in dichloromethane. Yield 0.25 g.

MS: APCI(+ve): 576 (M+1).

ii) N$^\alpha$-[4-[5-{2,8-Dimethyl-5H-dibenzo[a,d]cyclohepten-5-yl}-3,4-dihydro-2,4-dioxo-1(2H)-pyrimidinyl]pyrimidin-2-yl]-L-histidine The title compound was prepared from the product of step (i) (0.122 g) by the method of example 1 step (vii). Yield 0.025 g.

MS: APCI(+ve): 562 (M+1); 1H NMR: δ (DMSO,90° C.) 11.19(s,1H), 8.26(d,1H), 7.80(s,1H), 7.65(s,1H), 7.39(m, 2H), 7.19–7.12(m,6H), 6.97–6.83(m,3H), 5.31(s,1H), 4.60 (m,1H), 3.12(s,2H), 2.28(s,6H). MP:223° C.

EXAMPLE 15

(±)-2-[2-[[4-[5-{2-Ethyl-8-methyl-5H-dibenzo[a,d]cyclohepten-5-yl}-3,4-dihydro-2,4-dioxo-1(2H)-pyrimidinyl]pyrimidin-2-yl amino]acetylamino]-4-thiazoleacetic acid i) 3-Ethylphenylmethanol n-Butyllithium (34 ml of a 2.5M solution in hexanes) was added to a solution of 1-bromo-3-ethylbenzene (15 g) in tetrahydrofuiran (320 ml) at −78° C. After 1 hour dimethylformamide (15 ml) was added. The mixture was stirred at −78° C. for 1 hour and allowed to warm to room temperature. The mixture was quenched with aqueous ammonium chloride and partitioned between ethyl acetate and water. The organic phase was dried (MgSO$_4$) and evaporated. The residue was dissolved in methanol (250 ml) and treated with sodium borohydride (1.51 g) portionwise. The mixture was stirred at room temperature for 16 hours, quenched with 2M HCl (100 ml) and stirred for 4 hours. The mixture was concentrated under reduced pressure and the residue partitioned between ethyl acetate and 2M HCl. The organic phase was dried (MgSO$_4$), evaporated and the residue purified by chromatography eluting with 5–10% ethyl acetate in isohexane. Yield 7.6 g.

MS: GC-MS: 136 (M$^+$) 97%.

ii) 1-Bromomethyl-3-ethylbenzene

Phosphorous tribromide (5.3 ml) was added to a solution of the product from step (i) (7.6 g) in benzene (150 ml) at 0° C. After 3 hours, water (40 ml) was added and the mixture warmed to room temperature and extracted with ethyl acetate. The organic phase was dried (MgSO$_4$) and evaporated. Purified by chromatography eluting with 2% ethyl acetate in isohexane. Yield 8.0 g.

1H NMR: δ (CDCl$_3$) 7.28–7.12(m,4H), 4.48(s,2H), 2.65 (q,2H), 1.24(t,3H).

iii) 2-[2,4-Dimethylphenyl]-4,5-dihydro-4,4-dimethyloxazole

Dimethylformamide (8 drops) was added to a stirred suspension of 2,4-dimethylbenzoic acid (80 g) in thionyl chloride (400 ml) and the mixture was stirred overnight at room temperature. The solution was heated at 80° C. for 3 hours and the thionyl chloride evaporated. The residue was dissolved in dichloromethane (200 ml) and added dropwise to a solution of 2-amino-2-methyl-propan-1-ol (124 ml) in dichloromethane (400 ml). The mixture was stirred overnight, washed with 2M HCl, water, aqueous sodium bicarbonate and water. The organic phase was dried (MgSO$_4$) and evaporated. The residue was dissolved in dichloromethane (800 ml) and treated with thionyl chloride (125 ml) dropwise at 0° C. The mixture was stirred at room temperature for 2 hours and evaporated. The solid residue was partitioned between ethyl acetate and aqueous sodium bicarbonate. The organic phase was washed with water, dried (MgSO$_4$) and evaporated. Yield 69 g.

1H NMR: δ (CDCl$_3$) 7.64(d,1 H), 7.02–6.99(m,2H), 4.04(s,2H), 2.52(s,3H), 2.32(s,3H), 1.38(s,6H).

iv) 2-[2-[2-[3-Ethylphenyl]ethyl]-4-methylphenyl]-4,5-dihydro-4,4-dimethyloxazole n-Butyllithium (16.8 ml of a 2.5M solution in isohexane) was added dropwise to a stirred solution of the product of step (iii) (8.13 g) in dry tetrahydrofuran (ISOml) at 0° C. under nitrogen. After 1 hour, the product of step (ii) (8.0 g) in tetrahydrofliran (60 ml) was added. After 1 hour, the reaction was quenched with aqueous ammonium chloride and partitioned between ethyl acetate and water. The organic solution was dried (MgSO$_4$) and evaporated. Purification was by chromatography eluting with 5% ethyl acetate in isohexane. Yield 4.93 g.

MS: APCI+: 322 (M+1).

v) 2-[2-[3-Ethylphenyl]ethyl]-4-methylbenzoic acid

The product of step (iv) (4.9 g) and methyl iodide (4.7 ml) in acetonitrile (150 ml) was heated under reflux for 6 hours. The solution was evaporated and the residue and sodium hydroxide (8 g) was refluxed in water (40 ml) and methanol (50 ml). After 6 hours the methanol was evaporated and the residue was partitioned between ethyl acetate and 2M hydrochloric acid. The organic solution was dried (MgSO$_4$) and evaporated. Used directly in the next step.

vi) 2-Ethyl-10,11-dihydro-8-methyl-5H-dibenzo[a,d]cyclohepten-5-one

A mixture of the product from step (v) in polyphosphoric acid (40 g) and sulpholane (20 ml) was heated at 130° C. for 5 hours and partitioned between ethyl acetate and water. The organic phase was washed with aqueous sodium bicarbonate and water, dried (MgSO$_4$) and evaporated. Purified by chromatography eluting with 5% ethyl acetate in isohexane.

MS: GC-MS: 250 (M$^+$).

vii) (±)-5[-2-Ethyl-8-methyl-5H-dibenzo[a,d]cyclohepten-5-yl]-2,4(1H,3H)-pyrimidinedione The subtitle compound was prepared from the product of step (vi) (3 g) by the method of example 8 step (i). Yield 1.48 g.

MS: LC-MS: APCI(+ve): 345 (M+1, 100%).

viii) (±)-1-[2-Chloropyrimidin-4-yl]-[5-[2-ethyl-8-methyl-5H-dibenzo[a,d]cyclohepten-5-yl]-2,4(1H,3H)-pyrimidinedione The subtitle compound was prepared from the product of step (vii) (0.44 g) by the method of example 6 step (i). Yield 0.42 g.

1H NMR: δ (DMSO) 11.66(s,1H), 8.74(d,1H), 8.08(d, 1H), 7.73(s,1H), 7.48–7.43(m,2H), 7.24–7.19(m,4H), 6.92 (s,2H), 5.36(s,1H), 2.60(q,2H), 2.29(s,3H), 1.17(t,3H).

ix) (±)-2-[2-[[4-[5-{2-Ethyl-8-methyl-5H-dibenzo[a,d]cyclohepten-5-yl}-3,4-dihydro-2,4-dioxo-1(2H)-pyrimidinyl]pyrimidin-2-yl]amino]acetylamino]-4-thiazoleacetic acid, ethyl ester The subtitle compound was prepared from the products of step (viii) (0.415 g) and example 10 step (i) (1 g) by the method of example 10 step (ii). Purification was by chromatography eluting with 70–80% ethyl acetate in isohexane. Yield 0.22 g.

MS: APCI(+ve): 664 (M+1, 100%).

x) (±)-2-[2-[[4-[5-{2-Ethyl-8-methyl-5H-dibenzo [a,d]cyclohepten-5-yl}-3,4-dihydro-2,4-dioxo-1(2H)-pyrimidinyl]pyrimidin-2-yl]amino]acetylamino]-4-thiazoleacetic acid The title compound was prepared from the product of step (ix) (0.21 g) by the method of example 1 step (vii), Yield 0.12 g.

MS: APCI(+ve): 636 (M+1, 100%); 1H NMR: δ (DMS0) 12.50(br s,1H), 12.37(s,1H), 11.48(s,1H), 8.31(d,1H), 7.59 (s,1H), 7.45–6.88(m,11H), 5.33(s,1H), 4.22(d,2H), 3.64(s, 2H), 2.53(br s,2H), 2.22(br s,3H), 1.17(br s,3H). MP:217° C.

EXAMPLE 16

2-[2-[[2-[Dimethylamino]-4-[5-{2,8-dimethyl-5H-dibenzo[a,d]cyclohepten-5-yl}-3,4-dihydro-2,4-dioxo-1(2H)-pyrimidinyl]pyrimidin-6-yl]amino] acetylamino]-4-thiazoleacetic acid i) 1-[2,6-Dichloropyrimidin-4-yl]-5-[2,8-dimethyl-5H-dibenzo[a,d]cyclohepten-5-yl]-2,4(1H,3H)-pyrimidinedione Cesium carbonate (5 g) was added to a solution of the product of example 8 step (i) (5 g) in 1-methyl-2-pyrrolidinone (50 ml). After 5 minutes 2,4,6-trichloropyrimidine (2.8 g) was added. After 2 hours the reaction was partitioned between brine and ethyl acetate. The organic phase was washed with water, dried (MgSO$_4$) and evaporated under reduced pressure. Purification was by chromatography eluting with 30% ethyl acetate in toluene. Yield 2.9 g.

MS: APCI(+ve): 477 (M+1).

ii) 2-[2-[[2-Chloro-4-[5-{2,8-dimethyl-5H-dibenzo[a,d]cyclohepten-5-yl}-3,4-dihydro-2,4-dioxo-1(2H)-pyrimidinyl]pyrimidin-6-yl]amino]acetylamino]-4-thiazoleacetic acid, ethyl ester A mixture of the product of step (i) (1.5 g), the product of example 10 step (i) (1.13 g) and N,N-diisopropylethylaminie (0.6 ml) in 1-methyl-2-pyrrolidinone (30 ml) was heated at 50° C. for 14 hours then 80° C. for 4 hours. The reaction mixture was partitioned between brine containing dilute HCl and ethyl acetate. The organic phase was washed with water, dried (MgSO$_4$) and evaporated under reduced pressure. Purification was by chromatography eluting with 50% ethyl acetate in isohexane. Yield 0.43 g.

MS: APCI(+ve): 684 (M+1).

iii) 2-[2-[[2-[Dimethylamino]-4-[5-{2,8-dimethyl-5H-dibenzo[a,d]cyclohepten-5-yl}-3,4-dihydro-2,4-dioxo-1(2H)-pyrimidinyl]pyrimidin-6-yl]amino]acetylamino]-4-thiazoleacetic acid, ethyl ester A mixture of the product of step (ii) (0.4 g), dimethylamine hydrochloride (0.1 8 g) and N,N-diisopropylethylamine (0.5 ml) in dimethylformamide (5 ml) was heated at 85° C. for 6 hours. The reaction mixture was partitioned between brine containing dilute HCl and ethyl acetate. The organic phase was washed with water, dried (MgSO$_4$) and evaporated under reduced pressure. Purification was by chromatography eluting with ethyl acetate. Yield 0.2 g.

MS: APCI(+ve): 693 M+1).

iv) 2-[2-[[2-[Dimethylamino]-4-[5-{2,8-dimethyl-5H-dibenzo[a,d]cyclohepten-5-yl}-3,4-dihydro-2,4-dioxo-1 (2H)-pyrimidinyl]pyrimidin-6-yl amino]acetylamino]-4-thiazoleacetic acid The title compound was prepared from the product of step (iii) (0.2 g) by the method of example 1 step (vii). Yield 0.15 g.

MS: APCI(+ve): 665 (M+1); 1H NMR: δ (DMSO, at 90° C.) 11.93(br s, 2H), 11.02(br s,1H), 7.42(s, 1H), 7.40(d, 2H), 7.18(m, 4H), 6.93(s, 1H), 6.70(s, 2H), 6.68(t, 1H), 6.33(s, 1H), 5.28(s, 1H), 4.15(d, 2H), 3.62(s, 2H), 2.94(s, 6H), 2.25(s, 6H). MP:220° C.

EXAMPLE 17

N-[2-[5-{2,8-Dimethyl-5H-dibenzo[a,d]cyclohepten-5-yl}-3,4-dihydro-2,4-dioxo-1(2H)-pyrimidinyl]-5-[methoxycarbonyl]pyrimidin-4-yl]glycine i) 2,4-Dichloro-5-pyrimidinecarboxylic acid, methyl ester 1,2,3,4-Tetrahydro-2,4-dioxo-5-pyrimidinecarboxylic acid methyl ester (7.0 g) in phosphorus oxychloride (80 ml) was heated under reflux for 16 hours. The phosphorus oxychloride was removed by evaporation under reduced pressure. The reaction mixture was partitioned between water and ethyl acetate. The organic phase was washed with water, dried (MgSO$_4$) and evaporated under reduced pressure. Purification was by chromatography eluting with 20% ethyl acetate in isohexane. Yield 4.5 g.

1H NMR: δ (DMSO) 9.05(s, 1H), 4.0(s, 3H).

ii) 2-Chloro-4-[[[1,1-dimethylethoxy]carbonylmethyl] amino]-5-pyrimidinecarboxylic acid, methyl ester A mixture of the product of step (i) (1.73 g), glycine tert-butyl ester (1.4 g) and N,N-diisopropylethylamine (2.6 ml) in dimethylformamide (20 ml) was stirred at room temperature. After 4 hours, the reaction mixture was partitioned between 2M HCl and ethyl acetate. The organic phase was washed with water, dried (MgSO$_4$) and evaporated under reduced pressure. Purification was by chromatography eluting with 5% ethyl acetate in toluene. Yield 1.5 g.

MS: APCI(+ve): 302/304 (M+1).

iii) 2-[5-{2,8-Dimethyl-5H-dibenzo[a,d]cyclohepten-5-yl}-3,4-dihydro-2,4-dioxo-1(2H)-pyrimidinyl]-4-[[[1,1-dimethylethoxy]carbonylmethyl]amino]-5-pyrimidinecarboxylic acid, methyl ester A mixture of the product of step (ii) (0.52 g), the product of example 8 step (i) (0.5 g) and cesium carbonate (0.49 g) in dimethylformamide (15 ml) was heated at 70° C. After 3 hours, the reaction mixture was partitioned between 1M HCl and ethyl acetate. The organic phase was washed with water, dried (MgSO$_4$) and evaporated under reduced pressure. Purification was by chromatography eluting with 3% methanol in chloroform. Yield 0.47 g.

MS: APCI(+ve): 596 (M+1).

iv) N-[2-[5-{2,8-Dimethyl-5H-dibenzo[a,d]cyclohepten-5-yl}-3,4-dihydro-2,4-dioxo-1(2H)-pyrimidinyl]-5-[methoxycarbonyl]pyrimidin-4-yl]glycine A mixture of the product of step (iii) (0.57 g) in trifluoroacetic acid (5 ml) and dichloromethane (10 ml) was stirred at room temperature for 5 hours. Methanol (30 ml) was added and the precipitate collected. The solid was dissolved in methanol and sodium hydroxide solution and the product precipitated out by addition of 2M HCl. Yield 0.26 g.

MS: APCI(+ve): 540 (M+1, 100%); 1H NMR: δ (DMSO) 13.02(br s, 1H), 11.39(s, 1H), 8.74(s, 1H), 8.71(t, 1H), 7.42(d, 2H), 7.19–7.17(m, 5H), 6.91(s, 2H), 5.31(s, 1H), 4.15(d, 2H), 3.86(s, 3H), 2.28(s, 6H).

EXAMPLE 18

4-[[Carboxymethyl]amino]-2-[5-{2,8-dimethyl-5H-dibenzo[a,d]cyclohepten-5-yl}-3,4-dihydro-2,4-dioxo-1(2H)-pyrimidinyl]-5-pyrimidinecarboxylic acid The title compound was prepared from the product of example 17 step (iv) (0.23 g) by the method of example 1 step (vii). Yield 0.085 g.

MS: APCI(+ve): 526 (M+1, 100%); 1H NMR: δ (DMSO) 13.34(br s, 1H), 13.00(br s, 1H), 11.38(s, 1H), 8.83(t, 1H), 8.71(s, 1H), 7.42(d, 2H), 7.19–7.15(m, 5H), 6.91(s, 2H), 5.31(s, 1H), 4.16(d, 2H), 2.28(s, 6H). MP:271° C.

EXAMPLE 19

(±)-N-[4-[5-{2-Ethyl-8-methyl-5H-dibenzo[a,d] cyclohepten-5-yl}-3,4-dihydro-2-oxo-4-thioxo-1 (2H)-pyrimidinyl]pyrimidin-2-yl]-N-methylglycine i) N-[4-Fluoropyrimidin-2-yl]-N-methylglycine, methyl ester To a solution of 2,4-difluoropyrimidine (J.Heterocyclic Chem. 1985, 22, 149) (4.48 g) in isohexane (50 ml) at 0° C. was added sarcosine methyl ester hydrochloride (5.39 g) followed by N,N-diisopropylethylamine (13.45 ml). After 5 minutes, the ice bath was removed and the reaction mixture allowed to stir at room temperature for 3 hours. The solvents were evaporated under reduced pressure and the residue purified by chromatography eluting with ethyl acetate/isohexane mixtures. The first and minor component of the mixture to be eluted was the subtitle compound. Yield 0.68 g.

MS: APCI(+ve): 200 (M+1)

ii) (±)-N-[4-[5-{2-Ethyl-8-methyl-5H-dibenzo[a,d] cyclohepten-5-yl}-3,4-dihydro-2,4-dioxo-1(2H)-pyrimidinyl]pyrimidin-2-yl]-N-methylglycine, methyl ester A mixture of the product of step (i) (0.68 g), and the product of example 15 step (vii) (2.35 g) was stirred with cesium carbonate (2.22 g) in 1-methyl-2-pyrrolidinone (20 ml) at 70–80° C. for 4 hours. The reaction mixture was partitioned between ethyl acetate and brine. The organic layer was dried ($MgSO_4$) and evaporated under reduced pressure. The residue was purified by chromatography eluting with ethyl acetate in toluene. Yield 0.57 g.

MS: APCI(+ve) 524 (M+1)

iii) (±)-N-[4-[5-{2-Ethyl-8-methyl-5H-dibenzo[a,d] cyclohepten-5-yl}-3,4-dihydro-2-oxo-4-thioxo-1(2H)-pyrimidinyl]pyrimidin-2-yl]-N-methylglycine, methyl ester The subtitle compound was prepared from the product of step (ii) (0.57 g) according to the method of example 1 step (vi). Purification was by chromatography eluting with 10% ethyl acetate in toluene, Yield 0.33 g.

MS: APCI(+ve) 540 (M+1)

iv) (±)-N-[4-[5-{2-Ethyl-8-methyl-5H-dibenzo[a,d] cyclohepten-5-yl}-3,4-dihydro-2-oxo-4-thioxo-1(2H)-pyrimidinyl]pyrimidin-2-yl]-N-methylglycine The title compound was prepared from the product of step (iii) (0.33 g) by the method of example 1 step (vii). Yield 0.23 g.

MS: APCI(+ve) 526 (M+1); 1H NMR:δ (DMSO at 90° C.) 12.40(s, 2H), 8.39(d, 1H), 8.05(s, 1H), 7.5(m, 2H), 7.20(m, 5H), 6.90(dd, 2H), 5.94(s, 1H), 4.33(s, 2H), 3.10(s, 3H), 2.60(q, 2H), 2.30(s, 3H), 1.20(t, 3H). MP: 187° C.

EXAMPLE 20

(±)-2-[2-[[4-[5-{2-Ethyl-8-methyl-5H-dibenzo[a,d] cyclohepten-5-yl}-3,4-dihydro-2-oxo-4-thioxo-1 (2H)-pyrimidinyl]pyrimidin-2-yl)][methyl]amino] acetylamino]-4-thiazoleacetic acid i) 2-[2-[Methylamino]acetylamino]-4-thiazoleacetic acid, ethyl ester The subtitle compound was prepared from N-tert-butoxycarbonyl sarcosine (6.0 g) and 2-amino-4-thiazoleacetic acid ethyl ester (6.6 g) by the method of example 10 step (i). Yield 5.24 g 1H NMR: δ ($D_2O$) 6.96(s,1H), 4.10–4.03(m,4H), 3.69(s, 2H), 2.72(s,3H), 1.11(t,3H).

ii) 2-[2-[[4-Fluoropyrimidin-2-yl][methyl]amino] acetylamino]-4-thiazoleacetic acid, ethyl ester The product of step (i) (3.0 g) was slurried in dichloromethane (100 ml) and treated with N,N-diisopropylethylamine (4.0 ml) forming a complete solution. 2,4-Difluoropyrimidine (J. Heterocyclic Chem. 1985, 22, 149) (0.6 g) was then added quickly with stirring. After 10 minutes the solvents were evaporated under reduced pressure and the residue purified by chromatography eluting with 20% ethyl acetate in isohexane. The first and minor component of the mixture to be eluted was the subtitle compound (0.77 g).

MS: APCI(–ve): 352 (M–1).

iii) (±)-5-[2-Ethyl-8-methyl-5H-dibenzo[a,d]cyclohepten-5-yl]-3,4-dihydro-4-thioxo-2(1H)-pyrimidinone The subtitle compound was prepared from the product of example 15 step (vii) (0.83 g) by the method of example 1 step (vi). Yield 0.58 g.

MS: APCI(+ve): 361 (M+1).

iv) (±)-5-[2-Ethyl-8-methyl-5H-dibenzo[a,d]cyclohepten-5-yl]-4-methylthio-2(1H)-pyrimidinone The product of step (iii) (0.58 g) was dissolved in ethanol (30 ml) and water (5 ml) and treated with sodium bicarbonate(0.14 g) and iodomethane (0.2 ml) and stirred for 24 hours. The reaction mixture was partitioned between ethyl acetate and brine. The organic phase was dried ($MgSO_4$) and solvent evaporated under reduced pressure. The residue was triturated with isohexane and filtered to give the product. Yield 0.41 g.

MS: APCI(+ve): 375(M+1), APCI(–ve): 359(M–15).

v) (±)-2-[2-[[4-[5-{2-Ethyl-8-methyl-5H-dibenzo[a,d] cyclohepten-5-yl}-4-methylthio-2-oxo-1(2H)-pyrimidinyl] pyrimidin-2-yl][methyl]amino]acetylamino]-4-thiazoleacetic acid, ethyl ester The product of step (iv) (0.37 g), and the product of step (ii) (0.35 g) was stirred with cesium carbonate (0.32 g) in dry 1-methyl-2-pyrrolidinone (15 ml) at 65–70° C. for 20 hours. The reaction mixture was partitioned between ethyl acetate and brine. The organic layer collected, dried ($MgSO_4$), and solvent evaporated under reduced pressure. Yield 0.61 g.

MS: APCI(+ve): 708(M+1).

vi) (±)-2-[2-[[4-[5-{2-Ethyl-8-methyl-5H-dibenzo[a,d] cyclohepten-5-yl}-3,4-dihydro-2-oxo-4-thioxo-1(2H)-pyrimidinyl]pyrimidin-2-yl][methyl]amino]acetylamino]-4-thiazoleacetic acid, ethyl ester The product from step (v) (0.61 g) was dissolved in dry pyridine (20 ml) and triethylamine (1.0 ml). Hydrogen sulphide gas was slowly bubbled through the solution for 15 minutes. The solvents were evaporated under reduced pressure and the residue azeotroped twice with toluene. The residue was purified by chromatography eluting with ethyl acetate in toluene. Yield 0.41 g.

MS: APCI(+ve): 694M+1).

vii) (±)-2-[2-[N-[4-[5-{2-Ethyl-8-methyl-5H-dibenzo[a,d] cyclohepten-5-yl}-3,4-dihydro-2-oxo-4-thioxo-1(2H)-pyrimidinyl]pyrimidin-2-yl]-N-methylamino]acetylamino]-4-thiazoleacetic acid The title compound was obtained from the product of step (vi) (0.41 g) according to the method of example 1 step (vii). Yield 0.2 g.

MS: APCI(+ve): 666 (M+1). 1H NMR: δ (DMSO at 90° C.) 12.80(br s, 1H), 12.32(br s, 2H), 8.36(d, 1H), 8.08(s, 1H), 7.49(m, 2H), 7.25(d, 1H), 7.20(m, 4H), 6.90(m, 3H), 5.92(s, 1H), 4.55(s, 2H), 3.62(s, 2H), 3.20(s, 3H), 2.60(q, 2H), 2.30(s, 3H), 1.11(t, 3H) MP: 205° C.

EXAMPLE 21

2-[2-[[4-[5-{2,8-Dimethyl-5H-dibenzo[a,d] cyclohepten-5-yl}-3,4-dihydro-2,4-dioxo-1(2H)-pyrimidinyl]pyrimidin-2-yl][methyl]amino] acetylamino]-4-tbiazoleacetic acid i) 2-[2-[[4-5-{2,8-Dimethyl-5H-dibenzo[a,d]cyclohepten-5-yl}-3,4-dihydro-2,4-dioxo-1(2H)-pyrimidinyl]pyrimidin-2-yl][methyl]amino]acetylamino]-4-thiazoleacetic acid, ethyl ester The subtitle compound was prepared from the product of example 8 step (ii) (0.6 g) and the product of example 20 step (i) (1.31 g) by the method of example 7 step (i). Purification was by precipitation with ether and filtration. Yield 0.60 g MS: APCI(+ve): 664 (M+1, 100%).

ii) 2-[2-[[4-[5-{2,8-Dimethyl-5H-dibenzo[a,d]cyclohepten-5-yl}-3,4-dihydro-2,4-dioxo-1(2H)-pyrimidinyl]pyrimidin-2-yl][methyl]amino]acetylamino]-4-thiazoleacetic acid The title compound was prepared from the product of step (i) (0.19 g) by the method of example 1 step (vii). Yield 0.097 g.

MS: APCI(+ve): 636 (M+1) 1H NMR: δ (DMSO, 90° C.) 12.07 (br s, 2H), 11.10 (s,1H), 8.31 (d,1H), 7.78 (br s,1H), 7.41 (d,2H), 7.25 (d, 1H), 7.17–7.13 (m,4H), 6.93 (s,1H), 6.86 (s,2H), 5.33 (s,1H), 4.52 (s,2H), 3.60 (s,2H), 3.05 (s,3H), 2.26 (s,6H). MP:210° C.

EXAMPLE 22

(±)-2-[2-[[4-[5-{2-Ethyl-8-methyl-5H-dibenzo[a,d]cyclohepten-5-yl}-3,4-dihydro-2,4-dioxo-1(2H)-pyrimidinyl]pyrimidin-2-yl][methyl]amino]acetylamino]-4-thiazoleacetic acid i) (±)-2-[2-[[4-[5-{2-Ethyl-8-methyl-5H-dibenzo[a,d]cyclohepten-5-yl}-3,4-dihydro-2,4-dioxo-1(2H)-pyrimidinyl]pyrimidin-2-yl][methyl]amino]acetylamino]-4-thiazoleacetic acid, ethyl ester The subtitle compound was prepared from the product of example 15 step (viii) (0.5 g) and the product of example 20 step (i) (0.73 g) by the method of example 7 step (i). Purification was by precipitation with ethyl acetate/isohexane and filtration. Yield 0.59 g.

MS: APCI(+ve): 678 (M+1)

ii) (±)-2-[2-[[4-[5-{2-Ethyl-8-methyl-5H-dibenzo[a,d]cyclohepten-5-yl}-3,4-dihydro-2,4-dioxo-1(2H)-pyrimidinyl]pyrimidin-2-yl][methyl]amino]acetylamino]-4-thiazoleacetic acid The title compound was prepared from the product of step (i) (0.58 g) by the method of example 1 step (vii). Yield 0.424 g.

MS: APCI(+ve): 650 (M+1); 1H NMR: δ (DMSO, 90° C.) 12.07(br s,2H), 11.20(br s,1H), 8.30(d,1H), 7.80(s,1H), 7.45–7.40(m,2H), 7.26–7.14(m,5H), 6.93(s,1H), 6.93–6.84 (m,2H), 5.34(s,1H), 4.52(s,2H), 3.60(s,2H), 3.05(s,3H), 2.58(q,2H), 2.26(s,3H), 1.16(t,3H). MP:188° C.

EXAMPLE 23

(±)-2-[2-[[4-[3,4-Dihydro-5-{2-methoxy-8-methyl-5H-dibenzo[a,d]cyclohepten-5-yl}-2,4-dioxo-1(2H)-pyrimidinyl]pyrimidin-2-yl][methyl]amino]acetylamino]-4-thiazoleacetic acid i) 4,5-Dihydro-2-[2-[2-[3-Methoxyphenyl]ethyl]-4-methylphenyl]-4,4-dimethyloxazole The subtitle compound was prepared from the product of example 15 step (iii) (20 g) and 3-methoxybenzyl chloride (17.4 ml) by the method of example 15 step (iv). Purification was by chromatography eluting with 5–10% ethyl acetate in isohexane. Yield 20.53 g. MS: APCI(+ve): 324 (M+1).

ii) 2-[2-[3-Methoxyphenyl]ethyl]-4-methylbenzoic acid

The subtitle compound was prepared from the product of step (i) (20.53 g) by the method of example 15 step (v). Used directly in the next step.

MS: APCI(–ve): 269 (M–1).

iii) 10,11-Dihydro-2-methoxy-8-methyl-5H-dibenzo[a,d]cyclohepten-5-one

The subtitle compound was prepared from the product of step (ii) by the method of example 15 step (vi). Purified by chromatography eluting with 5–10% ethyl acetate in isohexane. Yield 10.56 g.

MS: APCI(+ve): 253 (M+1).

iv) (±)-5-[2-Methoxy-8-methyl-5H-dibenzo[a,d]cyclohepten-5-yl]-2,4(1H,3H)-pyrimidinedione The subtitle compound was prepared from the product of step (iii) (10.5 g) by the method of example 8 step (i). Purified by chromatography eluting with 60–70% ethyl acetate in isohexane. Yield 3.25 g.

MS: APCI(+ve): 347 (M+1).

v) (±)-1-[2-Chloropyrimidin-4-yl]-5-[2-methoxy-8-methyl-5H-dibenzo[a,d]cyclohepten-5-yl]-2,4(1H,3H)-pyrimidinedione The subtitle compound was prepared from the product of step (iv) (1.0 g) by the method of example 6 step (i). Purified by chromatography eluting with 40–50% ethyl acetate in isohexane. Yield 0.57 g.

MS: APCI(+ve): 459 (M+1).

vi) (±)-2-[2-[[4-[3,4-Dihydro-5-{2-methoxy-8-methyl-5H-dibenzo[a,d]cyclohepten-5-yl}-2,4-dioxo-1(2H)-pyrimidinyl]pyrimidin-2-yl][methyl]amino]acetylamino]-4-thiazoleacetic acid, ethyl ester The subtitle compound was prepared from the product of step (v) (0.56 g) by the method of example 7 step (i). Purified by precipitation from ethyl acetate/isohexane. Yield 0.54 g MS: APCI(+ve): 680 (M+1).

vii) (±)-2-[2-[[4-[3,4-Dihydro-5-{2-methoxy-8-methyl-5H-dibenzo[a,d]cyclohepten-5-yl}-2,4-dioxo-1(2H)-pyrimidinyl]pyrimidin-2-yl][methyl]amino]acetylamino]-4-thiazoleacetic acid The title compound was prepared from the product of step (vi) (0.53 g) by the method of example 1 step (vii). Yield 0.38 g.

MS: APCI(+ve): 652 M+1). 1H NMR: δ (DMSO, 90° C.) 12.06(br s,2H), 11.20(s,1H), 8.31(d,1H), 7.79(s,1H), 7.45(d, 1H), 7.41(d,1H), 7.25(d,1H), 7.17(d,1H), 7.14(s,1H), 6.96–6.90(m,3H), 6.87(s,2H), 5.32(s,1H), 4.52(s,2H), 3.74 (s,3H), 3.60(s,2H), 3.06(s,3H), 2.27(s,3H). MP: 186° C.

EXAMPLE 24

(±)N-[4-[5-{2-Ethyl-8-methyl-5H-dibenzo[a,d]cyclohepten-5-yl}-3,4-dihydro-2,4-dioxo-1(2H)-pyrimidinyl]pyrimidin-2-yl]-3-azetidinecarboxylic acid The title compound was prepared from the product of example 15 step (viii) (0.2 g) and 3-azetidinecarboxylic acid (0.045 g) by the method of example 7 step (i). Purification was by precipitation with ethyl acetate/isohexane and filtration. Yield 0.14 g.

MS: APCI(+ve): 522 (M+1); 1H NMR: δ (DMSO) 12.79 (s,1H), 11.46(s,1H), 8.34(d,1H), 7.79(d,1H), 7.48–7.18(m, 7H), 6.95–6.86(m,2H), 5.33(s,1H), 4.17(br m,2H), 4.00(br m,2H), 3.63–3.53(m,1H), 2.59(q,2H), 2.28(s,3H), 1.16(t, 3H). MP:244° C.

EXAMPLE 25

2-[2-[[6-[5-{2,8-Dimethyl-5H-dibenzo[a,d]cyclohepten-5-yl}-3,4-dihydro-2-oxo-4-thioxo-1(2H)-pyrimidinyl]pyrimidin-4-yl][methyl]amino]acetylamino]-4-thiazoleacetic acid i) 5-[2,8-Dimethyl-5H-dibenzo[a,d]cyclohepten-5-yl]-3,4-dihydro-4-thioxo-2(1H)-pyrimidinone The subtitle compound was prepared from the product of example 8 step (i) (0.60 g) by the method of example 1 step (vi). Purification was by chromatography eluting with 30–50% ethyl acetate in isohexane. Yield 0.22 g.

MS: APCI(+ve): 347 (M+1).

ii) 5-[2,8-Dimethyl-5H-dibenzo[a,d]cyclohepten-5-yl]-4-methylthio-2(1H)-pyrimidinone Iodomethane (0.2 ml) was added to a stirred suspension of the product from step (i) (0.65 g) and sodium bicarbonate (0.4 g) in ethanol (15 ml) and water (4 ml). After stirring for 30 min, the reaction mixture was washed with water, 1M hydrochloric acid, aqueous sodium bicarbonate, water, dried (MgSO$_4$) and evaporated under reduced pressure. The residue was triturated with ether and filtered. Yield 0.49 g.

MS: APCI(+ve): 361 (M+1).

iii) 1-[6-Chloropyrimidin-4-yl]-5-[2,8-dimethyl-5H-dibenzo[a,d]cyclohepten-5-yl]-4-methylthio-2(1H)-pyrimidinone The subtitle compound was prepared from the product of step (ii) (0.33 g) and 4,6-dichloropyrimidine (0.149 g) by the method of example 16 step (i). Purification was by chromatography eluting with 30% ethyl acetate in isohexane. Yield 0.23 g. 1H NMR: δ (DMSO) 8.98(d,1H), 8.24(d,1H), 7.61 (d,1H), 7.53(d,2H), 7.24(d,2H), 7.23(s,2H), 6.95(s,2H), 5.41 (s,1H), 2.42(s,3H), 2.30(s,6H).

iv) 2-[2-[[6-[5-{2,8-Dimethyl-5H-dibenzo[a,d]cyclohepten-5-yl}-4-methylthio-2-oxo-1(2H)-pyrimidinyl]pyrimidin-4-yl][methyl]amino]acetylamino]-4-thiazoleacetic acid, ethyl ester A mixture of the product from step (iii) (0.22 g), the product from example 20 step (i) (0.252 g) and N,N-diisopropylamine (0.4 ml) in 1-methyl-2-pyrrolidinone (4 ml) was stirred at room temperature overnight. The reaction mixture was partitioned between 1M hydrochloric acid and ethyl acetate. The organic layer was washed with water, dried (MgSO$_4$) and evaporated under reduced pressure. Used directly in the next step.

MS: APCI(+ve): 694 (M+1).

v) 2-[2-[[6-[5-{2,8-Dimethyl-5H-dibenzo[a,d]cyclohepten-5-yl}-3,4-dihydro-2-oxo-4-thioxo-1(2H)-pyrimidinyl]pyrimidin-4-yl][methyl]amino]acetylamino]-4-thiazoleacetic acid, ethyl ester The subtitle compound was prepared from the product of step (iv) by the method of example 20 step (vi). Yield 0.21 g.

MS: APCI(+ve): 680 (M+1).

vi) 2-[2-[[6-[5-{2,8-Dimethyl-5H-dibenzo[a,d]cyclohepten-5-yl}-3,4-dihydro-2-oxo-4-thioxo-1(2H)-pyrimidinyl]pyrimidin-4-yl][methyl]amino]acetylamino]-4-thiazoleacetic acid The title compound was prepared from the product of step (v) (0.20 g) by the method of example 1 step (vii). Yield 0.106 g.

MS: APCI(+ve): 652 (M+1). 1H NMR: δ (DMSO) 12.92 (s,1H), 12.35(s,2H), 8.42(s,1H), 7.88(s,1H), 7.48(d,2H), 7.18–7.15(2xs,5H), 6.95(s,1H), 6.91(s,2H), 5.89(s,1H), 4.55 (br s,2H), 3.60(s,2H), 3.09(s,3H), 2.27(s,6H). MP:215° C.

EXAMPLE 26

(±)-N-[4-[5-{2-Ethyl-8-methyl-5H-dibenzo[a,d]cyclohepten-5-yl}-3,4-dihydro-2,4-dioxo-1(2H)-pyrimidinyl]pyrimidin-2-yl]-L-proline i) (±)-N-[4-[5-{2-Ethyl-8-methyl-5H-dibenzo[a,d]cyclohepten-5-yl}-3,4-dihydro-2,4-dioxo-1(2H)-pyrimidinyl]pyrimidin-2-yl]-L-proline, methyl ester The subtitle compound was prepared from the product of example 15 step (viii) (0.5 g) and L-proline methyl ester hydrochloride (0.265 g) by the method of example 10 step (ii). Purification was by chromatography eluting with 40% ethyl acetate in isohexane. Yield 0.47 g.

MS: APCI(+ve): 550 (M+1).

ii) (±)-N-[4-[5-{2-Ethyl-8-methyl-5H-dibenzo[a,d]cyclohepten-5-yl}-3,4-dihydro-2,4-dioxo-1(2H)-pyrimidinyl]pyrimidin-2-yl]-L-proline The title compound was prepared from the product of step (i) (0.16 g) by the method of example 1 step (vii). Yield 0.03 g.

MS: APCI(+ve): 536 (M+1). 1H NMR: δ (DMSO, 90° C.) 12.17(s,1H), 11.18(s,1H), 8.29(d,1H), 7.85(br s,1H), 7.46–7.40(m,2H), 7.24–7.16(m,5H), 6.96–6.83(m,2H), 5.32 (s,1H), 4.43(d,1H), 3.42(br s,2H), 2.60(q,2H), 2.38–2.29(m, 1H), 2.29(s,3H), 2.05–2.02(br m,3H), 1.18(t,3H). MP:185° C.

EXAMPLE 27

(±)-N-[4-[5-{2-Ethyl-8-methyl-5H-dibenzo[a,d]cyclohepten-5-yl}-3,4-dihydro-2-oxo-4-thioxo-1(2H)-pyrimidinyl]pyrimidin-2-yl]-L-proline i) (±)-N-[4-[5-{2-Ethyl-8-methyl-5H-dibenzo[a,d]cyclohepten-5-yl}-3,4-dihydro-2-oxo-4-thioxo-1(2H)-pyrimidinyl]pyrimidin-2-yl]-L-proline, methyl ester The subtitle compound was prepared from the product of example 26 step (i) (0.3 g) by the method of example 1 step (vi). Purification was by chromatography eluting with 20–40% ethyl acetate in isohexane. Yield 0.25 g.

MS: APCI(+ve): 566 (M+1).

ii) (±)-N-[4-[5-{2-Ethyl-8-methyl-5H-dibenzo[a,d]cyclohepten-5-yl}-3,4-dihydro-2-oxo-4-thioxo-1(2H)-pyrimidinyl]pyrimidin-2-yl]-L-proline The title compound was prepared from the product of step (i) (0.25 g) by the method of example 1 step (vii). Yield 0.085 g.

MS: APCI(+ve): 552 (M+1). 1H NMR: δ (DMSO, 90° C.) 12.51(s,1H), 12.20(s,1H), 8.33(d,1H), 8.10(br s,1H), 7.53–7.47(m,2H), 7.30–7.16(m,5H), 7.00–6.89(m,2H), 5.85 (s,1H), 4.47(d,1H), 3.48(br s,2H), 2.59(q,2H), 2.38–2.32(m, 1H), 2.28(s,3H), 2.05 (br s,3H), 1.17(t,3H). MP:175° C.

EXAMPLE 28

(±)-2-[5-{2-Ethyl-8-methyl-5H-dibenzo[a,d]cyclohepten-5-yl}-3,4-dihydro-2,4-dioxo-1(2H)-pyrimidinyl]-9H-purine-9-acetic acid.

i) N-[2-Chloro-5-nitropyrimidin-4-yl]glycine, 1,1-dimethylethyl ester.

A stirred mixture of 2,4-dichloro-5-nitropyrimidine (1.00 g) (J.Chem.Soc. 1951, 1568), N,N-diisopropylethylamine (0.89 g), isohexane (10 ml) and dichloromethane (10 ml) was treated portionwise over 10 minutes at 0° C. with glycine t-butyl ester hydrochloride (0.58 g). The mixture was stirred at 0° C. for 2 hours and evaporated. Purification was by chromatography eluting with 10% ethyl acetate in isohexane. Yield 0.9 g.

MS: APCI(−ve): 288 (M−1).

ii) (±)-N-[2-[5-{2-Ethyl-8-methyl-5H-dibenzo[a,d]cyclohepten-5-yl}-3,4-dihydro-2,4-dioxo-1(2H)-pyrimidinyl]-5-nitropyrimidin-4-yl]glycine, 1,1-dimethylethyl ester To a stirred suspension of sodium hydride (60% dispersion in oil, 116 mg) in 1-methyl-2-pyrrolidinone (10 ml) was added the product of example 15 step (vii) (1.00 g). After 0.5 hours the solution was treated with the product from step (i) (0.838 g) and stirred overnight. The mixture was diluted with brine and extracted with ethyl acetate. The combined extracts were dried (MgSO₄) and evaporated. Purification was by chromatography eluting with 15% ethyl acetate in toluene. Yield 0.89 g.

MS: APCI(−ve): 596 (M−1).

iii) (±)-N-[5-Amino-2-[5-{2-ethyl-8-methyl-5H-dibenzo[a,d]cyclohepten-5-yl}-3,4-dihydro-2,4-dioxo-1(2H)-pyrimidinyl]pyrimidin-4-yl]glycine, 1,1-dimethylethyl ester.

A mixture of the product from step (ii) (0.766 g), iron powder (1 g), ammonium chloride (1 g), water (5 ml) and methanol (20 ml) was stirred and heated under reflux for 2 hours and filtered through celite. The pad was washed with methanol and the combined filtrates were evaporated. The residue was taken up in ethyl acetate, was washed with water, dried (MgSO₄) and evaporated to give an oil. The oil was crystallised from warm ethyl acetate. Yield 0.558 g.

MS: APCI(+ve): 567 (M+1).

iv) (±)-2-[5-{2-Ethyl-8-methyl-5H-dibenzo[a,d]cyclohepten-5-yl}-3,4-dihydro-2,4-dioxo-1(2H)-pyrimidinyl]-9H-purine-9-acetic acid, 1,1-dimethylethyl ester.

A mixture of the product from step (iii) (478 mg) and diethoxymethyl acetate (0.5 ml) was stirred at 90° C. for 15 hours, diluted with methanol and evaporated. Purification was by chromatography eluting with ethyl acetate. Yield 0.28 g. 1H NMR: δ (DMSO) 11.52(s,1H), 9.28(s,1H), 8.75(s,1H), 7.5–7.6(m.,6H), 7.2–7.3(m.,4H), 7.2(s,1H), 6.94 (d,2H), 5.4(s,1H), 5.14(s,2H), 2.62(q,2H), 2.32(s,3H), 1.47 (s,9H), 1.21(t,3H).

v) (±)-2-[5-{2-Ethyl-8-methyl-5H-dibenzo[a,d]cyclohepten-5-yl}-3,4-dihydro-2,4-dioxo-1(2H)-pyrimidinyl]-9H-purine-9-acetic acid.

A solution of the product from step (iv) (0.26 g) in trifluoroacetic acid (5 ml) and dichloromethane (10 ml) was stirred overnight and evaporated. The residue was triturated with ether and filtered off. Yield 0.21 g.

MS: APCI(+ve): 521 (M+1); 1H NMR: δ 11.45(s,1H), 9.21(s,1H), 8.69(s,1H), 7.41–7.47(m,2H), 7.16–7.26(m,4H), 7.06(s,1H), 6.90(br s,1H), 5.34(s,1H), 5.12(s,2H), 2.57(q, 2H), 2.26(s,3H), 1.14(t,3H). MP: 212–220° C.

EXAMPLE 29

N-[2-[5-{2-Ethyl-8-methyl-5H-dibenzo[a,d]cyclohepten-5-yl}-3,4-dihydro-2,4-dioxo-1(2H)-pyrimidinyl]-5-nitropyrimidin-4-yl]glycine.

A solution of the product from example 28 step (ii) (0.07 g) in dichloromethane (1 ml) and trifluoroacetic acid (1 ml) was stirred overnight and evaporated. The residue was triturated with ether and filtered off. Yield 0.05 g.

MS: APCI(+ve): 541 (M+1) 1H NMR: δ (DMSO) 13.12 (br s,1H), 11.48(s,1H), 9.19(t,1H), 9.15(s,1H), 7.41–7.47(m, 2H), 7.18–7.24(m,4H), 6.93(br s,2H), 5.33(s,1H), 4.21(d, 2H), 2.59(q,2H), 2.28(s,3H), 1.16(t,3H). MP: >240° C.

EXAMPLE 30

(±)-2-[2-[[4-[3,4-dihydro-5-{2-methyl-8-[1-methylethyl]-5H-dibenzo[a,d]cyclohepten-5-yl}-2,4-dioxo-1(2H)-pyrimidinyl]pyrimidin-2-yl]amino] acetylamino]-4-thiazoleacetic acid i) 4,5-Dihydro-4,4-dimethyl-2-[4-[1-methylethyl]phenyl]oxazole The subtitle compound was prepared from 4-[1-methylethyl]benzoic acid (25.3 g) using the method of example 15 step (iii). Yield 26.13 g.

MS: APCI(+ve): 218(M+1, 100%).

ii) 4,5-Dihydro-4,4-dimethyl-2-[2-methyl-4-[1-methylethyl]phenyl]oxazole n-Butyllithium (52.8 ml of a 2.5M solution in hexane) was added dropwise to a stirred solution of the product of step (i) (27.6 g) in tetrahydrofuran (100 ml) at −20° C. After 2 hours methyl iodide (85.3 g) was added and the mixture was stirred for 2 hours at this temperature then 0.5 hours at room temperature. The reaction mixture was partitioned between brine and ethyl acetate. The aqueous solution was extracted with ethyl acetate. The organic solution was dried (MgSO₄) and evaporated under reduced pressure. Purification was by chromatography eluting with 5% ethyl acetate in isohexane. Used directly in the next step.

iii) 4,5-Dihydro-4,4-dimethyl-2-[4-[1-methylethyl]-2-[2-[3-methylphenyl]ethyl]phenyl]oxazole The subtitle compound was prepared from the product of step (ii) and 3-bromomethyltoluene (9.25 g) using the method of example 15 step (iv). Purification was by chromatography eluting with toluene. Yield 4.8 g.

MS: APCI(+ve): 336(M+1, 100%).

iv) 4-[1-Methylethyl]-2-[2-[3-methylphenyl]ethyl]benzoic acid

The subtitle compound was made from the product of step (iii) (4.85 g) using the method of example 15 step (v). Yield 3.43 g.

MS: APCI(−ve): 281 (M−1, 100%).

v) 10,11-Dihydro-2-methyl-8-[1-methylethyl]-5H-dibenzo[a,d]cyclohepten-5-one The subtitle compound was prepared from the product of step (iv) (3.36 g) using the method of example 15 step (vi). Yield 2.73 g.

MS: APCI(+ve): 265 (M+1, 100%)

vi) (±)-5-[2-Methyl-8-[1-methylethyl]-5H-dibenzo[a,d]cyclohepten-5-yl]-2,4(1H,3H)-pyrimidinedione The subtitle compound was prepared from the product of step (v) (2.73 g) using the method of example 8 step (i). Yield 2.8 g. Used directly in the next step.

vii) (±)-1-[2-Chloropyrimidin-4-yl]-5-[2-methyl-8-[1-methylethyl]-5H-dibenzo[a,d]cyclohepten-5-yl]-2,4(1H, 3H)-pyrimidinedione The subtitle compound was prepared from the product of step (vi) (1.00g) by the method of example 6 step (i). Purification was by chromatography eluting with 20% ethyl acetate in toluene. Yield 0.373 g MS: APCI(+ve): 471 (M+1)

viii) (±)-2-[2-[[4-]3,4-Dihydro-5-{2-methyl-8-[1-methylethyl]-5H-dibenzo[a,d]cyclohepten-5-yl}-2,4-dioxo-1(2H)-pyrimidinyl]pyrimidin-2-yl]amino]acetylaminol-4-thiazoleacetic acid, ethyl ester.

The subtitle compound was prepared from the product of step (vii) (373mg) using the method of example 10 step (ii). Purification was by chromatography eluting with 60% ethyl acetate in toluene. Yield 0.13 g.

MS: APCI(+ve): 678 (M+1).

ix) (±)-2-[2-[[4-[3,4-Dihydro-5-{2-methyl-8-(1-methylethyl)-5H-dibenzo[a,d]cyclohepten-5-yl}-2,4-dioxo-1(2H)-pyrimidinyl]pyrimidin-2-yl]amino]acetylamino]-4-thiazoleacetic acid The title compound was prepared from the product of step (viii) (0.12 g) by the method of example 1 step (vii). Purification was by recrystallisation from a mixture of ethyl acetate and isohexane. Yield 0.04 g.

MS: APCI(+ve): 649 (M+1); 1H NMR: δ (DMSO, 90° C.) 12.06(br s,2H), 11.21(br s, 1H), 8.29(d,1H), 7.65(s,1H), 7.35–7.44(m, 2H), 7.12–7.24(m,6H), 6.89–6.98(m,3H), 5.33(s,1H), 4.23(d,2H), 3.61(s,3H),2.80–2.91(m,1H), 2.24 (s,3H), 1.16(d,6H). MP: 215–220° C.

EXAMPLE 31

(±)-2-[2-[[4-[3,4-Dihydro-5-{2-methyl-8-propyl-5H-dibenzo[a,d]cyclohepten-5yl}-2,4-dioxo-1(2H)-pyrimidinyl]pyrimidin-2-yl]amino]acetylamino]-4-thiazoleacetic acid i) 1-Bromo-3-propylbenzene A solution of 3'-bromopropiophenone (25 g) and triethylsilane (57 ml) in trifluoroacetic acid (50ml) was heated at reflux for 16 hours. The reaction mixture was evaporated under reduced pressure and the residue was purified by chromatography eluting with isohexane. Yield 25.14 g. The subtitle compound was contaminated with 17 mole % of 3-(1-propenyl)bromobenzene. Used directly in the next step. 1H NMR: δ(CDCl$_3$) 7.32(m,2H), 7.10(m,2H), 2.55(t,2H), 1.61(m,2H), 0.90(t3H).

ii) 3-Propylphenylmethanol

The subtitle compound was prepared from the product of step (i) (24.14 g) by the method of example 15 step (i). Used directly in the next step. Yield 15.8 g.

iii) 1-Bromomethyl3-propylbenzene

The subtitle compound was prepared from the product of step (ii) (15.8 g) by the method of example 15 step (ii). Purification was by chromatography eluting with isohexane. Yield 11.7 g. The subtitle compound was contaminated with 15 mole % of 1-bromomethyl-3-(1-propenyl)benzene. Used directly in the next step. 1H NMR: δ(CDCl$_3$) 7.30–7.10(m, 4H), 4.49(d,2H), 2.60(m,2H), 1.65(m,2H), 0.95(m,3H).

iv) 4,5-Dihydro-4,4-dimethyl-2-[4-methyl-2-[2-[3-propylphenyl]ethyl]phenyl]oxazole.

The subtitle compound was prepared from the product of step (iii) (11.7 g) and the product of example 15 step (iii) (11.2 g) by the method of example 15 step (iv). Purification was by chromatography eluting with 12% ethyl acetate in isohexane. Yield 15.4 g. The subtitle compound was contaminated with 14 mole % of 4,5-dihydro-4,4-dimethyl-2-[4-methyl-2-[2-[3-[1-propenyl]phenyl]ethyl]phenyl] oxazole. Used directly in the next step.

MS: APCI(+ve): 336 (M+1, 100%).

v) 4-Methyl-2-[2-[3-propylphenyl]ethyl]benzoic acid

The subtitle compound was prepared from the product of step (iv) (15.4 g) by the method of example 15 step (v). The crude reaction product was contaminated with 4-methyl-2-[2-[3-[1-propenyl]phenyl]ethyl]benzoic acid. The crude reaction product was dissolved in ethyl acetate (100 ml) and the solution was hydrogenated over 10% palladium on carbon (1 g) at 3 atmospheres pressure for 2 hours. The catalyst was removed by filtration and the filtrate was evaporated. Yield 12.8 g.

MS: APCI(−ve): 281 (M-1, 100%).

vi) 10,11-Dihydro-2-methyl-8-propyl-5H-dibenzo[a,d]cyclohepten-5-one.

The subtitle compound was prepared from the product of step (v) (12.8 g) by the method of example 15 step (vi). Purification was by chromatography eluting with isohexane. Yield 7.36 g.

MS: APCI(+ve): 265 (M+1, 100%).

vii) (±)-5-[2-Methyl-8-propyl-5H-dibenzo[a,d]cyclohepten-5-yl]-2,4(1H,3H)-pyrimidinedione.

The subtitle compound was prepared from the product of step (vi) (7.0 g) by the method of example 8 step (i). Yield 7.30 g.

MS: APCI(+ve): 359 (M+1).

viii) (±)-1-[2-Chloropyrimidin-4-yl]-5-[2-methyl-8-propyl-5H-dibenzo[a,d]cyclohepten-5-yl]-2,4(1H,3H)-pyrimidinedione.

The subtitle compound was prepared from the product of step (vii) (2.50 g) by the method of example 6 step (i). Purification was by chromatography eluting with 40% ethyl acetate in isohexane. Yield 0.80 g.

MS: APCI(+ve): 471 (M+1, 100%).

ix) (±)-2-[2-[[4-[3,4-Dihydro-5-{2-methyl-8-propyl-5H-dibenzo[a,d]cyclohepten-5-yl}-2,4-dioxo-1(2H)-pyrimidinyl]pyrimidin-2-yl]amino]acetylamino]-4-thiazoleacetic acid, ethyl ester The subtitle compound was prepared from the products of step (viii) (0.40 g) and example 10 step (i) (0.80 g) by the method of example 10 step (ii). Purification was by chromatography eluting with 66% ethyl acetate in isohexane. Yield 0.29 g.

MS: APCI(+ve): 678 (M+1, 100%).

x) (±)-2-[2-[[4-[3,4-Dihydro-5-{2-methyl-8-propyl-5H-dibenzo[a,d]cyclohepten-5yl}-2,4-dioxo-1(2H)-pyrimidinyl]pyrimidin-2-yl]amino]acetylamino]-4-thiazoleacetic acid.

The title compound was prepared from the product of step (ix) (0.29 g) by the method of example 1 step (vii). Yield 0.123 g.

MS: APCI(+ve): 650 (M+1, 100%); 1H NMR: δ (DMSO, 90° C.) 11.17(s,1H), 8.29(d,1H), 7.65(s,1H), 7.37(t,2H), 7.3–7.1(m,6H), 6.96(s,1H), 6.92(q,2H), 5.32(s,1H), 4.23(s, 2H), 3.61(s,2H),2.24(s,3H), 1.55(sextet,2H), 0.85(t,3H). MP: 198–200° C.

EXAMPLE 32

(±)-N-[4-[3,4-Dihydro-5-{2-methyl-8-propyl-5H-dibenzo[a,d]cyclohepten-5-yl}-2-oxo-4-thioxo-1(2H)-pyrimidinyl]pyrimidin-2-yl]-N-methylglycine i) (±)-N-[4-[3,4-Dihydro-5-{2-methyl-8-propyl-5H-dibenzo[a,d]cyclohepten-5-yl}-2,4-dioxo-1(2H)-pyrimidinyl]pyrimidin-2-yl]-N-methylglycine, methyl ester The subtitle compound was prepared from the product of example 31 step (viii) (0.39 g) and sarcosine methyl ester hydrochloride (0.23 g) by the method of example 7 step (i). Purification was by chromatography eluting with 40% ethyl acetate in isohexane. Yield 0.18 g.

MS: APCI(+ve): 538 (M+1, 100%)

ii) (±)-N-[4-[3,4-Dihydro-5-{2-methyl-8-propyl-5H-dibenzo[a,d]cyclohepten-5-yl}-2-oxo-4-thioxo-1(2H)-pyrimidinyl]pyrimidin-2-yl]-N-methylglycine, methyl ester The subtitle compound was prepared from the product of step (i) (0.1 8 g) by the method of example 1 step (vi). Purification was by chromatography eluting with 12.5% ethyl acetate in toluene. Yield 0.08 g.

MS: APCI(+ve): 554 (M+1, 100%);

iii) (±)-N-[4-[3,4-Dihydro-5-{2-methyl-8-propyl-5H-dibenzo[a,d]cyclohepten-5-yl}-2-oxo-4-thioxo-1(2H)-pyrimidinyl]pyrimidin-2-yl]-N-methylglycine The title compound was prepared from the product of step (ii) by the method of example 1 step (vii). The product was precipitated by the addition of isohexane/ethyl acetate. Yield 0.04 g.

MS: APCI(+ve): 540 (M+1, 100%); 1H NMR: δ (DMSO, 90° C.) 12.49 (br s,1H), 8.36 (d,1H), 8.02 (s,1H), 7.49 (t,2H), 7.24(d,1H), 7.17 (s,4H), 6.91 (s,2H), 5.90 (s,1H), 4.31 (s,2H), 3.07 (s,3H), 2.5 (m,2H), 2.28 (s,3H), 1.58 (sextet,2H), 0.88 (t,3H). MP: 145–150° C.

EXAMPLE 33

(±)-2-[2-[[4-[5-{2-Ethyl-8-methyl-5H-dibenzo[a,d]
cyclohepten-5-yl}-3,4-dihydro-2,4-dioxo-1(2H)-
pyrimidinyl]pyrimidin-2-yl]amino]acetylamino]-5-
thiazoleacetic acid i) 4-Oxobutanoic acid, ethyl ester Ethyl succinyl cloride (4.1 g) was added to a suspension of 10% palladium on carbon (0.3 g) and 2,6-lutidine (2.9 ml) in dry tetrahydrofuran (100 ml). The mixture was hydrogenated at 3 atmospheres pressure for 24 hours. The reaction mixture was filtered and the filtrate evaporated under reduced pressure. Yield 3.15 g. 1H NMR: δ (CDCl$_3$) 9.82 (s,1H), 4.16 (q,2H), 2.80 (t,2H), 2.63 (t,2H), 1.26 (t,3H).

ii) 3-Bromo-4-oxobutanoic acid ethyl ester.

A mixture of bromine (1.24 ml) and dry 1,4-dioxane (25 ml) gave an orange suspension; the solid was dissolved by the addition of diethyl ether (25 ml). This solution was then added dropwise under nitrogen to a solution of the product of step (i) (3.15 g) in dry 1,4-dioxane (25 ml) at such a rate as to effect decolourisation of the reaction mixture before addition of the next drop. After the addition was complete the reaction mixture was stirred for 0.5 hours then diluted with water and diethyl ether. The aqueous phase was separated and extracted with diethyl ether. The combined organic extracts were dried (MgSO$_4$) and evaporated under reduced pressure. Yield 3.53 g. 1H NMR: δ (CDCl$_3$) 9.54 (s,1H), 4.68 (t,1H), 4.20 (q,2H), 3.22 (dd,1H), 2.90 (dd,1H), 1.28 (t,3H).

iii) 2-Amino-5-thiazoleacetic acid ethyl ester.

A mixture of thiourea (1.28 g) and the product of step (ii) (3.53 g) was heated at 80° C. for 1 hour. The reaction mixture was diluted with water and washed with diethyl ether. The aqueous phase was basified to pH9 by the addition of concentrated aqueous ammonia and the resultant suspension was extracted with ethyl acetate. The ethyl acetate extracts were dried (MgSO$_4$) and evaporated under reduced pressure. Yield 2.15 g.

MS: APCI(+ve): 187 (M+1, 100%)

iv) 2-[2-Aminoacetylamino]-5-thiazoleacetic acid ethyl ester

The subtitle compound was prepared from the product of step (iii) (1.86 g) and N-(tert-butoxycarbonyl)glycine (1.75 g) by the method of example 10 step (i). Yield 3.13 g.

MS: APCI(+ve): 244 (M+1, 100%).

v) (±)-2-[2-[[4-[5-{2-Ethyl-8-methyl-5H-dibenzo[a,d]
cyclohepten-5-yl}-3,4-dihydro-2,4-dioxo-1(2H)-
pyrimidinyl]pyrimidin-2-yl]amino]acetylamino]-5-
thiazoleacetic acid, ethyl ester The subtitle compound was prepared from the product of step (iv) (1.05 g) and the product from example 15 step (viii) (0.5 g) by the method of example 10 step (ii). Purification was by chromatography eluting with 66–100% ethyl acetate in toluene. Yield 0.27 g.

MS: APCI(+ve): 664 (M+1, 100%).

vi) (±)-2-[2-[[4-[5-{2-Ethyl-8-methyl-5H-dibenzo[a,d]
cyclohepten-5-yl}-3,4-dihydro-2,4-dioxo-1(2H)-
pyrimidinyl]pyrimidin-2-yl]amino]acetylamino]-5-
thiazoleacetic acid The title compound was prepared from the product of step (v) (0.27 g) by the method of example 1 step (vii). Yield 0.13 g.

MS: APCI(+ve): 636 (M+1, 100%); 1H NMR: δ (DMSO, 90° C.) 8.29 (d,1H), 7.66 (s,1H), 7.41 (d,1 H), 7.38 (d, 1H), 7.25 (br s,2H), 7.20–7.10 (m,5H), 6.92 (d,2H), 5.33 (s,1H), 4.23 (d,2H), 3.71 (s,2H), 2.56 (q,2H), 2.24 (s,3H), 1.14 (t,3H). MP: 206–208° C.

EXAMPLE 34

(±)-2-[2-[[4-[5-{2-Ethyl-8-methyl-5H-dibenzo[a,d]
cyclohepten-5-yl}-3,4-dihydro-2,4-dioxo-1(2H)-
pyrimidinyl]pyrimidin-2-yl][methyl]amino]
acetylamino]-4-thiazolecarboxylic acid.

i) 2-[2-[Methylamino]acetylamino]-4-thiazolecarboxylic acid ethyl ester.

The subtitle compound was prepared from N-(tert-butoxycarbonyl)sarcosine (1.99 g) and 2-amino-4-thiazole carboxylic acid ethyl ester (J.Heterocyclic Chem. 1989.26, 1643) (2.0 g) by the method of example 10 step (i) Yield 2.47 g.

MS: APCI(–ve): 242 (M–1)

ii) (±)-2-[2-[[4-[5-{2-Ethyl-8-methyl-5H-dibenzo[a,d]
cyclohepten-5-yl}-3,4-dihydro-2,4-dioxo-1(2H)-
pyrimidinyl]pyrimidin-2-yl][methyl]amino]acetylamino]-4-
thiazolecarboxylic acid ethyl ester.

The subtitle compound was prepared from the product of step (i) (1.05 g) and the product from example 15 step (viii) (0.5 g) by the method of example 10 step (ii). Purification was by chromatography eluting with 33% toluene in ethyl acetate. Yield 0.37 g.

MS: APCI(-ve): 663 (M–1)

iii) (±)-2-[2-[[4-[5-{2-Ethyl-8-methyl-5H-dibenzo[a,d]
cyclohepten-5-yl}-3,4-dihydro-2,4-dioxo-1(2H)-
pyrimidinyl]pyrimidin-2-yl][methyl]amino]acetylamino]-4-
thiazolecarboxylic acid.

The title compound was prepared from the product of step (ii) (0.1 5 g) by the method of example 1 step (vii). Yield 0.070 g.

MS: APCI(-ve): 635 (M–1); 1H NMR: δ (DMSO) 12.87 (s,1H), 12.62(s,1H), 11.48(s,1H), 8.31(d,1H), 7.98(s,1H), 7.86(s,1H), 7.46(s,2H), 7.30(m,1H), 7.22–7.18(m,4H), 6.92 (s,2H), 5.36(s,1H), 4.55(s,2H), 3.05(s,3H), 2.60(m,1H), 2.28(s,3H), 1.16(m,3H). MP: 213–6° C. (dec.).

EXAMPLE 35

(±)-2-[[1-[4-[5-{2-Ethyl-8-methyl-5H-dibenzo[a,d]
cyclohepten-5-yl}-3,4-dihydro-2,4-dioxo-1(2H)-
pyrimidinyl]pyrimidin-2-yl]azetidin-3-yl]
carbonylamino]-4-thiazoleacetic acid i) (±)-2-[[1[-4-[5-{2-Ethyl-8-methyl-5H-dibenzo[a,d]
cyclohepten-5-yl}-3,4-dihydro-2,4-dioxo-1(2H)-
pyrimidinyl]pyrimidin-2-yl]azetidin-3-yl]carbonylamino]-
4-thiazoleacetic acid, ethyl ester The subtitle compound was prepared from the product of example 15 step (viii) (0.53 g) according to the method of example 10 step (ii). Yield 0.52 g MS: APCI(+ve): 690 (M+1)

ii) (±)-2-[[1-[4-[5-{2-Ethyl-8-methyl-5H-dibenzo[a,d]
cyclohepten-5-yl}-3,4-dihydro-2,4-dioxo-1(2H)-
pyrimidinyl]pyrimidin-2-yl]azetidin-3-yl]carbonylamino]-
4-thiazoleacetic acid The title compound was prepared from the product of step (i) (0.52 g) according to the method of example 1 step (vii). Yield: 0.3 g MS: APCI(+ve): 662 (M+1), APCI(–ve): 660 (M–1) 1H NMR: δ (DMSO): 12.45(br s,1H), 12.37(br s, 1H), 11.46(br s, 1H), 8.36(d, 1H), 7.76(s, 1H), 7.45(m, 2H), 7.30(d. 1H), 7.20(m. 4H), 7.0(s, 1H), 6.90(dd, 2H), 5.32(s, 1H), 4.25(m, 2H), 4.10(m, 2H), 3.88(m, 1H), 3.62(s, 2H), 2.50(q, 2H), 2.30(s, 3H), 1.10(t, 3H). MP: 235° C.

EXAMPLE 36

(±)-2-[2-[[4-[3,4-Dihydro-5-{2-hydroxy-8-methyl-5H-dibenzo[a,d]cyclohepten-5-yl}-2,4-dioxo-1(2H)-pyrimidiny]pyrimidin-2-yl]amino]acetylamino]-4-thiazoleacetic acid.

i) (±)-5-[2-Hydroxy-8-methyl-5H-dibenzo[a,d]cyclohepten-5-yl]-2,4(1H,3H)-pyrimidinedione A solution of borontribromide (1.0M in dichloromethane) (10 ml) was added to a mixture of the product from example 23 step (iv) (1.4 g) in dichloromethane (20 ml). After stirring for 2 hours, the reaction mixture was partitioned between 2M hydrochloric acid and ethyl acetate. The organic layer was washed with water, dried (MgSO$_4$) and evaporated under reduced pressure. Used directly in the next step.

MS: APCI(+ve): 333 (M+1).

ii) (±)-5-[2-[[1,1-dimethylethyl]dimethylsiloxy]-8-methyl-5H-dibenzo[a,d]cyclohepten-5-yl]-2,4(1H,3H)-pyrimidinedione Tert-butyl dimethylsilylchloride (0.98 g) was added to a mixture of the product from step (i) and imidazole (0.74 g) in dimethylformamide (20 ml). The reaction mixture was stirred for 3 hours and partitioned between water and ethyl acetate. The organic layer was washed with water, dried (MgSO$_4$) and evaporated under reduced pressure. Purification was by chromatography eluting with 50–70% ethyl acetate in isohexane. Yield 0.71 g.

MS: APCI(+ve): 447 (M+1).

iii) (±)-1-[2-Chloropyrimidin-4-yl]-5-[2-[[1,1-dimethylethyl]dimethylsiloxy]-8-methyl-5H-dibenzo[a,d]cyclohepten-5-yl]-2,4(1H,3H)-pyrimidinedione The subtitle compound was prepared from the product of step (ii) (0.70 g) by the method of example 6 step (i). Purified by chromatography eluting with 30–40% ethyl acetate in isohexane. Yield 0.76 g.

MS: APCI(+ve): 559 (M+1).

iv) (±)-2-[2-[[4-[3,4-Dihydro-5-{2-hydroxy-8-methyl-5H-dibenzo [a,d]cyclohepten-5-yl}-2,4-dioxo-1(2H)-pyrimidinyl]pyrimidin-2-yl]amino]acetylaminol-4-thiazoleacetic acid, ethyl ester The subtitle compound was prepared from the product of step (iii) (0.75 g) by the method of example 7 step (i). Purified by chromatography eluting with 70–100% ethyl acetate in isohexane. Yield 0.34 g.

MS: APCI(+ve): 652 (M+1).

v) (±)-2-[2-[[4-[3,4-Dihydro-5-{2-hydroxy-8-methyl-5H-dibenzo[a,d]cyclohepten-5-yl}-2,4-dioxo-1(2H)-pyrimidinyl]pyrimidin-2-yl]amino]acetylamino]-4-thiazoleacetic acid.

The title compound was prepared from the product of step (iv) (0.33 g) by the method of example 1 step (vii). Yield 0.14 g.

MS: APCI(+ve): 624 (M+1); 1H NMR: δ (DMSO, 90° C.) 12.03(br s,1H), 11.20(s,1H), 8.29(d,1H), 7.60(s,1H), 7.36–7.28(m,3H), 7.13–7.10(m,3H), 6.95(s,1H), 6.90–6.74 (m,4H), 5.24(s,1H), 4.29–4.18(m,2H),3.61(s,2H), 2.23(s, 3H). MP: 203° C. (dec.)

EXAMPLE 37

(±)-2-[2-[[4-[5-{2-Ethyl-8-methyl-5H-dibenzo[a,d]cyclohepten-5-yl}-3,4-dihydro-2,4-dioxo-1(2H)-pyrimidinyl]pyrimidin-2-yl][methyl]amino] acetylamino]-α-[methoxyimino]-4-thiazoleacetic acid i) 2-[2-[Methylamino]acetylamino]-α-[methoxyimino]-4-thiazoleacetic acid, ethyl ester The subtitle compound was prepared from N-[tert-butoxycarbonyl]sarcosine (2.00 g) and ethyl 2-amino-alpha-[methoxyimino]-4-thiazoleacetate (2.66 g) by the method of example 10 step (i).Yield 2.77 g.

MS: APCI(+ve): 301(M+1,100%).

ii) 2-[2-[[4-[5-{2-Ethyl-8-methyl-5H-dibenzo[a,d]cyclohepten-5-yl}-3,4-dihydro-2,4-dioxo-1(2H)-pyrimidinyl]pyrimidin-2-yl][methyl]amino]acetylamino]-α-[methoxyimino]-4-thiazoleacetic acid, ethyl ester The subtitle compound was prepared from the product of step (i) (0.7 g) and the product of example 15 step (viii) (0.5 g) by the method of example 7 step (i). The product was purified by chromatography eluting with 30% ethyl acetate in toluene. Yield 0.28 g.

MS:APCI(+ve): 721(M+1,80%).

iii) 2-[2-[[4-[5-{2-Ethyl-8-methyl-5H-dibenzo[a,d]cyclohepten-5-yl}-3,4-dihydro-2,4-dioxo-1(2H)-pyrimidinyl]pyrimidin-2-yl][methyl]amino]acetylamino]-α-[methoxyimino]-4-thiazoleacetic acid The title compound was prepared from the product of step (ii) (0.28 g) by the method of example 1 step (vii). Product was a 3:1 mixture of Z:E isomers. Yield 0.2 g.

MS: APCI(−ve): 691 (M−1); 1H NMR: δ (DMSO,90° C.) signals corresponding to Z-isomer: 12.50(br s,1H) signals corresponding to E-isomer: 12.40(br s,1H), 4.00(s,3H) combined signals: 11.21(s,1H), 8.30(d,1H), 7.90–7.70(br s,1H), 7.50–7.40(m,3H), 7.25(d,1H),7.20–7.10(m,4H), 6.90(d, 1H),6.86(d,1H), 5.34(s,1H), 4.55(s,2H), 3.91(s,3H), 3.05(s, 3H), 2.57(q,2H), 2.62(s,3H), 1.13(t,3H).

EXAMPLE 38

(±)-N-[(1H)-Tetrazol-5-yl]-1-[4-[5-{2-ethyl-8-methyl-5H-dibenzo[a,d]cyclohepten-5-yl}-3,4-dihydro-2,4-dioxo-1(2H)-pyrimidinyl]pyrimidin-2-yl]-3-azetidinecarboxamide The title compound was prepared from example 24 (0.42 g) and 5-aminotetrazole monohydrate (0.11 g) by the method of example 10 step (i). Yield 0.16 g.

MS: APCI(+ve): 589 (M+1); 1H NMR: δ (DMSO) 16.00 (br s,1H), 12.39(br s,1H), 11.47(br s,1H), 8.37(d,1H), 30 7.80(s,1H), 7.46(t,2H), 7.33(d,1H), 7.20(m,4H), 6.94(dd, 2H), 5.33(s,1H), 4.20(m,2H), 4.10(br s,1H), 3.90(m,2H), 2.50(m,2H), 2.22(s,3H), 1.10(m,3H). MP: 252° C.

EXAMPLE 39

(±)-2-[4-[5-{2-Ethyl-8-methyl-5H-dibenzo[a,d]cyclohepten-5-yl}-3,4-dihydro-2,4-dioxo-1(2H)-pyrimidinyl]pyrimidin-2-yl]amino-N-[4-[1H-tetrazol-5-ylmethyl]thiazol-2-yl]acetamide i) 2-Amino-4-thiazoleacetamide A solution of 2-amino-4-thiazoleacetic acid ethyl ester (15 g) in methanol (75 ml) and 0.880 arnmonia (75 ml) was stirred at room temperature for 72 hours then evaporated to dryness and triturated with toluene. Yield 11 g.

MS: APCI(+ve): 158 (M+1,100%).

ii) 2-Amino-4-thiazoleacetonitrile

A mixture of the product from step (i) (9.5 g) and phosphorous oxychloride (30 ml) was heated at 90° C. for 2 hours. The mixture was evaporated under reduced pressure and poured onto a mixture of ice water and ethyl acetate. The aqueous phase was adjusted to pH 9 with sodium bicarbon ate and extracted repeatedly with ethyl acetate. The combined extract was dried (MgSO$_4$) and evaporated. The residue was purified by chromatography eluting with ethyl acetate. Yield 6.1 g. 1H NMR: δ (DMSO) 7.08(br s,2H), 6.40(s,1H), 3.77(s,2H).

iii) 2-Amino-N-[4-cyanomethylthiazol-2-yl]acetamide

The subtitle compound was prepared from the product of step (ii) (3 g) by the method of example 10 step (i). Yield 1.58 g.

MS: APCI(+ve) 197 (M+1).

iv) (±)-N-[4-Cyanomethylthiazol-2-yl]-2-[[4-[5-{2-ethyl-8-methyl-5H-dibenzo[a,d]cyclohepten-5-yl}-3,4-dihydro-2,4-dioxo-1(2H)-pyrimidinyl]pyrimidin-2-yl]amino]acetamide The subtitle compound was prepared from the product of step (iii) (1.58 g) and the product of example 15 step (viii) (1.14 g) by the method of example 7 step (i). Yield 0.7 g.

MS: APCI(+ve): 617 (M+1,100%).

v) (±)-2-[4-[5-{2-Ethyl-8-methyl-5H-dibenzo[a,d]cyclohepten-5-yl}-3,4-dihydro-2,4dioxo-1(2H)-pyrimidinyl]pyrimidin-2-yl]amino-N-[4-[1H-tetrazol-5-ylmethyl]thiazol-2-yl]acetamide A mixture of the product of step (iv) (0.35 g) and trimethyltin azide (0.5 g) in toluene (10 ml) was heated at reflux for 48 hours. Methanol was added and the resultant precipitate filtered off. The solution was evaporated to dryness and the residue purified by reverse phase chromatography. The fraction containing product was concentrated under reduced pressure, acidified with 2N HCl and extracted with ethyl acetate. The extract was evaporated to dryness and the residue triturated with diethyl ether. The product was collected by filtration. Yield 0.16 g.

MS: APCI(+ve): 660 (M+1,100%); 1H NMR: δ (DMSO, 90° C.) 12.01(br s,1H), 11.17(s,1H), 8.28(d,1H), 7.63(d,1H), 7.50–7.35(m,2H), 7.30–7.10(m,6H), 7.00(s,1H), 6.91(s,2H), 5.32(s,1H), 4.32(d,2H), 4.21(d,2H), 2H),4.21(d,2H),2.55(q, 2H), 2.24(s,3H), 1.13(t,3H).

EXAMPLE 40

(±)[[5-[[4-[5-{2-Ethyl-8-methyl-5H-dibenzo[a,d]cyclohepten-5-yl}-3,4-dihydro-2,4-dioxo-1(2H)-pyrimidinyl]pyrimidin-2-yl]amino]acetylamino]-3-(1,2,4-thiadiazole)]acetic acid i) [5-Amino-3-(1,2,4-thiadiazole)]acetic acid, methyl ester A solution of [5-(ethoxycarbonylamino)-3-(1,2,4-thiadiazole)]acetic acid (Bull. Chem. Soc. Jpn. 1994,67, 1701) (6.70 g) and sodium hydroxide (2.43 g) in water (100 ml) was heated at reflux overnight and lyophilised. The residue was treated with a solution of acetyl chloride (21.3 ml) in methanol (200 ml). The solution was stirred overnight and evaporated. The residue was dissolved in water (100 ml), basified with saturated aqueous sodium bicarbonate solution and extracted with ethyl acetate. The extract was dried (MgSO$_4$) and evaporated and the residue purified by chromatography eluting with ethyl acetate. Yield 0.5 g.

MS: APCI(+ve) 174 (M+1, 100%).

ii) [5-[[[[(1,1-Dimethylethoxy)carbonyl]amino]methyl]carbonylamino]-3-(1,2,4-thiadiazole)]acetic acid, methyl ester The subtitle compound was prepared from the product of step (i) by the method of example 10 step (i).

MS: APCI(+ve) 231 (M+1,100%).

iii) (±)[[5-[[4-[5-{2-Ethyl-8-methyl-5H-dibenzo[a,d]cyclohepten-5-yl}-3,4-dihydro-2,4-dioxo-1(2H)-pyrimidinyl]pyrimidin-2-yl]amino]acetylamino]-3-(1,2,4-thiadiazole)]acetic acid, methyl ester The subtitle compound was prepared from the product of step (ii) and example 15 step (viii) by the method of example 7 step (i).

MS: APCI (+ve) 651 (M+1,100%).

iv) (±)[[5-[[4-[5-{2-Ethyl-8-methyl-5H-dibenzo[a,d]cyclohepten-5-yl}-3,4-dihydro-2,4-dioxo-1(2H)-pyrimidinyl]pyrimidin-2-yl]amino]acetylamino]-3-(1,2,4-thiadiazole)]acetic acid The title compound was prepared from the product of step (iii) by the method of example 1 step (vii).

MS: 637 (M+1,100%); 1H NMR: δ (DMSO,90° C.) 11.49 (br s,1H), 8.30 (d,1H), 7.64 (d,1H), 7.43–7.36 (m,2H), 7.30–7.20 (m,1H), 7.18–7.13 (m,5H), 6.91 (br s,2H), 5.32 (s,1H), 4.31 (d,2H), 3.79 (s,2H), 2.55 (q,2H), 2.35 (s,3H), 1.14 (t,3H). MP: 210–212° C.

EXAMPLE 41

(±)2-[5-{2-Ethyl-8-methyl-5H-dibenzo[a,d]cyclohepten-5-yl}-3,4-dihydro-2,4-dioxo-1(2H)-pyrimidinyl]-4-pyrimidinecarboxylic acid i) 2,6-Dichloro-4-pyrimidinecarboxylic acid, (1,1-dimethylethyl) ester A mixture of orotic acid (43 g) and phosphorous oxychloride (350 ml) was heated at reflux for 72 hours and evaporated. The residue was dissolved in tetrahydrofuran (300 ml) and treated with tert-butanol (150 ml). The solution was stirred at room temperature for 1 hour and potassium tert-butoxide (23 g) was added. The mixture was stirred at room temperature overnight and evaporated. The residue was partitioned between diethyl ether and water. The organic phase was washed with aqueous sodium bicarbonate and water, dried (MgSO$_4$) and evaporated. Yield 9.4 g.

MS: APCI (−ve) 248/250 (M−1) 191 (100%).

ii) 2-Chloro-6-propylthio-4-pyrimidinecarboxylic acid, (1,1-dimethylethyl) ester To a stirred solution of the product from step (i) (5.2 g) and triethylamine (4.2 ml) in dichloromethane (30 ml) at 0° C. was added propanethiol (0.9 ml). The mixture was stirred for 2 hours at 0° C., warmed to room temperature and stirred for a further 2 hours. The reaction mixture was partitioned between diethyl ether and 1M NaOH solution. The organic phase was dried (MgSO$_4$) and evaporated and the residue purified by chromatography eluting with 30–60% toluene in isohexane. Yield 3.84 g.

1H NMR: δ (CDCl$_3$) 7:61 (s,1H), 3.21 (t,2H), 1.83–1.71 (m,2H), 1.60 (s,9H), 1.06 (t,3H).

iii) 2-Chloro-4-pyrimidinecarboxylic acid, (1,1-dimethylethyl) ester

To a suspension of Raney® nickel (50% slurry in water, 10 g) in ethanol (20 ml) was added a solution of the product from step (ii) (3.83 g) in ethanol (20 ml). The mixture was stirred for 2 hours and treated with a further 5 g Raney® nickel. The mixture was stirred overnight and treated with a further 20 g Raney® nickel. After 1 hour the reaction mixture was filtered through Kieselguhr and the filtrate evaporated. The residue was purified by chromatography eluting with 5–10% ethyl acetate in isohexane. Yield 1.3 g.

1H NMR: δ (CDCl$_3$) 8.82 (d,1H), 7.85 (d,1H), 1.63 (s,9H).

iv)(±) 2-[5-{2-Ethyl-8-methyl-5H-dibenzo[a,d]cyclohepten-5-yl}-3,4-dihydro-2,4-dioxo-1(2H)-pyrimidinyl]-4-pyrimidinecarboxylic acid, (1,1-dimethylethyl) ester The subtitle compound was prepared from the product of step (iii) and the product of example 15 step (vii) by the method of example 19 step (ii).

MS: APCI (+ve) 523 (M+1) 467 (100%).

v) (±)2-[5-{2-Ethyl-8-methyl-5H-dibenzo[a,d]cyclohepten-5-yl}-3,4-dihydro-2,4-dioxo-1(2H)-pyrimidinyl]4-pyrimidinecarboxylic acid The title compound was prepared from the product of step (iv) by the method of example 17 step (iv).

MS: APCI (−ve) 465 (M−1,100%); 1H NMR: δ (DMSO) 9.10 (d,1H), 7.98 (d,1H), 7.47–7.42 (2×d, 2H), 7.22–7.13 (m,5H), 6.95–6.87 (q,2H), 5.34 (s,1H), 2.57 (q,2H), 2.27 (s,3H), 1.16 (t,3H).

EXAMPLE 42

(±)N-[[[2-[5-{2-Ethyl-8-methyl-5H-dibenzo [a,d] cyclohepten-5-yl}-3,4-dihydro-2,4-dioxo-1(2H)-pyrimidinyl]pyrimidin-4-yl]carbonyl]glycine i) (±)N-[[[2-[5-{2-Ethyl-8-methyl-5H-dibenzo[a,d]cyclohepten-5-yl}-3,4-dihydro-2,4-dioxo-1(2H)-pyrimidinyl]pyrimidin-4-yl]carbonyl]glycine, methyl ester The subtitle compound was prepared from example 41 and glycine methyl ester by the method of the first stage of example 10 step (i).

MS: APCI (+ve) 538 (M+1,100%).

ii) (±)N-[[[2-[5-{2-Ethyl-8-methyl-5H-dibenzo[a,d]cyclohepten-5-yl}-3,4-dihydro-2,4-dioxo-1(2H)-pyrimidinyl]pyrimidin-4-yl]carbonyl]glycine The title compound was prepared from the product of step (i) by the method of example 1 step (vii).

MS: APCI (+ve) 524 (M+1,100%); 1H NMR: δ (DMSO) 12.84 (s,1H), 11.54 (s,1H), 9.12 (d,1H), 8.90 (t,1H), 8.01 (d,1H), 7.46 (d,1H), 7.42 (d,1H), 7.22–7.16 (m,4H), 7.11 (s,1H), 6.99–6.90 (q,2H), 5.34 (s,1H), 4.02 (d,2H), 2.57 (q,2H), 1.15 (t,3H). MP: 195–8° C.

EXAMPLE 43

(±)2-[5-{2-Ethyl-8-methyl-5H-dibenzo[a,d]cyclohepten-5-yl}-3,4-dihydro-2,4-dioxo-1(2H)-pyrimidinyl]-N-[(1H)-tetrazol-5-yl]-4-pyrimidinecarboxamide The title compound was prepared from example 41 and 5-aminotetrazole by the method of the first stage of example 10 step (i).

MS: APCI (+ve) 534 (M+1) 506 (100%); 1H NMR: δ (DMSO) 12.25 br s,1H), 11.58 (s,1H), 9.21 (d,1H), 8.12 (d,1H), 7.47 (d,1H), 7.43 (d,1H), 7.22–7.17 (m,5H), 6.98–6.91 (q,2H), 5.36 (s,1H), 2.55 (q,2H), 2.25 (s,3H), 1.12 (t,3H).

EXAMPLE 44

(±)2-[[6-[5-{2-Ethyl-8-methyl-5H-dibenzo [a,d] cyclohepten-5-yl}-3,4-dihydro-2,4-dioxo-1(2H)-pyrimidinyl]pyridazin-3-yl]thio]acetic acid i) (±)5-{2-Ethyl-8-methyl-5H-dibenzo [a,d]cyclohepten-5-yl}-1-[6-chloropyridazin-3-yl]-2,4(1H,3H)-pyrimidinedione The subtitle compound was prepared from the product of example 15 step (vii) by the method of example 2 step (i).

1H NMR (CDCl₃) δ 8.25 (s,1H), 7.71 (d,1H), 7.43 (m,4H), 7.16 (m,4H), 6.90 (dd,2H), 5.37 (s,1H), 4.17 (s,2H), 3.79 (s,3H), 2.62 (q,2H), 2.31 (s,3H), 1.21 (t,3H).

ii) (±)2-[[6-[5-{2-Ethyl-8-methyl-5H-dibenzo [a,d] cyclohepten-5-yl}-3,4-dihydro-2,4-dioxo-1(2H)-pyrimidinyl]pyridazin-3-yl]thio]acetic acid The title compound was prepared from the product of step (i) by the method of example 1 step (vii).

5 MS: APCI (+ve) 513 (M+1,100%); 1H NMR: δ (DMSO) 12.89 (br s,1H), 11.59 (s,1H), 7.78 (s,2H), 7.45 (m,2H), 7.19 (m,5H), 6.90 (s,2H), 5.35 (s,1H), 4.13 (s,2H), 2.58 (q,2H), 2.28 (s,3H), 1.17 (t,3H). MP: 225–230° C.

EXAMPLE 45

(±)2-[4-[5-{2-Ethyl-8-methyl-5H-dibenzo [a,d] cyclohepten-5-yl}-3,4-dihydro-2,4-dioxo-1(2H)-pyrimidinyl]pyrimidin-2-yl amino]-N-[(1H)-tetrazol-5-yl]acetamide i) 2-[(1,1-Dimethylethoxy)carbonyl]amino-N-[(1H)-tetrazol-5-yl]acetamide, pyrrolidinium salt To a solution of N-(tert-butoxycarbonyl)glycine (2 g), 5-aminotetrazole monohydrate (1.4 g) and bromo-tris (pyrrolidino)-phosphonium hexafluorophosphate (7.52 g) in dimethylformamide (20 ml) was added N,N-diisopropylethylamine (4.4 g) followed by N,N-dimethyl-4-aminopyridine (1.4 g). After 16 hours the reaction mixture was diluted with ethyl acetate and washed with water and brine. The aqueous phase was adjusted to pH4 with tartaric acid and extracted repeatedly with ethyl acetate. The combined extract was dried (MgSO₄) and evaporated. The residue was triturated with ethyl acetate and the solid collected by filtration. Yield 1.4 g.

1H NMR δ (DMSO) 12.05 (br s,1H), 7.22 (t,1H), 3.83 (d,2H), 3.05–3.00 (m,4H), 1.80–1.75 (m,4H), 1.40 (s,9H).

ii) 2-Amino-N-[(1H)-tetrazol-5-yl]acetamide

The product of step (i) (1.4 g) was slurried in ethyl acetate, washed with 1N HCl and filtered. The filtrate was washed with water, dried (MgSO₄) and evaporated. The residue was dissolved in dichloromethane (50 ml) and trifluoroacetic acid (8 ml) and stirred at room temperature for 2 hours. The mixture was evaporated. The residue was azeotroped with toluene and triturated with isohexane. The product was collected by filtration. Yield 0.45 g.

1H NMR: δ (DMSO) 12.50 (br s,1H), 8.24 (br s,3H), 3.92 (br s,2H).

iii) (±)2-[4-[5-{2-Ethyl-8-methyl-5H-dibenzo [a,d] cyclohepten-5-yl}-3,4-dihydro-2,4-dioxo-1(2H)-pyrimidinyl]pyrimidin-2-yl]amino]-N-[(1H)-tetrazol-5-yl] acetamide The title compound was prepared from the product of step (ii) and the product of example 15 step (viii) by the method of example 7 step (i).

MS: APCI (+ve) 563 (M+1,100%); 1H NMR δ (DMSO, 90° C.) 11.80 (br s,1H), 11.21 (br s,1H), 8.30 (d,1H), 7.62 (s,1H), 7.42–7.37 (m,2H), 7.27 (br s,1H), 7.19–7.11 (m,5H), 6.91 (br s,2H), 5.32 (s,1H), 4.24 (d,2H), 2.55 (q,2H), 2.24 (s,3H), 1.14 (t,3H); MP: 220–225° C.

EXAMPLE 46

(±)N-[4-[5-{2-Ethyl-8-hydroxy-5H-dibenzo [a,d] cyclohepten-5-yl}-3,4-dihydro-2,4-dioxo-1(2H)-pyrimidinyl]pyrimidin-2-yl]-3-azetidinecarboxylic acid i) 2-(4-Ethylphenyl)-4,5-dihydro-4,4-dimethyloxazole The subtitle compound was prepared from 4-ethyl benzoic acid by the method of example 15 step (iii).

MS: APCI (+ve) 204 (M+1,100%).

ii) 2-(4-Ethyl-2-methylphenyl)-4,5-dihydro-4,4-dimethyloxazole

To a solution of the product from step (i) (43 g) in tetrahydrofuran (600 ml) at −10° C. was added n-butyllithium (2.5M solution in hexanes, 94 ml). The mixture was stirred for 2.5 hours at 0° C. then cooled to −30° C. and treated with methyl iodide (62 ml). The mixture was warmed to room temperature and partitioned between ethyl acetate and water. The organic phase was dried and evaporated and the residue purified by chromatography eluting with 5% ethyl acetate in isohexane. Yield 28.4 g.

MS: APCI (+ve) 218 (M+1,100%).

iii) 2-[2-[2-[3-Methoxyphenyl]ethyl]-4-methylphenyl]-4,5-dihydro-4,4-dimethyloxazole The subtitle compound was prepared from the product of step (ii) by the method of example 15 step (iv).

MS: APCI (+ve) 338 (M+1,100%).

iv) 2-[2-[3-Methoxyphenyl]ethyl]-4-methylbenzoic acid

The subtitle compound was prepared from the product of step (iii) by the method of example 15 step (v).

MS: APCI (−ve) 283 (M−1,100%).

v) 2-Ethyl-10,11-dihydro-8-methoxy-5H-dibenzo[a,d]cyclohepten-5-one

The subtitle compound was prepared from the product of step (iv) by the method of example 15 step (vi).

MS: APCI (+ve) 267 (M+1,100%).

vi) (±)-5-[2-Ethyl-8-methoxy-5H-dibenzo[a,d]cyclohepten-5-yl]-2,4(1H,3H)-pyrimidinedione The subtitle compound was prepared from the product of step (v) by the method of example 8 step (i).

MS: APCI (+ve) 361 (M+1,100%).

vii) (±)-5-[2-Ethyl-8-[(1,1-dimethylethyl)dimethylsilyloxy]-5H-dibenzo[a,d]cyclohepten-5-yl]-2,4(1H,3H)-pyrimidinedione A mixture of the product from step (vi) (7.1 g) and boron tribromide (1.0M solution in dichloromethane, 40 ml) in dichloromethane (30 ml) was stirred at room temperature for 4 hours then partitioned between ethyl acetate and 2M HCl. The organic phase was washed with water, dried (MgSO$_4$) and evaporated. The residue was dissolved in dimethylformamide (50 ml) and tert-butyldimethylsilyl chloride (4.52 g) and imidazole (3.4 g) were added. The reaction mixture was stirred at room temperature overnight and partitioned between ethyl acetate and water. The organic phase was washed with water, dried (MgSO$_4$) and evaporated. The residue was purified by chromatography eluting with 40–60% ethyl acetate in isohexane. Yield 5.23 g.

MS: APCI (+ve) 461 (M+1,100%).

viii) 1-[2-Chloropyrimidin-4-yl]-5-[2-ethyl-8-[(1,1-dimethylethyl)dimethylsilyloxy]-5H-dibenzo[a,d]cyclohepten-5-yl]-2,4(1H,3H)-pyrimidinedione The subtitle compound was prepared from the product of step (vii) by the method of example 1 step (v).

MS: APCI (+ve) 573 (M+1,100%).

ix) (±)2-[4-[5-{2-Ethyl-8-methyl-5H-dibenzo [a,d]cyclohepten-5-yl}-3,4-dihydro-2,4-dioxo-1(2H)-pyrimidinyl]pyrimidin-2-yl]amino]-N-[(1H)-tetrazol-5-yl]acetamide A mixture of the product from step (viii) (0.5 g), 3-carboxyazetidine (0.13 g) and N,N-diisopropylethylamine (0.52 ml) in 1-methyl-2-pyrrolidinone (10 ml) was heated at 90° C. for 6 hours and partitioned between ethyl acetate and 1M HCl. The organic phase was washed with water, dried (MgSO$_4$) and concentrated in vacuo to 10 ml. Isohexane (5 ml) was added and the product was collected by filtration. Yield 0.25 g.

MS: APCI (+ve) 524 (M+1,100%); 1H NMR: δ (DMSO, 90° C.) δ 12.42 (br s,1H), 11.18 (s,1H), 9.10 (s,1H), 8.31 (d,1H), 7.82 (s,1H), 7.39 (d,1H), 7.33–7.29 (m,2H), 7.21–7.18 (m,2H), 6.89–6.71 (m,4H), 5.25 (s,1H), 4.22–4.14 (m,2H), 4.06–4.03 (m,1H), 3.57–3.52 (m,1H), 2.60 (q,2H), 1.17 (t,3H). MP: 220° C.

EXAMPLE 47

(±)2-[[[4-[5-{2-Ethyl-8-hydroxy-5H-dibenzo [a,d]cyclohepten-5-yl}-3,4-dihydro-2,4-dioxo-1(2H)-pyrimidinyl]pyrimidin-2-yl]amino]acetylamino]-4-thiazoleacetic acid i) (±)2-[[[4-[5-{2-Ethyl-8-[(1,1-dimethylethyl)dimethylsilyloxy]-5H-dibenzo[a,d]cyclohepten-5-yl}-3,4-dihydro-2, 4-dioxo-1(2H)-pyrimidinyl]pyrimidin-2-yl]amino]acetylamino]-4-thiazoleacetic acid, ethyl ester The subtitle compound was prepared from the product of example 46 step (viii) and the product of example 10 step (i) by the method of example 7 step (i), with an acid wash (1M HCl) during work-up.

MS: APCI (+ve) 666 (M+1,100%).

ii) (±)2-[[[4-[5-{2-Ethyl-8-hydroxy-5H-dibenzo [a,d]cyclohepten-5-yl}-3,4-dihydro2,4-dioxo-1(2H)-pyrimidinyl]pyrimidin-2-yl]amino]acetylamino]-4-thiazoleacetic acid The title compound was prepared from the product of step (i) by the method of example 1 step (vii).

MS: APCI (+ve) 638 (M+1,100%); 1H NMR δ (DMSO, 90° C.) δ 12.00 (br s,1H), 11.19 (s,1H), 8.29 (d,1H), 7.62 (s,1H), 7.38 (d,1H), 7.29 (d,1H), 7.24 (br s,1H), 7.17–7.10 (m,3H), 6.95 (s,1H), 6.91–6.75 (m,4H), 5.25 (s,1H), 4.28–4.17 (m,2H), 3.61 (s,2H), 2.52 (q,2H), 1.13 (t,3H). MP: 225 ° C.

EXAMPLE 48

(±) 2-[5-{2-Ethyl-8-methyl-5H-dibenzo [a,d]cyclohepten-5-yl}-3,4-dihydro-2,4-dioxo-1(2H)-pyrimidinyl]-N-[{(1H)-tetrazol-5-ylamino}earboxymethyl]-4-pyrimidinecarboxamide A stirred solution of the product from example 41 step (v) (0.42 g), the product from example 45 step (ii) (0.345 g), N,N-diisopropylethylamine (0.7 ml) and bromo-tris (pyrrolidino)-phosphonium hexafluorophosphate (0.632 g) in dry N.N-dimethylformamide (10 ml) was treated with N,N-dimethyl-4-aminopyridine (0.111 g). After 96 hours the mixture was partitioned between 1N hydrochloric acid and ethyl acetate. The organic layer was washed with water, dried (MgSO$_4$) and concentrated to low volume. Addition of isohexane gave a solid which was purified by C18 reverse phase chromatography eluting with 50% to 80% methanol in 0.1% aqueous ammonium acetate solution. Yield 0.044 g MS:APCI (−ve) 589 (M−1, 100%); 1H NMR δ (DMSO) 15.94 (br s, 1H), 12.20 (br s, 1H), 11.55 (s, 1H), 9.14 (d, 1H), 9.05 (t, 1H), 8.03 (d, 1H), 7.44 (dd, 2H), 7.19 (m, 4H), 6.92 (dd, 2H), 5.35 (s, 1H), 4.26 (d,2H), 2.56 (q, 2H), 2.26 (s, 3H), 1.17 (t, 3H); MP: 215–220° C. dec.

EXAMPLE 49

(±)-4-[Carboxymethylamino]-2-[5-[2-ethyl-8-methyl-5H-dibenzo [a,d]cyclohepten-5-yl]-3,4-dihydro-2,4-dioxo-2H-pyrimidin-1-yl]-5-pyrimidinecarboxylic acid i) (±)-4-[[1,1-Dimethylethoxycarbonyl]methylamino]-2-[5-[2-ethyl-8-methyl-5H-dibenzo[a,d]cyclohepten-5-yl]-3,4-dihydro-2,4-dioxo-2H-pyrimidin-1-yl]-5-pyrimidinecarboxylic acid, methyl ester The subtitle compound was prepared from the products of example 17 step (ii) and example 15 step (vii) by the method of example 17 step (iii).

MS:APCI(+ve) 610 (M+1, 100%).

ii) (±)-4-[Carboxymethylamino]-2-[5-[2-ethyl-8-methyl-5H-dibenzo [a,d]cyclohepten-5-yl]-3,4-dihydro-2,4-dioxo-2H-pyrimidin-1-yl]-5-pyrimidinecarboxylic acid The title compound was prepared from the product of step (i) by the method of example 1 step (vii).

MS: APCI(+ve) 540 (M+1, 100%); 1H NMR δ (DMSO) 13.65 (br s,1H), 13.00 (br s,1H), 11.83 (t,1H), 11.38 (s,1H), 7.46–7.40 (m, 2H), 7.23–7.17 (m,5H), 6.92 (s,2H), 5.32 (s,1H), 4.16 (d,2H), 2.58 (q,2H), 2.28 (s,3H), 1.16 (t,3H). MP:>200° C. (decomp.).

EXAMPLE 50

5-[2,8-Dimethyl-5H-dibenzo[a,d]cyclohepten-5-yl]-3,4-dihydro-2-oxo-4-thioxo-1(2H)-pyrimidine The title compound was prepared from the product of example 8 step (i) (4 g) by the method of example 1 step (vi). Yield 0.5 g MS: APCI (+ve): 347 (M+1, 100%), APCI (–ve): 345 (M–1, 100%); 1H NMR δ (DMSO) 12.33 (s, 1H), 11.19 (br s, 1H), 7.54 (d, 2H), 7.20(s+d, 4H), 6.9 (s,2H), 6.74 (s, 1H), 5.82 (s, 1H), 2.30 (s, 6H) MP: 287° C.

EXAMPLE 51

5-[2,8-Dimethyl-5H-dibenzo[a,d]cyclohepten-5-yl]-1-methyl-3,4-dihydro-2-oxo-4-thioxo-1(2H)-pyrimidine i) 10,11-Dihydro-2,8-dimethyl-5H-dibenzo[a,d]cyclohepten-5-ol Diisobutylaluminium hydride (5.5 ml of a 1M solution in tetrahydrofuran) was added dropwise to 10,11-dihydro-2,8-dimethyl-5H-dibenzo[a,d]cyclohepten-5-one (European Patent, 1993, 0 589 322 A1) (1.2 g) in tetrahydrofuran (20 ml) at–78 ° C. After 1 hour the cooling bath was removed and the reaction was stirred at r.t. for 2 hours. The reaction was quenched with brine and methanol. After 0.5 hours the reaction was partitioned between ethyl acetate and water. The ethyl acetate solution was washed with water, brine, dried (MgSO$_4$) and evaporated. Purification was by chromatography eluting with toluene. Yield 1.2 g. Used directly in step (ii)

ii) 5-(2,8-Dimethyl-5H-dibenzo[a,d]cyclohepten-5-yl)-1-methyl-2,4(3H)-pyrimidinedione To a solution of the product of step (i) (0.094 g) in trifluoroacetic acid (4 ml) under a nitrogen atmosphere was added 1-methyluracil (0.01 g), and the mixture stirred at room temperature for 1 hour. Evaporation of solvent afforded an orange oil which was azeotroped once with acetonitrile (5 ml). The crude product was redissolved in acetonitrile (2 ml), and stirred at room temperature for 0.5 h, giving a white precipitate. The reaction mixture was diluted with water (10 ml) and the white precipitate isolated by filtration. Yield: 0.085 g MS: APCI(+ve) 345 (M+1, 100%); 1H NMR: δ (CDCl$_3$) 7.83 (br s,1H), 7.40 (d, 2H), 7.18 (d, 2H), 7.13 (s, 2H), 6.83 (s,2H), 6.56 (s, 1H), 5.29 (s, 1H), 3.18 (s, 3H), 2.33 (s, 6H). MP: 260° C.

iii) 5-[2,8-Dimethyl-5H-dibenzo[a,d]cyclohepten-5-yl]-1-methyl-3,4-dihydro-2-oxo-4-thioxo-1(2H)-pyrimidine The title product was prepared from the product of step (ii) (0.14 g) by the method of example 1 step (vi). Purification was by chromatography eluting with 30% ethyl acetate in isohexane. Yield:0.10 g MS: APCI(+ve) 361 (M+1, 100%); 1H NMR δ (CDCl$_3$) 9.27 (br s, 1H), 7.52 (d, 2H), 7.17 (d, 2H), 7.13 (s, 2H), 6.93 (s,1H), 6.85 (s, 2H), 5.83 (s, 1H), 3.22 (s, 3H), 2.33 (s, 6H). MP: 275° C.

PHARMACOLOGICAL DATA

The following example describes the assay used to determine how strongly the compounds of the invention bind to P2-purinoceptor 7-TM G-protein coupled receptors. The assay used a human P2Y2 receptor clone which was isolated from HL60 cells cDNA and then stably transfected into a Jurkat cell line (using methods described in "Cloning and Characterisation of a Bovine P$_{2Y}$ Receptor" Henderson et al (1995), 212, 2, 648–656; Parr et al Proc. Natl. Acad. Sci USA (1994), 91, 3275–3279 and Proc Natl Acad Sci USA (1994), 91, 13067). The cloned receptor mediates an increase in intracellular calcium in the cell line, which possesses no endogenous nucleotide receptor of its own.

The transfected Jurkat cells were maintained at a concentration of from about $1\times10^5$ to $10\times10^5$ cells/ml in RPMI containing 4% heat inactivated bovine serum, 2% penicillin/streptomycin and 1% glutamine. The cells were incubated at 37° C. in an atmosphere of air with 5% $CO_2$.

The cells were spun down at 1000 r.p.m. for 5 minutes and resuspended in 10 ml basal salt solution (BSS) containing 125 mM of NaCl, 5 mM of KCl, 1 mM of MgCl, 1.5 mM of CaCl$_2$, 25 mM of HEPES, 5 mM of glucose and 1 mg/ml of bovine serum albumin, having a pH of 7.3. The concentration of cells was determined using a Technicon cell counter. From $0.75\times10^8$ to $1\times10^8$ cells were spun down, resuspended to a concentration of $3.3\times10^7$ cells/ml in BSS and incubated with either 17 μM fluo-3AM or 17 μM Fura-2AM at 37° C. for 35 minutes with vigorous shaking. The dye used was dependent upon the fluorescence and absorption properties of the compounds of the invention. In general for compounds of formula (I) wherein $Q^1$ represents a S atom, fluo-3AM was used and for compounds wherein $Q^1$ represents an O atom, either fluo-3AM or fura-2AM were used. The cells were again spun down and washed once with the same volume of BSS before being resuspended in BSS to a concentration of $1\times10^6$ cells/ml ready for testing.

When fluo-3AM was used as the dye, the cell solution was left at room temperature to recover for approximately 30 minutes before testing.

Fura-2AM loaded cells were divided into aliquots of about 10 ml and were warmed to 37° C. for 10 minutes before testing.

Calcium responses were measured on a SPEX Fluomax using 508 nm excitation and 525 nm emission wavelengths at room temperature for Fluo-3AM loaded cells and 340/380 nm excitation and 510 nm emission wavelengths for Fura-2AM loaded cells. Each cuvette contained 2 ml of cells and was stirred at high speed throughout the test. Basal fluorescence was measured for 5 seconds before 20 μl of a $10^{-2}$–$10^{-6}$M solution of the test compound in water was added to the 2 ml solution of the cells. The response was calibrated by the addition of Triton-X-100 (68 μl, 10% solution) and then EGTA (180 μl, 0.5 M solution). For each compound the response was compared to that of UTP.

The compounds exemplified have pa2 values greater than 4.0.

What is claimed is:

1. A compound of formula I:

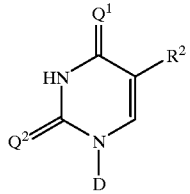

in which:

D is hydrogen, $C_{1-6}$alkyl or a group of formula (a):

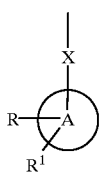

where A is a 6-membered heterocyclic ring containing 1 to 3 nitrogen atoms or a fused 5,6-bicyclic ring containing 1 to 4 nitrogen atoms;

X is a bond or $CH_2$ group;

R is hydrogen, $NO_2$, $NH_2$, $N(C_{1-6}alkyl)_2$, $CO_2H$, $CO_2C_{1-6}$alkyl, phenyl substituted by $CH_2CO_2H$, or $CONR^3R^4$ where $R^3$ and $R^4$ are independently hydrogen, $C_{1-6}$alkyl optionally substituted by hydroxy and/or optionally interrupted by oxygen, nitrogen or sulfur;

$R^1$ is —$R^5$-tetrazol-5-yl where $R^5$ is a bond, $OCH_2$, $SCH_2$, CONH, $CONHCH_2$, $CONHCH_2CONH$, $NHCH_2CONH$, $NHCH(R^3)$ or —$R^5$—$CO_2H$ where $R^5$ is a bond, $OCH_2$, $SCH_2$, $CONHCH_2$ or $NHCH(R^3)$ where $R^3$ is as defined above or $R^5$ is $NR^6(CH_2)_q$ where $R^6$ is hydrogen or $C_{1-6}$alkyl and q is 1 or 2, or $R^1$ is a group of formula (i):

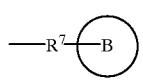

where B is a 4-, 5-, or 6-membered saturated ring containing a nitrogen atom optionally substituted by hydroxy and substituted by $CO_2H$ or CONH-Het where Het is tetrazol-5-yl, or a thiazole or thiadiazole ring substituted by $CH_2CO_2H$, or B is a 5-membered aromatic heterocyclic ring containing 1 to 3 heteroatoms selected from nitrogen, oxygen or sulfur optionally substituted by $CF_3$, $CO_2H$, $CH_2CO_2H$, $C(CO_2H)$=N—OMe, tetrazol-5-yl or $CH_2$tetrazol-5-yl; and $R^7$ is a bond, sulfur atom, a group —$NR^8$—$CH(CO_2H)$—$CH_2$—, or a group —$CONR^8(CH_2)_pCONR^9$— or —$NR^8$—$(CH_2)_p$—$CONR^9$— where $R^8$ and $R^9$ are independently hydrogen or $C_{1-6}$alkyl and p is 1 or 2;

$R^2$ is a group of formula (ii) or (iii):

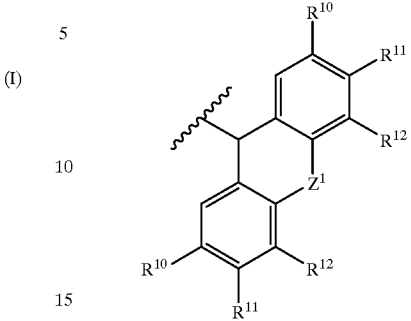

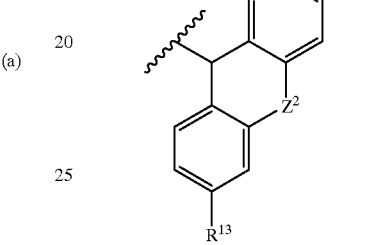

where $R^{10}$ groups are independently hydrogen, halogen, methoxy, methylthio or $C_{1-2}$alkyl (optionally substituted by one or more fluorine atoms);

$R^{11}$ groups are independently hydrogen, halogen, hydroxy, $C_{1-3}$ alkylthio, $C_{1-4}$alkyl (optionally substituted by one or more fluorine atoms), $C_{3-4}$ cycloalkyl, $MeOCH_2$, $MeSCH_2$ or $C_{1-2}$alkoxy;

$R^{12}$ groups are independently hydrogen, halogen or methyl (optionally substituted by one or more fluorine atoms);

$Z^1$ is CH=CH, CF=CH or CF=CF;

$Z^2$ is a single bond, oxygen, sulphur, $CH_2CH$=CH, $CH_2CH$=$CHCH_2$ or a $C_{1-4}$alkylene group optionally interrupted by an oxygen or sulphur atom;

$R^{13}$ are independently hydrogen, halogen, $C_{1-2}$alkyl, $CF_3$ or a methylthio group or hydroxy;

$Q^1$ and $Q^2$ each independently represent an O or S; provided that when $Q^1$ is oxygen, $R^2$ is a group of formula (ii).

2. A compound according to claim 1 in which D is hydrogen or $C_{1-6}$alkyl.

3. A compound according to claim 1 in which D is a group of formula (a) where A is pyridine or pyrimidine.

4. A compound according to claim 1 in which R is hydrogen.

5. A compound according to claim 1 in which $R^1$ is a group —$R^5$—$CO_2H$, where $R^5$ is $SCH_2$, $NHCH_2$ or $NMeCH_2$.

6. A compound according to claim 1 in which $R^7$ is a bond and B is a 4- or 5-membered saturated ring containing a nitrogen atom substituted by $CO_2H$ and optionally substituted by hydroxy.

7. A compound according to claim 1 in which B is a 5-membered aromatic heterocycle and $R^7$ is a group —$NR^8$—$(CH_2)_p$—$CONR^9$—.

8. A compound according to claim 1 in which B is thiazole or thiadiazole substituted by $CO_2H$ or $CH_2CO_2H$.

9. A compound according to claim 1 in which $Q^1$ is S or O and $Q^2$ is O.

10. A compound according to claim 1 which is:
- 6-[[5-{5H-Dibenzo[a,d]cyclohepten-5-yl}-3,4-dihydro-2-oxo-4-thioxo-1(2H)-pyrimidinyl]methyl]-2-pyridinecarboxylic acid;
- 2-[[6-[5-{5H-Dibenzo[a,d]cyclohepten-5-yl}-3,4-dihydro-2-oxo-4-thioxo-1(2H)-pyrimidinyl]pyridazin-3-yl]thio]acetic acid;
- 5-[5H-Dibenzo[a,d]cyclohepten-5-yl]-1-[6-[[5-[trifluoromethyl]-1,2,4-triazol-3-yl]thio]pyridazin-3-yl]-2,4(1H,3H)-pyrimidinedione;
- 5-[5H-Dibenzo[a,d]cyclohepten-5-yl]-3,4-dihydro-4-thioxo-1-[6-[[5-[trifluoromethyl]-1,2,4-triazol-3-yl]thio]pyridazin-3-yl]-2(1H)-pyrimidinone;
- 4-[2-[5-{5H-Dibenzo[a,d]cyclohepten-5-yl}-3,4-dihydro-2-oxo-4-thioxo-1(2H)-pyrimidinyl]-4-[carboxymethylthio]pyrimidin-5-yl]phenylacetic acid;
- 2-[[4-[5-{5H-Dibenzo[a,d]cyclohepten-5-yl}-3,4-dihydro-2-oxo-4-thioxo-1(2H)-pyrimidinyl]pyrimidin-2-yl]thio]acetic acid;
- N-[4-[5-{5H-Dibenzo[a,d]cyclohepten-5-yl}-3,4-dihydro-2-oxo-4-thioxo-1(2H)-pyrimidinyl]pyrimidin-2-yl]glycine;
- N-[4-[5-{2,8-Dimethyl-5H-dibenzo[a,d]cyclohepten-5-yl}-3,4-dihydro-2,4-dioxo-1(2H)-pyrimidinyl]pyrimidin-2-yl]glycine;
- N-[4-[5-{2,8-Dimethyl-5H-dibenzo[a,d]cyclohepten-5-yl}-3,4-dihydro-2-oxo-4-thioxo-1(2H)-pyrimidinyl]pyrimidin-2-yl]glycine;
- 2-[2-[[4-[5-{2,8-Dimethyl-5H-dibenzo[a,d]cyclohepten-5-yl}-3,4-dihydro-2,4-dioxo-1(2H)-pyrimidinyl]pyrimidin-2-yl]amino]acetylamino]-4-thiazoleacetic acid;
- N-[4-[5-{5H-Dibenzo[a,d]cyclohepten-5-yl}-3,4-dihydro-2,4-dioxo-1(2H)-pyrimidinyl]pyrimidin-2-yl]-L-proline;
- N-[4-[-5-{2,8-Dimethyl-5H-dibenzo[a,d]cyclohepten-5-yl}-3,4-dihydro-2,4-dioxo-1(2H)-pyrimidinyl]pyrimidin-2-yl]-L-proline;
- (2S-trans)-N-[4-[5-{2,8-Dimethyl-5H-dibenzo[a,d]cyclohepten-5-yl}-3,4-dihydro-2,4-dioxo-1(2H)-pyrimidinyl]pyrimidin-2-yl]-4-hydroxy-2-pyrrolidinecarboxylic acid;
- $N^\alpha$-[4-[5-{2,8-Dimethyl-5H-dibenzo[a,d]cyclohepten-5-yl}-3,4-dihydro-2,4-dioxo-1(2H)-pyrimidinyl]pyrimidin-2-yl]-L-histidine;
- (±)-2-[2-[[4-[5-{2-Ethyl-8-methyl-5H-dibenzo[a,d]cyclohepten-5-yl}-3,4-dihydro-2,4-dioxo-1(2H)-pyrimidinyl]pyrimidin-2-yl]amino]acetylainino]-4-thiazoleacetic acid;
- 2-[2-[[2-[Dimethylamino]-4-[5-{2,8-dimethyl-5H-dibenzo[a,d]cyclohepten-5-yl}-3,4-dihydro-2,4-dioxo-1(2H)-pyrimidinyl]pyrimidin-6-yl]amino]acetylamino]-4-thiazoleacetic acid;
- N-[2-[5-{2,8-Dimethyl-5H-dibenzo[a,d]cyclohepten-5-yl}-3,4-dihydro-2,4-dioxo-1(2H)-pyrimidinyl]-5-[methoxycarbonyl]pyrimidin-4-yl]glycine;
- 4-[[Carboxymethyl]amino]-2-[5-{2,8-dimethyl-5H-dibenzo[a,d]cyclohepten-5-yl}-3,4-dihydro-2,4-dioxo-1(2H)-pyrimidinyl]-5-pyrimidinecarboxylic acid;
- (±)-N-[4-[5-{2-Ethyl-8-methyl-5H-dibenzo[a,d]cyclohepten-5-yl}-3,4-dihydro-2-oxo-4-thioxo-1(2H)-pyrimidinyl]pyrimidin-2-yl]-N-methylglycine;
- (±)-2-[2-[[4-[5-{2-Ethyl-8-methyl-5H-dibenzo[a,d]cyclohepten-5-yl}-3,4-dihydro-2-oxo-4-thioxo-1(2H)-pyrimidinyl]pyrimidin-2-yl][methyl]amino]acetylamino]-4-thiazoleacetic acid;
- 2-[2-[[4-[5-{2,8-Dimethyl-5H-dibenzo[a,d]cyclohepten-5-yl}-3,4-dihydro-2,4-dioxo-1(2H)-pyrimidinyl]pyrimidin-2-yl][methyl]amino]acetylamino]-4-thiazoleacetic acid;
- (±)-2-[2-[[4-[5-{2-Ethyl-8-methyl-5H-dibenzo[a,d]cyclohepten-5-yl}-3,4-dihydro-2,4-dioxo-1(2H)-pyrimidinyl]pyrimidin-2-yl][methyl]amino]acetylamino]-4-thiazoleacetic acid;
- (±)-2-[2-[[4-[3,4-Dihydro-5-{2-methoxy-8-methyl-5H-dibenzo[a,d]cyclohepten-5-yl}-2,4-dioxo-1(2H)-pyrimidinyl]pyrimidin-2-yl][methyl]amino]acetylamino]-4-thiazoleacetic acid;
- (±)N-[4-[5-{2-Ethyl-8-methyl-5H-dibenzo[a,d]cyclohepten-5-yl}-3,4-dihydro-2,4-dioxo-1(2H)-pyrimidinyl]pyrimidin-2-yl]-3-azetidinecarboxylic acid;
- 2-[2-[[6-[5-{2,8-Dimethyl-5H-dibenzo[a,d]cyclohepten-5-yl}-3,4-dihydro-2-oxo-4-thioxo-1(2H)-pyrimidinyl]pyrimidin-4-yl][methyl]amino]acetylamino]-4-thiazoleacetic acid;
- (±)-N-[4-[5-{2-Ethyl-8-methyl-5H-dibenzo[a,d]cyclohepten-5-yl}-3,4-dihydro-2,4-dioxo-1(2H)-pyrimidinyl]pyrimidin-2-yl]-L-proline;
- (±)-N-[4-[5-{2-Ethyl-8-methyl-5H-dibenzo[a,d]cyclohepten-5-yl}-3,4-dihydro-2-oxo-4-thioxo-1(2H)-pyrimidinyl]pyrimidin-2-yl]-L-proline;
- (±)-2-[5-{2-Ethyl-8-methyl-5H-dibenzo[a,d]cyclohepten-5-yl}-3,4-dihydro-2,4-dioxo-1(2H)-pyrimidinyl]-9H-purine-9-acetic acid;
- N-[2-[5-{2-Ethyl-8-methyl-5H-dibenzo[a,d]cyclohepten-5-yl}-3,4-dihydro-2,4-dioxo-1(2H)-pyrimidinyl]-5-nitropyrimidin-4-yl]glycine;
- (±)-2-[2-[[4-[3,4-dihydro-5-{2-methyl-8-[1-methylethyl]-5H-dibenzo[a,d]cyclohepten-5 -yl}-2,4-dioxo-1(2H)-pyrimidinyl]pyrimidin-2-yl]amino]acetylamino]-4-thiazoleacetic acid;
- (±)-2-[2-[[4-[3,4-Dihydro-5-{2-methyl-8-propyl-5H-dibenzo[a,d]cyclohepten-5-yl}-2,4-dioxo-1(2H)-pyrimidinyl]pyrimidin-2-yl]amino]acetylamino]-4-thiazoleacetic acid;
- (±)-N-[4-[3,4-Dihydro-5-{2-methyl-8-propyl-5H-dibenzo[a,d]cyclohepten-5-yl}-2-oxo-4-thioxo-1(2H)-pyrimidinyl]pyrimidinyl]pyrimidin-2-yl]-N-methylglycine;
- (±)-2-[2-[[4-[5-{2-Ethyl-8-methyl-5H-dibenzo[a,d]cyclohepten-5-yl}-3,4-dihydro-2,4-dioxo-1(2H)-pyrimidinyl]pyrimidin-2-yl]amino]acetylamino]-5-thiazoleacetic acid;
- (±)-2-[2-[[4-[5-{2-Ethyl-8-methyl-5H-dibenzo[a,d]cyclohepten-5-yl}-3,4-dihydro-2,4-dioxo-1(2H)-pyrimidinyl]pyrimidin-2-yl][methyl]amino]acetylamino]-4-thiazolecarboxylic acid;
- (±)-2-[[1-[4-[5-{2-Ethyl-8-methyl-5H-dibenzo[a,d]cyclohepten-5-yl}-3,4-dihydro-2,4-dioxo-1(2H)-pyrimidinyl]pyrimidin-2-yl]azetidin-3-yl]carbonylamino]-4-thiazoleacetic acid;
- (±)-2-[2-[[4-[3,4-Dihydro-5-{2-hydroxy-8-methyl-5H-dibenzo[a,d]cyclohepten-5-yl}-2,4-dioxo-1(2H)-pyrimidinyl]pyrimidin-2-yl]amino]acetylamino]-4-thiazoleacetic acid;
- (±)-2-[2-[[4-[5-{2-Ethyl-8-methyl-5H-dibenzo[a,d]cyclohepten-5-yl}-3,4-dihydro-2,4-dioxo-1(2H)- pyrimidinyl]pyrimidin-2-yl][methyl]amino]
acetylamino]-α-[methoxyimino]-4-thiazoleacetic acid;

(±)-N-[(1H)-Tetrazol-5-yl]-1-[4-[5-{2-ethyl-8-methyl-
5H-dibenzo[a,d]cyclohepten-5yl}-3,4-dihydro-2,4-
dioxo-1(2H)-pyrimidinyl]pyrimidin-2-yl]-3-
azetidinecarboxamide;

(±)-2-[4-[5-{2-Ethyl-8-methyl-5H-dibenzo[a,d]
cyclohepten-5-yl}-3,4-dihydro-2,4-dioxo-1(2H)-
pyrimidinyl]pyrimidin-2-yl]amino-N-[4-[1H-tetrazol-
5-ylmethyl]thiazol-2-yl]acetamide;

(±)[[5-[[4-[5-{2-Ethyl-8-methyl-5H-dibenzo[a,d]
cyclohepten-5-yl}-3,4-dihydro-2,4-dioxo-1(2H)-
pyrimidinyl]pyrimidin-2-yl]amino]acetylamino]-3-(1,
2,4-thiadiazole)]acetic acid;

(±)2-[5-{2-Ethyl-8-methyl-5H-dibenzo[a,d]cyclohepten-
5-yl}-3,4-dihydro-2,4-dioxo-1(2H)-pyrimidinyl]-4-
pyrimidinecarboxylic acid;

(±)N-[[[2-[5-{2-Ethyl-8-methyl-5H-dibenzo[a,d]
cyclohepten-5-yl}-3,4-dihydro-2,4-dioxo-1(2H)-
pyrimidinyl]pyrimidin-4-yl]carbonyl]glycine;

(±)2-[5-{2-Ethyl-8-methyl-5H-dibenzo[a,d]cyclohepten-
5-yl}-3,4-dihydro-2,4-dioxo-1(2H)-pyrimidinyl]-N-
[(1H)-tetrazol-5-yl]-4-pyrimidinecarboxamide;

(±)2-[[6-[5-{2-Ethyl-8-methyl-5H-dibenzo[a,d]
cyclohepten-5-yl}-3,4-dihydro-2,4-dioxo-1(2H)-
pyrimidinyl]pyridazin-3-yl]thio]acetic acid;

(±)2-[4-[5-{2-Ethyl-8-methyl-5H-dibenzo[a,d]
cyclohepten-5-yl}-3,4-dihydro-2,4-dioxo-1(2H)-
pyrimidinyl]pyrimidin-2-yl]amino]-N-[(1H)-tetrazol-
5-yl]acetamide;

(±)N-[4-[5-{2-Ethyl-8-hydroxy-5H-dibenzo[a,d]
cyclohepten-5-yl}-3,4-dihydro-2,4-dioxo-1(2H)-
pyrimidinyl]pyrimidin-2-yl]-3-azetidinecarboxylic
acid;

(±)2-[[[4-[5-{2-Ethyl-8-hydroxy-5H-dibenzo[a,d]
cyclohepten-5-yl}-3,4-dihydro-2,4-dioxo-1(2H)-
pyrimidinyl]pyrimidin-2-yl]amino]acetylamino]-4-
thiazoleacetic acid;

(±)2-[5-{2-Ethyl-8-methyl-5H-dibenzo[a,d]cyclohepten-
5-yl}-3,4-dihydro-2,4-dioxo-1(2H)-pyrimidinyl]-N-[{
(1H)-tetrazol-5-ylamino}carboxymethyl]-4-
pyrimidinecarboxamide;

(±)-4-[Carboxymethylamino]-2-[5-[2-ethyl-8-methyl-
5H-dibenzo[a,d]cyclohepten-5-yl]-3,4-dihydro-2,4-
dioxo-2H-pyrimidin-1-yl]-5-pyrimidinecarboxylic
acid;

5-[2,8-Dimethyl-5H-dibenzo[a,d]cyclohepten-5-yl]-3,4-
dihydro-2-oxo-4-thioxo-1(2H)-pyrimidine;

5-[2,8-Dimethyl-5H-dibenzo[a,d]cyclohepten-5-yl]-1-
methyl-3,4-dihydro-2-oxo-4-thioxo-1(2H)-pyrimidine;

or salts thereof.

11. A process for the preparation of compounds of formula I as defined in claim 1 which comprises:

(a) reacting a compound of formula (II):

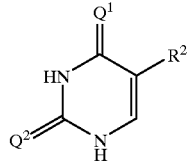

(II)

where $Q^1$ and $Q^2$ are as defined in formula (I) and $R^2$ is as defined in formula (I) or are protected derivatives thereof with a compound of formula (III):

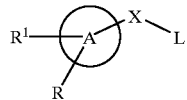

(III)

where R, $R^1$ and A are as defined in formula (I) or are protected derivatives thereof, X is as defined in formula (I) and L is a leaving group, or (b) reacting a compound of formula (IV):

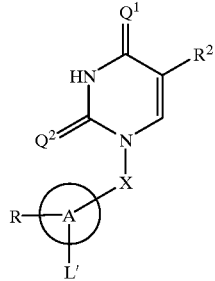

(IV)

where $Q^1$, $Q^2$ and X are as defined in formula (I), R and A are as defined in formula (I) or are protected derivatives thereof and L' is a leaving group with a compound of formula (V), (VI) or (VII):

$HNR^8—(CH_2)_p—CONR^9—B$      (V)

$HNR^8—CH(CO_2H)—CH_2—B$      (VI)

(VII)

where $R^8$, $R^9$ and p are as defined in formula (I) and B is as defined in formula (I) or is a protected derivative thereof, or (c) when $R^1$ is a group $—R^5—CO_2H$ and $R^5$ is $SCH_2$ or $NR^6(CH_2)_q$, reacting a compound of formula (IV) as defined above with a compound $H—R^5—CO_2R^{14}$ where $R^5$ is $SCH_2$ or $NR^6(CH_2)_q$ and $R^{14}$ is an ester forming group;

and optionally thereafter (a), (b) or (c) in any order:
  removing any protecting groups
  converting the compound of formula (I) into a further compound of formula (I)
  forming a salt.

12. A pharmaceutical composition comprising an effective amount of a compound of formula I or a salt or solvate thereof as defined in claim 1 in association with a pharmaceutically acceptable adjuvant, diluent or carrier.

* * * * *